US012625134B2

(12) United States Patent
Swager et al.

(10) Patent No.: US 12,625,134 B2
(45) Date of Patent: May 12, 2026

(54) COMPLEX LIQUID CRYSTAL DROPLETS

(71) Applicant: Massachusetts Institute of Technology, Cambridge, MA (US)

(72) Inventors: Timothy Manning Swager, Newton, MA (US); Cassandra Zentner, Brighton, MA (US); Alberto Concellon Allueva, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1319 days.

(21) Appl. No.: 17/001,401

(22) Filed: Aug. 24, 2020

(65) Prior Publication Data

US 2021/0041425 A1 Feb. 11, 2021

Related U.S. Application Data

(63) Continuation-in-part of application No. 16/201,961, filed on Nov. 27, 2018, now Pat. No. 11,119,098, which is a continuation-in-part of application No. 16/113,520, filed on Aug. 27, 2018, now abandoned, which is a continuation of application No. 15/269,543, filed on Sep. 19, 2016, now Pat. No. 10,060,913, said application No. 16/201,961 is a continuation-in-part of application No. 14/929,117, filed on Oct. 30, 2015, now Pat. No. 10,252,231.

(60) Provisional application No. 62/925,756, filed on Oct. 24, 2019, provisional application No. 62/073,896, filed on Oct. 31, 2014.

(51) Int. Cl.

| | |
|---|---|
| ***B01F 23/41*** | (2022.01) |
| ***C12Q 1/6834*** | (2018.01) |
| ***G01N 21/59*** | (2006.01) |
| ***G01N 21/77*** | (2006.01) |
| ***G01N 33/543*** | (2006.01) |

(52) U.S. Cl.
CPC ....... *G01N 33/5432* (2013.01); *B01F 23/414* (2022.01); *C12Q 1/6834* (2013.01); *G01N 21/59* (2013.01); *G01N 21/77* (2013.01); *G01N 33/54366* (2013.01); *G01N 2021/7783* (2013.01)

(58) Field of Classification Search
CPC .................. B01F 23/4144; B01F 23/41-4146
See application file for complete search history.

(56) References Cited

U.S. PATENT DOCUMENTS

| | | | |
|---|---|---|---|
| 3,826,613 A | 7/1974 | Parikh et al. | |
| 4,663,277 A | 5/1987 | Wang | |
| 4,870,026 A | 9/1989 | Wands et al. | |
| 4,912,034 A | 3/1990 | Kalra et al. | |
| 5,066,465 A | 11/1991 | Kano et al. | |
| 5,217,648 A | 6/1993 | Beissinger et al. | |
| 5,332,661 A | 7/1994 | Adamczyk et al. | |
| 5,387,676 A | 2/1995 | Zavada et al. | |
| 5,516,635 A | 5/1996 | Ekins et al. | |
| 5,980,936 A | 11/1999 | Krafft et al. | |
| 6,180,418 B1 | 1/2001 | Lee | |
| 6,271,202 B1 | 8/2001 | Kudsk | |
| 6,710,092 B2 | 3/2004 | Scher et al. | |
| 7,067,590 B2 | 6/2006 | Sato et al. | |
| 7,625,951 B2 | 12/2009 | Daunert et al. | |
| 7,767,017 B2 | 8/2010 | Lahann et al. | |
| 7,947,772 B2 | 5/2011 | Lahann et al. | |
| 8,241,651 B2 | 8/2012 | Lahann | |
| 9,415,392 B2 | 8/2016 | Ismagilov et al. | |
| 10,005,058 B2 | 6/2018 | Swager et al. | |
| 10,060,913 B2 * | 8/2018 | Swager | G01N 33/54366 |
| 10,252,231 B2 | 4/2019 | Swager et al. | |
| 11,119,098 B2 * | 9/2021 | Swager | G01N 21/77 |
| 11,229,892 B2 * | 1/2022 | Swager | C08L 35/02 |
| 2002/0040065 A1 | 4/2002 | Scher et al. | |
| 2002/0090608 A1 | 7/2002 | Palese et al. | |
| 2004/0069857 A1 | 4/2004 | Leblans et al. | |
| 2004/0176479 A1 | 9/2004 | Scher et al. | |
| 2005/0145829 A1 * | 7/2005 | Leyrer | C09K 19/04 252/299.01 |
| 2006/0154234 A1 | 7/2006 | Winther et al. | |
| 2006/0201390 A1 | 9/2006 | Lahann et al. | |
| 2007/0105972 A1 | 5/2007 | Doyle et al. | |
| 2007/0237800 A1 | 10/2007 | Lahann et al. | |
| 2008/0234394 A1 | 9/2008 | Hong et al. | |
| 2008/0242774 A1 | 10/2008 | Lahann et al. | |

(Continued)

FOREIGN PATENT DOCUMENTS

| | | |
|---|---|---|
| EP | 135352 A | 3/1985 |
| EP | 161328 A | 11/1985 |

(Continued)

OTHER PUBLICATIONS

Wang et al. Thermally reconfigurable Janus droplets with nematic liquid crystalline and isotropic perfluorocarbon oil compartments. Soft Matter, 2019, 15, 2580-2590. Published online Feb. 27, 2019. (Year: 2019).*
Definition of singularity. https://www.dictionary.com/browse/singularity. As viewed on May 29, 2024. (Year: 2024).*
U.S. Appl. No. 16/284,722, filed Feb. 25, 2019, Swager et al.
U.S. Appl. No. 16/113,520, filed Aug. 27, 2018, Swager et al.
U.S. Appl. No. 17/545,979, filed Dec. 8, 2021, Swager et al.
International Search Report and Written Opinion mailed Jan. 22, 2016 for Application No. PCT/US2015/058268.
International Preliminary Report on Patentability mailed May 11, 2017 for Application No. PCT/US2015/058268.

(Continued)

*Primary Examiner* — Stephen E Rieth
(74) *Attorney, Agent, or Firm* — Wolf, Greenfield & Sacks, P.C.

(57) ABSTRACT

Articles (e.g., a colloid) and methods for providing complex colloids comprising a hydrocarbon phase (e.g., a hydrocarbon phase comprising a liquid crystal) and a fluorocarbon phase are generally described. In some embodiments, the hydrocarbon phase and the fluorocarbon phase are distinct.

20 Claims, 82 Drawing Sheets

(56) References Cited

U.S. PATENT DOCUMENTS

| | | | |
|---|---|---|---|
| 2009/0232856 | A1 | 9/2009 | Patel |
| 2009/0306311 | A1 | 12/2009 | Reed |
| 2010/0062525 | A1 | 3/2010 | Abbott et al. |
| 2010/0069726 | A1 | 3/2010 | Levinson |
| 2010/0097687 | A1 | 4/2010 | Lipovetskaya et al. |
| 2010/0099048 | A1 | 4/2010 | Thomas et al. |
| 2011/0003401 | A1 | 1/2011 | Oscarsson et al. |
| 2011/0104777 | A1 | 5/2011 | Marquez et al. |
| 2011/0195394 | A1 | 8/2011 | Selinfreund et al. |
| 2011/0195421 | A1 | 8/2011 | Selinfreund et al. |
| 2011/0196085 | A1 | 8/2011 | Selinfreund et al. |
| 2011/0223590 | A1 | 9/2011 | Chiou et al. |
| 2012/0028342 | A1 | 2/2012 | Ismagilov et al. |
| 2012/0045748 | A1 | 2/2012 | Willson et al. |
| 2012/0248020 | A1 | 10/2012 | Granick et al. |
| 2012/0288852 | A1 | 11/2012 | Willson et al. |
| 2012/0319043 | A1 | 12/2012 | Stepien et al. |
| 2012/0328654 | A1 | 12/2012 | Huang et al. |
| 2014/0016177 | A1 | 1/2014 | Aizenberg et al. |
| 2014/0227684 | A1 | 8/2014 | Hindson et al. |
| 2014/0323330 | A1 | 10/2014 | Bergo |
| 2014/0350168 | A1 | 11/2014 | Bormashenko |
| 2015/0238636 | A1 | 8/2015 | Homyk et al. |
| 2016/0114325 | A1 | 4/2016 | Tang et al. |
| 2016/0151753 | A1 | 6/2016 | Swager et al. |
| 2016/0151756 | A1 | 6/2016 | Swager et al. |
| 2016/0193602 | A1 | 7/2016 | Tsai et al. |
| 2016/0235670 | A1 | 8/2016 | Mason et al. |
| 2017/0368865 | A1 | 12/2017 | Macpherson et al. |
| 2017/0371151 | A1 | 12/2017 | Brassard et al. |
| 2018/0080927 | A1* | 3/2018 | Swager .................. G01N 21/77 |
| 2019/0170736 | A1* | 6/2019 | Swager .............. G01N 33/5432 |
| 2019/0170737 | A1 | 6/2019 | Swager et al. |
| 2019/0184356 | A1 | 6/2019 | Swager et al. |
| 2019/0212333 | A1 | 7/2019 | Swager et al. |
| 2020/0056996 | A1* | 2/2020 | Zarzar ................ G01N 21/6452 |
| 2020/0166503 | A1 | 5/2020 | Swager et al. |
| 2021/0080456 | A1 | 3/2021 | Swager et al. |
| 2022/0205989 | A1 | 6/2022 | Swager et al. |

FOREIGN PATENT DOCUMENTS

| | | | |
|---|---|---|---|
| EP | 323909 | A | 7/1989 |
| EP | 1365240 | A2 | 11/2003 |
| JP | H05-99926 | A | 4/1993 |
| JP | 2013-518167 | A | 5/2013 |
| WO | WO 92/14154 | A1 | 8/1992 |
| WO | WO 1992/17179 | A1 | 10/1992 |
| WO | WO 1995/31500 | A2 | 11/1995 |
| WO | WO 2004/063707 | A2 | 7/2004 |
| WO | WO 2008/066463 | A1 | 6/2008 |
| WO | WO 2009/061372 | A1 | 5/2009 |
| WO | WO 2009/101113 | A2 | 8/2009 |
| WO | WO 2009/151390 | A1 | 12/2009 |
| WO | WO 2010/092333 | A1 | 8/2010 |
| WO | WO 2011/093733 | A1 | 8/2011 |
| WO | 2013/059294 | A1 | 4/2013 |
| WO | WO 2015/051179 | A1 | 4/2015 |
| WO | 2016/103226 | A2 | 6/2016 |

OTHER PUBLICATIONS

Extended European Search Report mailed Jun. 11, 2018 for Application No. EP 15855674.6.

International Search Report and Written Opinion mailed Jan. 22, 2016 for Application No. PCT/US2015/058286.

International Preliminary Report on Patentability mailed May 11, 2017 for Application No. PCT/US2015/058286.

International Search Report and Written Opinion mailed Nov. 30, 2017 for Application No. PCT/US2017/052209.

International Preliminary Report on Patentability mailed Mar. 28, 2019 for Application No. PCT/US2017/052209.

[No Author Listed], Definition of Associate. Retrieved from https://www.vocabulary.com/associate. Accessed on Apr. 22, 2020. 4 pages.

Alino et al., Liquid crystal droplets as a hosting and sensing platform for developing immunoassays. Langmuir. Aug. 2011;27:11784-9.

Augustin et al., Nano- and micro-structured assemblies for encapsulation of food ingredients. Chem Soc Rev. Apr. 2009;38(4):902-12. doi: 10.1039/b801739p. Epub Dec. 4, 2008.

Bedford et al., Solubilities and vol. Changes Attending Mixing for the System: Perfluoro- n-hexane-n-Hexane. J. Am. Chem. Soc., 1958, 80(2):282-285.

Berger et al., Stimuli-responsive bicomponent polymer Janus particles by “grafting from”/“grafting to” approaches. Macromolecules. 2008;41:9669-76. Epub Nov. 21, 2008.

Besnard et al., Multiple emulsions controlled by stimuli-responsive polymers. Adv Mater. May 28, 2013;25(20):2844-8. doi: 10.1002/adma.201204496. Epub Mar. 11, 2013.

Brown et al., Stimuli-responsive surfactants. Soft Matter 2013; 9:2365-2374.

Chakravarti et al., Liquid membrane multiple emulsion process of chromium(VI) separation from waste waters. Colloid Surface A 1995; 103:59-71.

Chen et al., Janus particles templated from double emulsion droplets generated using microfluidics. Langmuir. 2009;25(8):4320-3. Epub Mar. 18, 2009.

Chen et al., Photoresponsive Monodisperse Cholesteric Liquid Crystalline Microshells for Tunable Omnidirectional Lasing Enabled by a Visible Light-Driven Chiral Molecular Switch. Adv Op Mat 2014; 2(9): 845-8.

Chevallier et al., Photofoams: remote control of foam destabilization by exposure to light using an azobenzene surfactant. Langmuir. Feb. 7, 2012;28(5):2308-12. doi: 10.1021/la204200z. Epub Jan. 27, 2012.

Choi et al., Microfluidic Design of Complex Emulsions. ChemPhysChem 2014; 15: 21-290.

Choi et al., One step formation of controllable complex emulsions: from functional particles to simultaneous encapsulation of hydrophilic and hydrophobic agents into desired position. Adv mater. 2013; 6 pages.

Choi et al., Patterned fluorescent particles as nanoprobes for the investigation of molecular interactions. Nano Letters. 2003;3(8):995-1000. Epub Jul. 11, 2003.

De La Fuente et al., Exploring the efficiency of gallic acid-based dendrimers and their block copolymers with PEG as gene carriers. Nanomed. 2012;7(11):1667-81. Epub Jul. 20, 2012.

Dominguez et al., Modelling and understanding of the vapour-liquid and liquid-liquid interfacial properties for the binary mixture of n-heptane and perfluoro-n-hexane. J. Mol. Liq. 2013; 185:36-43.

Engel et al., Insulin: intestinal absorption as water-in-oil-in-water emulsions. Nature. Aug. 24, 1968;219(5156):856-7.

Gao et al., Double Emulsion Templated Microcapsules with Single Hollow Cavities and Thickness-Controllable Shells. Langmuir, 2009, 25(6): 3832-3838.

Ge et al., Droplet topology control of Janus emulsion prepared in one-step high energy mixing. Soft Matter. 2014;10:4498-505. Epub Apr. 8, 2014.

Gladysz et al., Structural, physical, and chemical properties of fluorous compounds. Top Curr Chem. 2012;308:1-23. doi: 10.1007/128_2011_282.

Gresham et al., Use of a sustained-release multiple emulsion to extend the period of radio protection conferred by cysteamine. Nature. Nov. 19, 1971;234(5325):149-50.

Guzowski et al., The structure and stability of multiple micro-droplets. Soft Matter 2012; 8: 7269-7278.

Haase et al., Tailoring of high-order multiple emulsions by the liquid-liquid phase separation of ternary mixtures. Angew Chem Int Ed. 2014;53:1-6.

Han et al., Retroreflective Janus microparticle as a nonspectroscopic optical immunosensing probe. ACS Appl Mater & Interfaces. May 4, 2016;8(17):10767-74.

Kaufmann et al., “Sandwich” microcontact printing as a mild route towards monodisperse Janus particles with tailored bifunctionality. Adv Mater. 2011;23:79-83; Supporting Information pp. 1-8.

(56) References Cited

OTHER PUBLICATIONS

Kaufmann et al., Bifunctional Janus beads made by "sandwich" microcontact printing using click chemistry. J Mater Chem. 2012;22:6190-9. Epub Feb. 17, 2012. Electronic suppl info pp. 1-9.
Kim et al., Fabrication of monodisperse gel shells and functional microgels in microfluidic devices. Angew Chem Int Ed Engl. 2007;46(11):1819-22.
Kumar et al., Multiple emulsions: a review. Int J Rec Adv Pharm Rsch. Jan. 2012; 2(1):9-19.
Lemal, Perspective on fluorocarbon chemistry. J Org Chem. Jan. 9, 2004;69(1):1-11.
Li et al., Synthesis of biofunctional Janus particles. Macromol Rapid Comm. 2015;36:1200-4.
Lone et al., Fabrication of polymeric Janus particles by droplet microfluidics. RSC Adv. 2014 4: 13322-13333.
McClain et al., Interfacial roughness in a near-critical binary fluid mixture: X-ray reflectivity and near-specular diffuse scattering. Eur. Phys. J. B. 1999; 10: 45-52.
McClements et al., Factors that affect the rate of oil exchange between oil-in-water emulsion droplets stabilized by a nonionic surfactant: Droplet size, surfactant concentration, and ionic strength. J. Phys. Chem. Jun. 1993; 97(28): 7304-08. doi: 10.1021/j100130a030.
Mukerjee et al., Adsorption of fluorocarbon and hydrocarbon surfactants to air-water, hexane-water and perfluorohexane-water interfaces. Relative affinities and fluorocarbon-hydrocarbon nonideality effects. J. Phys. Chem., 1981, 85(15): 2298-2303.
Nie et al., Janus and ternary particles generated by microfluidic synthesis: design, synthesis, and self-assembly. J Am Chem Soc. Jul. 26, 2006;128(29):9408-12.
Nisisako et al., Synthesis of monodisperse bicolored Janus particles with electrical anisotropy using a microfluidic co-flow system. Adv Mater. 2006;18:1152-6.
Niu et al., Optical biosensor based on liquid crystal droplets for detection of cholic acid. Optics Commun. 2016;381:286-91.
Patravale et al., Novel cosmetic delivery systems: an application update. Int J Cosmet Sci. Feb. 2008;30(1):19-33. doi: 10.1111/j.1468-2494.2008.00416.x.
Perro et al., Design and synthesis of Janus micro- and nanoparticles. J Mater Chem. 2005; 15:3745-60. Epub Jul. 25, 2005.
Riess, Overview of progress in the fluorocarbon approach to in vivo oxygen delivery. Biomater Artif Cells Immobilization Biotechnol. 1992;20(2-4):183-202.
Roh et al., Biphasic Janus particles with nanoscale anisotropy. Nat Mater. Oct. 2005;4:759-63. Epub Sep. 25, 2005.
Schutt et al., Injectable microbubbles as contrast agents for diagnostic ultrasound imaging: the key role of perfluorochemicals. Angew Chem Int Ed Engl. Jul. 21, 2003;42(28):3218-35.
Shah et al., Designer emulsions using microfluidics. Materials Today, 2011; 11: 18-27.
Shah et al., Janus Supraparticles by Induced Phase Separation of Nanoparticles in Droplets. Adv. Mater. 2009; 21: 1949-1953. doi: 10.1002/adma.200803115.
Shum et al., Droplet microfluidics for fabrication of non-spherical particles. Macromol Rapid Commun. Jan. 18, 2010;31(2):108-18. doi: 10.1002/marc.200900590. Epub Nov. 24, 2009.
Song et al., Monodisperse w/w/w/ double emulsion induced by phase separation. Langmuir. 2012;28:12054-12059.
Tanaka et al., Dual stimuli-responsive "mushroom-like" Janus polymer particles as particulate surfactants. Langmuir. Jul. 20, 2010;26(14):11732-6. doi: 10.1021/la101237c.
Tu et al., One-step encapsulation and triggered release based on Janus particle-stabilized multiple emulsions. Chem Commun (Camb). Dec. 21, 2014;50(98):15549-52. doi: 10.1039/c4cc07854c. Epub Oct. 30, 2014.
Utada et al., Monodisperse double emulsions generated from a microcapillary device. Science. Apr. 22, 2005;308(5721):537-41.
Walther et al., Janus particles. Soft Matter. 2008;4:663-8. Epub Feb. 26, 2008.
Wong et al., Bioinspired self-repairing slippery surfaces with pressure-stable omniphobicity. Nature. Sep. 21, 2011;477(7365):443-7. doi: 10.1038/nature10447.
Wu et al., Bioinspired nanocorals with decoupled cellular targeting and sensing functionality. Small. 2010;6(4):503-7.
Yusa et al., Fluorescence Studies of pH-Responsive Unimolecular Micelles Formed from Amphiphilic Polysulfonates Possessing Long-Chain Alkyl Carboxyl Pendants. Macromolecules. 2002; 35(27): 10182-88. doi: 10.1021/ma0212947. Epub Nov. 27, 2002.
Zhang et al., Interfacial bioconjugation on emulsion droplet for biosensors. Bioorg Med Chem. Oct. 15, 2018;26(19):5307-13. Author manuscript. 20 pages.
Zhang et al., Janus emulsions for the detection of bacteria. ACS Central Sci. Apr. 26, 2017;3(4):309-13.
Zhao et al., Microfluidic mass-transfer control for the simple formation of complex multiple emulsions. Angew Chem Int Ed. 2009;48:7208-11.
[No Author Listed], Definition of Fluidic. Retrieved from https://www.merriam-webster.com/dictionary/fluidic. Last accessed on Apr. 14, 2021. 10 pages.
Axenov et al., Thermotropic Ionic Liquid Crystals. Materials. 2011;4:206-59. Epub Jan. 14, 2011.
Belmonte et al., Patterned Full-Color Reflective Coatings Based on Photonic Cholesteric Liquid-Crystalline Particles. ACS Appl Mater Interfaces. Apr. 17, 2019;11(15):14376-14382. doi: 10.1021/acsami.9b02680. Epub Apr. 8, 2019.
Bijlard et al., Functional Colloidal Stabilization. Advanced Materials Interfaces. Jan. 2019;4(1):1600443. Epub Nov. 8, 2016. 31 pages.
Brake et al., Biomolecular interactions at phospholipid-decorated surfaces of liquid crystals. Science. Dec. 19, 2003;302(5653):2094-7. doi: 10.1126/science.1091749.
Braun et al., Functional liquid crystalline particles and beyond. Liquid Crystals. 2019;46(13-14):2023-41.
Broer et al., Functional organic materials based on polymerized liquid-crystal monomers: supramolecular hydrogen-bonded systems. Angew Chem Int Ed Engl. Jul. 16, 2012;51(29):7102-9. doi: 10.1002/anie.201200883. Epub May 15, 2012.
Brunsveld et al., Hierarchical Growth of Chiral Self-Assembled Structures in Protic Media. J. Am. Chem. Soc. 2000;122(26):6175-82. Epub Jun. 17, 2000.
Cipparrone et al., Chiral self-assembled solid microspheres: a novel multifunctional microphotonic device. Adv Mater. Dec. 22, 2011;23(48):5773-8. doi: 10.1002/adma.201102828. Epub Nov. 15, 2011.
Concellón et al., Dynamic Complex Liquid Crystal Emulsions. J. Am. Chem. Soc. 2019;141(45):18246-55. Epub Nov. 1, 2019.
Craig et al., Effect of Spacer Length on the Thermal Properties of Side-Chain Liquid Crystal Polymethacrylates. 2. Synthesis and Characterization of the Poly[.omega.-(4'-cyanobiphenyl-4-yloxy)alkyl methacrylate]s. Macromolecules. 1995;28(10):3617-24. Epub May 1, 1995.
Eremin et al., Azodendrimers as a photoactive interface for liquid crystals. Liquid Crystals. 2018;45(13-15):2121-31. Epub Aug. 17, 2018.
Fleischmann et al., One-piece micropumps from liquid crystalline core-shell particles. Nat Commun. 2012;3:1178. doi: 10.1038/ncomms2193. Epub Nov. 6, 2012. 8 pages.
Forth et al., Building Reconfigurable Devices Using Complex Liquid-Fluid Interfaces. Advanced Materials. May 2019;31(18):1806370. Epub Mar. 4, 2019. 39 pages.
Ge et al., Recent studies of Janus emulsions prepared by one-step vibrational mixing. Current Opinion in Colloid & Interface Science. Oct. 2016;25:58-66.
He et al., Interfacial Polymerization on Dynamic Complex Colloids: Creating Stabilized Janus Droplets. ACS Applied Materials & Interfaces. 2017;9(8):7804-11. Epub Feb. 15, 2017.
Heinze et al., Microfluidic immunosensor for rapid and sensitive detection of bovine viral diarrhea virus. Sensors and Actuators B. 2009;138:491-6.
Hessberger et al., Interfacial Self-Assembly of Amphiphilic Dual Temperature Responsive Actuating Janus Particles. Adv Funct Mater. 2018;28(21):1800629. 10 pages.

(56) References Cited

OTHER PUBLICATIONS

Jampani et al., Micrometer-Scale Porous Buckling Shell Actuators Based on Liquid Crystal Networks. Advanced Functional Materials. 2018;28(31):1801209. Epub Jun. 5, 2018. 9 pages.
Jeong et al., Liquid crystal Janus emulsion droplets: preparation, tumbling, and swimming. Soft Matter. Sep. 14, 2015;11(34):6747-54. doi: 10.1039/c5sm01053e. Epub Jul. 14, 2015.
Joyce, Fluidics—Basic Components and Applications. U.S. Army Electronics Research and Development Command. Harry Diamond Laboratories. Adelphi, MD. Aug. 1983. 24 pages.
Kang et al., Amplified Photon Upconversion by Photonic Shell of Cholesteric Liquid Crystals. J Am Chem Soc. Apr. 26, 2017;139(16):5708-5711. doi: 10.1021/jacs.7b01981. Epub Apr. 17, 2017.
Kato et al., Functional Liquid Crystals towards the Next Generation of Materials. Angew Chem Int Ed Engl. Apr. 9, 2018;57(16):4355-4371. doi: 10.1002/anie.201711163. Epub Mar. 13, 2018.
Lin et al., Endotoxin-Induced Structural Transformations in Liquid Crystalline Droplets. Science. Jun. 10, 2011; 332(6035): 1297-1300. Epub May 11, 2011. Author manuscript provided. 8 pages.
Lin et al., Morphology-Dependent Luminescence in Complex Liquid Colloids. J Am Chem Soc. Mar. 6, 2019;141(9):3802-3806. doi: 10.1021/jacs.8b13215. Epub Feb. 20, 2019. Author manuscript provided. 16 pages.
McClements et al., Structured emulsion-based delivery systems: controlling the digestion and release of lipophilic food components. Adv Colloid Interface Sci. Sep. 15, 2010;159(2):213- 28. doi: 10.1016/j.cis.2010.06.010. Epub Jul. 3, 2010.
Miller et al., Design of Functional Materials based on Liquid Crystalline Droplets. Chem Mater. Jan. 14, 2014;26(1):496-506. doi: 10.1021/cm4025028. Author manuscript provided. 26 pages.
Miniewicz et al., Photochromic and nonlinear optical properties of azo-functionalized POSS nanoparticles dispersed in nematic liquid crystals. Journal of Materials C. 2014;2:432-40. Epub Oct. 30, 2013.
Mondiot et al., Liquid crystal-based emulsions for synthesis of spherical and non-spherical particles with chemical patches. J Am Chem Soc. Jul. 10, 2013;135(27):9972-5. doi: 10.1021/ja4022182. Epub Apr. 19, 2013. Author manuscript provided. 10 pages.
Nagelberg et al., Reconfigurable and responsive droplet-based compound micro-lenses. Nat Commun. Mar. 7, 2017;8:14673. doi: 10.1038/ncomms14673. Epub Mar. 7, 2017. 9 pages.
Ohm et al., A continuous flow synthesis of micrometer-sized actuators from liquid crystalline elastomers. Adv Mater. Dec. 18, 2009;21(47):4859-62. doi: 10.1002/adma.200901522.
Schwartz et al., Cholesteric Liquid Crystal Shells as Enabling Material for Information-Rich Design and Architecture. Adv Mater. Jul. 2018;30(30):e1707382. doi: 10.1002/adma.201707382. Epub May 14, 2018. 19 pages.
Sivakumar et al., Liquid Crystal Emulsions as the Basis of Biological Sensors for the Optical Detection of Bacteria and Viruses. Advanced Functional Materials. 2009;19(14):2260-5. Epub Jul. 16, 2009.
Skarabot et al., Hierarchical self-assembly of nematic colloidal superstructures. Phys Rev E. Jun. 2008;77(6 Pt 1):061706. doi: 10.1103/PhysRevE.77.061706. Epub Jun. 12, 2008. 4 pages.
Tschierske, Development of structural complexity by liquid-crystal self-assembly. Angew Chem Int Ed Engl. Aug. 19, 2013;52(34):8828-78. doi: 10.1002/anie.201300872. Epub Aug. 9, 2013.
Van Der Asdonk et al., Liquid crystal templating as an approach to spatially and temporally organise soft matter. Chem Soc Rev. Oct. 2, 2017;46(19):5935-5949. doi: 10.1039/c7cs00029d.
Wang et al., Liquid crystals: emerging materials for use in real-time detection applications. Journal of Materials Chemistry C. 2015;3:9038-47. Epub Aug. 4, 2015. Author manuscript provided. 23 pages.
Wang et al., Thermally reconfigurable Janus droplets with nematic liquid crystalline and isotropic perfluorocarbon oil compartments. Soft Matter. Mar. 20, 2019;15(12):2580-2590. doi: 10.1039/c8sm02600a. Author manuscript provided. 12 pages.
Wang et al., Topological defects in liquid crystals as templates for molecular self-assembly. Nat Mater. Jan. 2016;15(1):106-12. doi: 10.1038/nmat4421. Epub Sep. 21, 2015.
Yang et al., Microfluidic synthesis of multifunctional Janus particles for biomedical applications. Lab Chip. Jun. 2, 20121;12(12):2097-102. doi: 10.1039/c2lc90046g. Epub May 14, 2012. Author manuscript provided. 14 pages.
Yi et al., Janus particles for biological imaging and sensing. Analyst. Jun. 21, 2016;141(12):3526-39. doi: 10.1039/c6an00325g. Epub Apr. 7, 2016. Author manuscript provided. 24 pages.
Yoshida et al., Structurally Controlled Bio-hybrid Materials Based on Unidirectional Association of Anisotropic Microparticles with Human Endothelial Cells. Adv Mater. Dec. 2009;21:4920-5.
Yuet et al., Multifunctional Superparamagnetic Janus Particles. Langmuir. Mar. 16, 2010;26(6):4281-7. doi: 10.1021/1a903348s. Epub Oct. 20, 2009.
Zarzar et al., Dynamically reconfigurable complex emulsions via tunable interfacial tensions. Nature. Feb. 26, 2015;518(7540):520-4. doi: 10.1038/nature14168. Author manuscript provided. 20 pages.
Zeininger et al., Rapid Detection of Salmonella enterica via Directional Emission from Carbohydrate-Functionalized Dynamic Double Emulsions. ACS Cent Sci. May 22, 2019; 5(5):789-795. Epub Apr. 23, 2019.
Zeininger et al., Waveguide-based chemo- and biosensors: complex emulsions for the detection of caffeine and proteins. Lab on a Chip. 2019;19:1327-31. Epub Mar. 21, 2019.
Zhang et al., Emulsion Agglutination Assay for the Detection of Protein-Protein Interactions: An Optical Sensor for Zika Virus. ACS Sens. Jan. 25, 2019;4(1):180-184. doi: 10.1021/acssensors.8b01202. Epub Jan. 9, 2019. Author manuscript provided. 12 pages.
Zhang et al., Fabrication of Janus droplets by evaporation driven liquid-liquid phase separation. Chemical Communications. 2016;52:5015-8. Epub Mar. 7, 2016.
Zhang et al., Janus Particle Synthesis, Assembly, and Application. Langmuir. 2017;33(28):6964-77. Epub Jul. 5, 2017.
Zhang et al., Toward Design Rules of Directional Janus Colloidal Assembly. Ann Rev Phys Chem. 2015;66:581-600. doi: 10.1146/annurev-physchem-040214-121241. Epub Feb. 4, 2015.
Zhang et al., Ultra-small droplet generation via volatile component evaporation. Lab Chip. Apr. 21, 2014;14(8):1395-400. doi: 10.1039/c31c51183a.
Anker et al., Magnetically modulated optical nanoprobes. Appl Phys Lett. 2003. 82(7): 1102-4.
Claessens et al., Highly Efficient Synthesis of Chloro- and Phenoxy-Substituted Subphthalocyanines. Jun. 26, 2003;2003(14):2547-51.
Erb et al., Towards holonomic control of Janus particles in optomagnetic traps. Adv Mater. Dec. 18, 2009;21(47):4825-9.
McNaughton et al., Compact sensor for measuring nonlinear rotational dynamics of driven magnetic microspheres with biomedical applications. J Magnet Magnet Materials. 2009; 321: 1648-52.
McNaughton et al., Single bacterial cell detection with nonlinear rotational frequency shifts of driven magnetic microspheres. Appl Phys Lett. 2007. 91: 224105.
Ong et al., Dynamic self-correcting nucleophilic aromatic substitution. Nat Chem. Sep. 3, 2018;10:1023-30.
Sun et al., Controlled production of size-tunable Janus droplets for submicron particle synthesis using an electrospray microfluidic chip. RSC Adv. 2016; 6: 12042-7.
Wang et al., Janus magneto-electric nanosphere dimers exhibiting unidirectional visible light scattering and strong electromagnetic field enhancement. ACS Nano. Jan. 27, 2015;9(1):436-48. doi: 10.1021/nn505606x. Epub Jan. 6, 2015.
Yin et al., Versatile bifunctional magnetic-fluorescent responsive Janus supraballs towards the flexible bead display. Adv Mater. Jul. 12, 2011;23(26):2915-9. doi: 10.1002/adma.201100203. Epub Apr. 26, 2011.
Yu et al., Simultaneous detection of pathogenic bacteria using agglutination test based on colored silica nanoparticles. Curr Pharm Biotechnol. 2015;16(8):716-23.
International Search Report and Written Opinion for International Application No. PCT/US2020/042599 dated Dec. 3, 2020.

(56) References Cited

OTHER PUBLICATIONS

International Preliminary Report on Patentability (Chapter 1) for International Application No. PCT/US2020/042599 dated Mar. 31, 2022.

* cited by examiner

0%

41.6%

CB-$R_F$

PCB-*b*-P$R_F$

CB-diTEG

CB-diR$_F$

PCB-*b*-PB(OH)$_2$

*Chiral nematic* (N*)

$$\lambda = n \cdot p \cdot cos\theta \quad (p = \frac{1}{HTP \cdot C})$$

5CB

CB15

(HTP = 7.1 μm$^{-1}$)

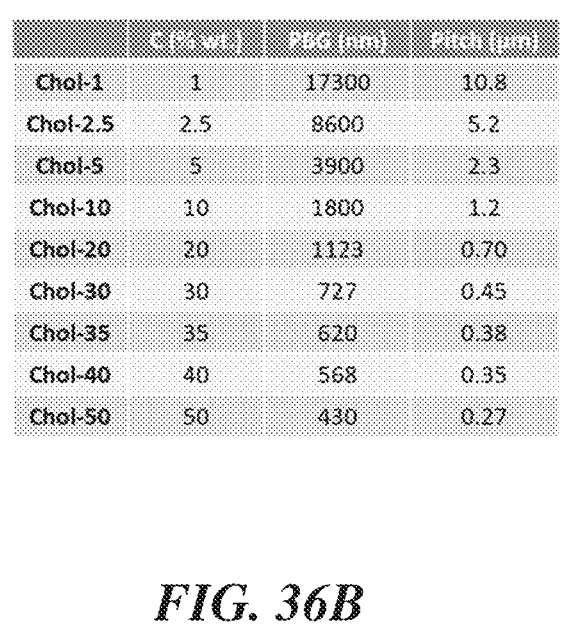

| | C (% wt.) | PBG (nm) | Pitch (μm) |
|---|---|---|---|
| **Chol-1** | 1 | 17300 | 10.8 |
| **Chol-2.5** | 2.5 | 8600 | 5.2 |
| **Chol-5** | 5 | 3900 | 2.3 |
| **Chol-10** | 10 | 1800 | 1.2 |
| **Chol-20** | 20 | 1123 | 0.70 |
| **Chol-30** | 30 | 727 | 0.45 |
| **Chol-35** | 35 | 620 | 0.38 |
| **Chol-40** | 40 | 568 | 0.35 |
| **Chol-50** | 50 | 430 | 0.27 |

*FIG. 36B*

Chol-10 (p ≈ 1 μm)

Chol-5 (p ≈ 2 µm)

Chol-2.5 (p ≈ 5 μm)

Chol-1 (p ≈ 11 μm)

1

2

COMPLEX LIQUID CRYSTAL DROPLETS

CROSS REFERENCE TO RELATED APPLICATIONS

This application claims priority under 35 U.S.C. § 119(e) to U.S. Provisional Application No. 62/925,756, filed Oct. 24, 2019, and entitled "COMPLEX LIQUID CRYSTAL DROPLETS," which is incorporated herein by reference in its entirety for all purposes.

This Application is also a continuation-in-part of U.S. application Ser. No. 16/201,961 filed Nov. 27, 2018, entitled "SYSTEMS INCLUDING JANUS DROPLETS," which is a continuation-in-part of U.S. application Ser. No. 16/113,520 filed Aug. 27, 2018, entitled "SYSTEMS INCLUDING JANUS DROPLETS," which is a continuation of U.S. application Ser. No. 15/269,543, filed Sep. 19, 2016, entitled "SYSTEMS INCLUDING JANUS DROPLETS," and this application is a continuation-in-part of U.S. application Ser. No. 14/929,117, filed Oct. 30, 2015, entitled "COMPOSITIONS AND METHODS FOR FORMING EMULSIONS," which claims priority under 35 U.S.C. § 119(e) to U.S. Provisional Application Ser. No. 62/073,896, filed Oct. 31, 2014, each of which is incorporated herein by reference in their entirety.

GOVERNMENT SUPPORT

This invention was made with government support under N00014-18-1-2878 awarded by the Office of Naval Research. The government has certain rights in this invention.

FIELD OF THE INVENTION

The present invention generally relates to systems and methods including Janus droplets. Articles and methods for providing colloids comprising liquid crystals are also generally described.

BACKGROUND

Emulsification is a powerful age-old technique for mixing and dispersing immiscible components within a continuous liquid phase. Consequently, emulsions are central components of medicine, food, and performance materials. Complex emulsions, including multiple emulsions and Janus droplets, are of increasing importance in pharmaceuticals and medical diagnostics, in the fabrication of microdroplets and capsules for food, in chemical separations, for cosmetics, for dynamic optics, and chemical separations. However, quantitative detections of analytes with high sensitivity and selectivity using Janus droplets have yet to be realized. Accordingly, improved systems and methods are needed.

SUMMARY OF THE INVENTION

The present invention provides systems and methods including Janus droplets.

In one aspect, an article comprising a colloid is described. The article may comprise an aqueous phase, a surfactant disposed within the aqueous phase, and a droplet surrounded by the aqueous phase, wherein the droplet comprises a hydrocarbon phase and fluorocarbon phase, and wherein the hydrocarbon phase comprises a liquid crystal.

In one aspect, a method for preparing a colloid is described, the method comprising suspending a droplet comprising a hydrocarbon phase and a fluorocarbon phase in an aqueous phase, wherein the hydrocarbon phase comprises a liquid crystal, dissolving a non-ionic surfactant in the aqueous phase, emulsifying the aqueous phase, the hydrocarbon phase, the fluorocarbon phase with an emulsifying agent, and evaporating the emulsifying agent.

In another aspect, emulsions are provided. In some embodiments, the emulsion comprises an outer phase, a plurality of droplets dispersed within the outer phase, wherein the plurality of droplets comprise two or more components, wherein the two or more components are substantially miscible at a first temperature, and wherein the two or more components are substantially immiscible at a second temperature.

In another aspect, methods for forming an emulsion are provided. In some embodiments, the method comprises adjusting the temperature of a fluid to a first temperature, wherein the fluid comprises a first phase and a second phase substantially immiscible in the first phase, wherein the second phase comprises two or more components that are substantially miscible with each other, emulsifying the fluid, and adjusting the temperature of the fluid to a second temperature, such that the two or more components become substantially immiscible.

In another aspect, systems are provided. In some embodiments, the system comprises a plurality of Janus droplets associated with binding moieties to an analyte, the binding moiety and analyte selected such that when the analyte binds to the binding moiety at least a portion of the plurality of Janus droplets are changed in orientation sufficient to change electromagnetic radiation interacting with the plurality of Janus droplets in a detectable manner.

In some embodiments, the system comprises a plurality of Janus droplets associated with a plurality of binding moieties to an analyte and a detector positioned relative to the plurality of Janus droplets such that when sufficient numbers of the binding moieties bind to analyte at least a portion of the plurality of Janus droplets are changed in orientation sufficient to change electromagnetic radiation interacting with the Janus droplets in a manner determinable by the detector.

In certain embodiments, a hydrocarbon phase and/or a fluorocarbon phase comprises magnetic particles (e.g., $Fe_3O_4$ nanoparticles).

In certain embodiments, upon binding to the binding moieties, at least a portion of the plurality of Janus droplets agglutinate.

In certain embodiments, prior to binding to the binding moieties, the plurality of Janus droplets are oriented such that at least a portion of interfaces between a first phase and a second phase within each Janus droplet are aligned parallel with respect to one another.

In certain embodiments, prior to the analyte binding to the binding moieties, the plurality of Janus droplets are bound to a surface.

In certain embodiments, upon binding of the analyte to the binding moieties, at least a portion of the plurality of Janus droplets unbind from the surface.

In certain embodiments, the system comprises a source of external energy applicable to the composition to generate a determinable signal and a detector positioned to detect the signal.

In certain embodiments, the signal comprises electromagnetic radiation.

In certain embodiments, upon exposure of the article to a chemical or biological analyte, the system generates the determinable signal.

In another aspect, methods are provided. In some embodiments, the method comprises allowing an analyte to bind to binding moieties associated with a plurality of Janus droplets and determining a change in electromagnetic radiation interacting with the plurality of Janus droplets due at least in part to the binding of the analyte to the binding moieties.

In some embodiments, the method comprises exposing, to an article comprising an outer phase and a plurality of Janus droplets dispersed within the outer phase, a chemical or biological analyte, wherein the chemical or biological analyte, if present, interacts with at least a portion of the article such that at least a portion of the plurality of Janus droplets change orientation thereby producing a detectable change in an optical property of the article and determining the detectable change.

In some embodiments, the method comprises exposing, to an article comprising an outer phase and a plurality of Janus droplets dispersed within the outer phase, a chemical or biological analyte, wherein the chemical or biological analyte, if present, interacts with at least a portion of the article such that at least a portion of the plurality of Janus droplets change orientation thereby changing the optical transmission of the article.

In certain embodiments, the plurality of Janus droplets comprise one or more amphiphilic compounds including at least one binding moiety.

In certain embodiments, interacting with at least a portion of the article comprises binding of the chemical or biological analyte to the at least one binding moiety.

In certain embodiments, prior to exposing the article to a chemical or biological analyte, at least a portion of the plurality of Janus droplets are oriented such that at least a portion of interfaces between a first phase and a second phase within each Janus droplet are aligned parallel with respect to one another.

In certain embodiments, substantially all of the interfaces between a first phase and a second phase within each Janus droplet are aligned parallel with respect to one another.

In certain embodiments, upon exposing the article to a chemical or biological analyte, at least a portion of the plurality of Janus droplets agglutinate.

In certain embodiments, upon exposing the article to a chemical or biological analyte, at least a portion of the plurality of Janus droplets are oriented such that at least a portion of interfaces between a first phase and a second phase within each Janus droplet are not aligned parallel with respect to one another.

In certain embodiments, at least a portion of the plurality of Janus droplets are bound to a surface of the article via the binding moiety.

In certain embodiments, upon exposing the article to a chemical or biological analyte, at least a portion of the plurality of Janus droplets unbind from the surface.

In yet another aspect, articles are provided. In some embodiments, the article comprises an outer phase and a plurality of Janus droplets dispersed within the outer phase, wherein at least a portion of the plurality of Janus droplets comprise an amphiphilic compound including at least one binding moiety.

In certain embodiments, the plurality of Janus droplets is oriented such that at least a portion of interfaces between a first phase and a second phase within each Janus droplet are aligned parallel with respect to one another.

In certain embodiments, the at least one binding moiety is capable of binding with a chemical or biological analyte.

In certain embodiments, upon binding of the at least one binding moiety with a chemical or biological analyte, at least a portion of the plurality of Janus droplets change orientation.

In certain embodiments, the plurality of Janus droplets are substantively transmissive to electromagnetic radiation.

In certain embodiments, upon binding of the at least one binding moiety with a chemical or biological analyte, the plurality of Janus droplets decrease in optical transmission.

In some embodiments, the article comprises a surface, an outer phase deposited on at least a portion of the surface, and a plurality of Janus droplets dispersed within the outer phase, wherein at least a portion of the plurality of Janus droplets comprise an amphiphilic compound including at least one binding moiety, and wherein at least a portion of the plurality of Janus droplets are bound to the surface via the binding moiety.

In certain embodiments, at least a portion of the plurality of Janus droplets are oriented such that an interface between a first phase and a second phase within each Janus droplet are not aligned parallel to the surface.

In certain embodiments, upon exposure of the plurality of Janus droplets to a biological or chemical analyte, at least a portion of Janus droplets unbind from the surface.

In certain embodiments, upon exposure of the plurality of Janus droplets to a biological or chemical analyte, at least a portion of Janus droplets change orientation.

In certain embodiments, the article is substantively visible-light transmissive after exposure to the plurality of Janus droplets to the biological or chemical analyte.

In certain embodiments, upon exposure of the plurality of Janus droplets to a chemical or biological analyte, the plurality of Janus droplets increase in optical transmission.

In certain embodiments, each Janus droplet comprises a first phase and a second phase, immiscible with the first phase.

In certain embodiments, the outer phase is an aqueous phase.

In certain embodiments, the first phase comprises a hydrocarbon, a fluorocarbon, a silicone, a liquid crystal, an ionic liquid, a polymer, combinations thereof, and/or derivatives thereof.

In certain embodiments, the second phase comprises a hydrocarbon, a fluorocarbon, a silicone, a liquid crystal, an ionic liquid, a polymer, combinations thereof, and/or derivatives thereof, such that the second phase is immiscible with the first phase.

In certain embodiments, the amphiphilic compound is selected from the group consisting of: ionic surfactants, non-ionic surfactants, zwitterionic surfactants, polymers, proteins, DNA, RNA, acids, carbohydrates, saccharides, enzymes, chromophores, lipids, graphene oxide, combinations thereof, and derivatives thereof.

In certain embodiments, an interface between the outer phase and the plurality of Janus droplets comprises the amphiphilic compound.

In certain embodiments, the analyte comprises a biological compound, a drug, a macromolecule, a salt, an electrolyte, an enzyme, an acid, a nucleic acid, a carbohydrate, a peptide, a protein, a phosphate, a sulfonate, a virus, a pathogen, an oxidant, a reductant, a toxin, a chemical warfare agent, an explosive, carbon dioxide, or combinations thereof.

In certain embodiments, the analyte is a single analyte.

In some embodiments, the system comprises a plurality of Janus droplets comprising a first phase and a second phase and an amphiphilic compound associated with the first phase and capable of interacting with a biological analyte, wherein the amphiphilic compound does not associate with the second phase, and In certain embodiments, the amphiphilic compound comprises gallic acid or a derivative thereof.

In certain embodiments, wherein upon binding to the biological analyte, at least a portion of the plurality of Janus droplets agglutinate.

In certain embodiments, wherein, prior to binding to the biological analyte, the plurality of Janus droplets are oriented such that at least a portion of interfaces between a first phase and a second phase within each Janus droplet are aligned parallel with respect to one another.

In some embodiments, the system comprises an outer phase and a plurality of droplets dispersed within the outer phase, wherein at least a portion of the plurality of droplets comprise a first phase and a second phase, the first phase immiscible with the second phase and an amphiphilic compound associated with the first phase, the amphiphilic compound capable of binding with a biological analyte, wherein the plurality of droplets have a first configuration in which the amphiphilic compound is exposed to the outer phase, and wherein the plurality of droplets have a second configuration in which the amphiphilic compound is not exposed to the outer phase.

In some embodiments, the method comprises providing a colloid comprising an outer phase, a plurality of droplets dispersed within the outer phase, wherein at least a portion of the plurality of droplets comprise a first phase and a second phase, the first phase immiscible with the second phase, and an amphiphilic compound associated with the first phase, the amphiphilic compound capable of binding with a biological analyte, wherein the amphiphilic compound is not exposed to the outer phase, stimulating the colloid, such that the first phase and the second phase change arrangement and such that the amphiphilic compound is exposed to the outer phase and wherein the first phase and the second phase are immiscible with each other after changing arrangement.

In some embodiments, the method comprises allowing a biological analyte to bind to an amphiphilic compound associated with a plurality of Janus droplets and determining a change in electromagnetic radiation interacting with the plurality of Janus droplets due at least in part to the binding of the biological analyte to the amphiphilic compound.

In some embodiments, the method comprises exposing, to an article comprising an outer phase and a plurality of Janus droplets dispersed within the outer phase, a chemical or biological analyte, wherein the chemical or biological analyte, if present, interacts with an amphiphilic compound associated with a first phase of the Janus droplets such that at least a portion of the plurality of Janus droplets change orientation thereby producing a detectable change in an optical property of the article and determining the detectable change.

In certain embodiments, wherein interacting with at least a portion of the article comprises binding of the chemical or biological analyte to the amphiphilic compound.

In certain embodiments, wherein, prior to exposing the article to a chemical or biological analyte, at least a portion of the plurality of Janus droplets are oriented such that at least a portion of interfaces between a first phase and a second phase within each Janus droplet are aligned parallel with respect to one another.

In certain embodiments, wherein substantially all of the interfaces between a first phase and a second phase within each Janus droplet are aligned parallel with respect to one another.

In certain embodiments, wherein, upon exposing the article to a chemical or biological analyte, at least a portion of the plurality of Janus droplets agglutinate.

In certain embodiments, wherein, upon exposing the article to a chemical or biological analyte, at least a portion of the plurality of Janus droplets are oriented such that at least a portion of interfaces between a first phase and a second phase within each Janus droplet are not aligned parallel with respect to one another.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

(FIG. 15A) In situ formation of GA12-NHS at droplet interface and subsequent amine conjugation. (FIG. 15B) Pre-synthesized GA12-NHS was dissolved in the droplet hydrocarbon phase and located at the hydrocarbon-water interface after trifluoethanol diffuses out to the continuous phase, followed by interfacial amine conjugation. (FIG. 15C) Pre-synthesized GA16-MA for interfacial thiol conjugation. FL in the schemes indicates generic fluorophores.

(FIG. 16A) Confocal z-stack images of emulsion droplets containing GA16-MA after covalent dye functionalization, 10× magnification. (FIG. 16B) Confocal cross-section of the droplet containing GA16-MA after covalent dye functionalization, 20× magnification.

(FIG. 20A) Microscope image of Protein A functionalized droplets in Janus morphology. (FIG. 20B) Microscope image of droplet in F/H/W after IgG bind to protein A. (FIG. 20C) Confocal cross section image of droplets with IgG at the hydrocarbon-water interface, in F/H/W morphology.

(FIG. 21A) Zonyl forced deformation of emulsion droplet on the side under microscope. (FIG. 21B) Confocal z-stack images of deformed droplets showing covalent bond formation at the droplet interface.

FIG. 36B shows the chemical compositions, photonic band gap (PBG), and pitch for the different N* mixtures, according to one set of embodiments;

Figure 1A:
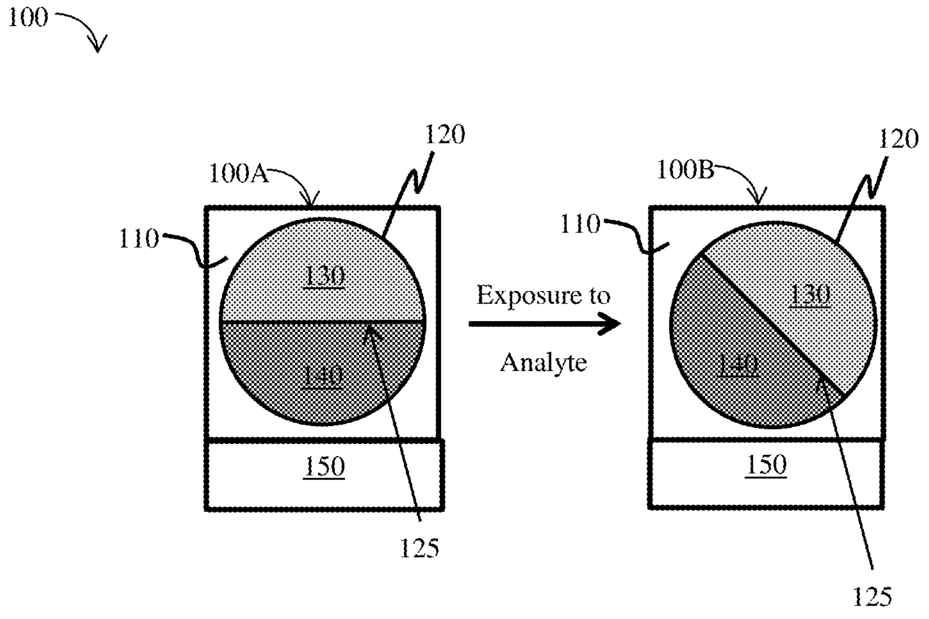
FIG. 1A illustrates a system including a Janus droplet, exposed to an analyte, according to one set of embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Articles (e.g., a colloid) and methods for providing complex colloids comprising a hydrocarbon phase (e.g., a hydrocarbon phase comprising a liquid crystal) and a fluorocarbon phase are generally described. In some embodiments, the hydrocarbon phase and the fluorocarbon phase are distinct.

In one embodiment, a colloid is described. The colloid may comprise an aqueous phase, a surfactant; a droplet, wherein the droplet comprises a hydrocarbon phase and fluorocarbon phase. The hydrocarbon phase may also comprise a liquid crystal. In some embodiments, a method for preparing a colloid is described, where the method comprises providing an aqueous phase, a hydrocarbon phase, and a fluorocarbon phase, wherein the hydrocarbon phase comprises a liquid crystal. The method may comprise providing a non-ionic surfactant and emulsifying the aqueous phase, the hydrocarbon phase, the fluorocarbon phase with an emulsifying agent. The method may also comprise evaporating the emulsifying agent. Some embodiments may include a compound of Formula (I), wherein formula (I) comprises

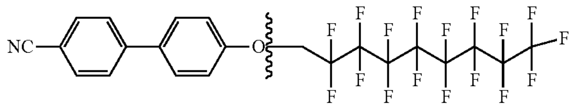

wherein, designates connection from an intervening chemical species. In some embodiments, the compound of Formula (I) is a surfactant as described herein.

Embodiments described herein may be useful in the detection of analytes. The systems and methods may allow for a relatively simple and rapid way for detecting analytes such as chemical and/or biological analytes and may be useful in numerous applications including sensing, food manufacturing, medical diagnostics, performance materials, dynamic lenses, water monitoring, environmental monitoring, detection of proteins, detection of DNA, among other applications. For example, the articles (e.g., colloids), systems and methods described herein may be used for determining the presence of a contaminant such as bacteria (e.g., detecting pathogenic bacteria in food and water samples which helps to prevent widespread infection, illness, and even death). Advantageously, the systems and methods described herein may not have the drawbacks in current detection technologies including, for example, relatively high costs, long enrichment steps and analysis times, and/or the need for extensive user training. Another advantageous feature provided by the systems and methods described herein includes fabrication in a relatively large scale. In some embodiments, the systems and methods may be used in conjunction with a detector including handheld detectors incorporated with, for example, smartphones (e.g., for the on-site detection of analytes such as pathogenic bacteria). For example, such systems could be used by the food industry to prevent extensive foodborne illnesses which may result in expensive medical treatment costs, lawsuits, government sanctions, product recalls, and/or tarnished long-term reputations. Articles comprising Janus droplets are also provided.

Advantageously, the systems and methods described herein may enable the functionalization (e.g., bioconjugation) on already formed droplets (e.g., having two or more internal phases) in an outer phase, without resulting in instability of the droplets. In some embodiments, the (bio) conjugation reaction may change the interfacial tension between two or more phases and, in some cases, may be used to change the configuration of a droplet as described herein. In some embodiments, an analyte such as a biological analyte binds to the conjugated droplet.

In some embodiments, the articles, systems, and methods comprise a plurality of Janus droplets. Janus droplets generally include two or more phases immiscible with one another and/or having distinct physical and/or chemical properties, within the droplet. In certain embodiments, when equal amounts of the two immiscible phases are present and the interfacial tensions are properly balanced, the Janus droplets will be spherical with each hemisphere of the sphere comprising one of the immiscible phases. In certain embodiments, the plurality of Janus droplets includes a first phase and a second phase immiscible with the first phase. In some embodiments, the plurality of Janus droplets may be dispersed within an outer phase (e.g., an aqueous phase). For example, in some embodiments, the system comprises an aqueous phase and a plurality of Janus droplets comprising a hydrocarbon and a fluorocarbon. In some cases, the plurality of Janus droplets may be associated a binding moiety (e.g., a binding moiety associated with the Janus droplets and/or a binding moiety present on a surfactant incorporated with the plurality of Janus droplets). In some embodiments, the binding moiety may bind with an analyte (e.g., a biological and/or chemical analyte) such that the orientation of at least a portion of the plurality of Janus droplets is changed. The change in orientation of a Janus droplet may result in a change in the interaction of electromagnetic radiation (e.g., visible light) with the Janus droplet in a detectable manner. In some embodiments, exposing a plurality of Janus droplets to an analyte causes a detectable change in an optical property of the Janus droplets, such that the analyte can be determined and/or quantified.

Embodiments described herein may be useful in the formation of emulsions (e.g., complex emulsions). The methods may allow for one-step fabrication of multi-phase (e.g., three-phase, four-phase) emulsions (e.g., complex emulsions), and may be useful in numerous applications including food manufacturing, drug delivery, medical diagnostics, performance materials, cosmetics, MRI and ultrasound contrast agents, artificial blood, among other applications. Furthermore, methods and emulsions described herein may allow for forming emulsions with controlled and reconfigurable morphologies. Another advantageous feature provided by emulsions and methods described herein is the ability to readily incorporate additional components (e.g., magnetic nanoparticles, biological materials, polymers, metals, etc.) into various applications. Emulsions (e.g., complex emulsions) are also provided.

Embodiments described herein may be useful for arranging phases (e.g., in response to a stimulus) and/or components within a colloid. Complex droplets of controllable compositions and dynamic reconfigurable morphologies provide a new active element for novel and existing applications of emulsions and may be useful in numerous applications including food manufacturing, drug delivery, medical diagnostics, performance materials, cosmetics, MRI and ultrasound contrast agents, artificial blood, among other applications. The dynamic rearrangement of droplet phases and/or components can be broadly applied using a wide variety of chemicals, materials, and surfactants, as described herein. Droplets triggered by stimuli could be used, for example, to target release of drugs at tumors, to induce changes in color or transparency (e.g., for applications including color changing mediums and camouflage), as vehicles for sequestration of pollutants, as tunable lenses, as controlled release droplets in response to an stimulus, or as sensors. Emulsions with the characteristic ability to selectively "present" and "hide" specific liquid interfaces and controllably alter droplet morphology and symmetry may be useful for numerous applications and devices. Another advantageous feature provided by emulsions and methods described herein is the ability to readily incorporate additional compounds (e.g., magnetic nanoparticles, biological materials, polymers, metals, etc.) into various applications.

In certain embodiments, upon exposure to an analyte, at least a portion of the plurality of Janus droplets may agglutinate. For example, in some cases, the analyte may facilitate the agglutination of at least a portion of the plurality of Janus droplets. The agglutination of some Janus droplets may result in a detectable change in the interaction of electromagnetic radiation (e.g., visible light) with the Janus droplets. In some cases, the agglutination of some Janus droplets may result in a change in orientation of each of the Janus droplets (e.g., relative to the orientation of the Janus droplets prior to exposure to the analyte). In other cases, the Janus droplets may be in an agglutinated state prior to exposure to an analyte and the exposure of the system to the analyte will disrupt agglutination and case a change in the orientation of the Janus droplet.

Advantageously, in some embodiments, the systems described herein may enable highly sensitive detection of analytes including, for example, detection of single analyte interaction events (e.g., binding events, chemical reactions, biological reactions). In an illustrative embodiment, a single analyte (e.g., one protein, one strand of DNA, one strand of RNA) may cause the agglutination of some Janus droplets and changing the orientation of each of the agglutinated Janus droplets, such that a single analyte (e.g., a single protein, a single strand of DNA, RNA etc.) is detected. In some such embodiments, the single analyte may bind to some Janus droplets such that the Janus droplets agglutinate. In another illustrative embodiment, a single analyte may cause the orientation of a single Janus droplet to change (e.g., via enzymatic degradation of a tether bound to the Janus droplet), such that a single analyte is detected. In some embodiments, a plurality of analytes and/or types of analytes may be detected (e.g., via the change in orientation of a plurality of Janus droplets and/or the agglutination of groups of Janus droplets). In certain embodiments, the concentration of an analyte exposed to the system may be determined by measuring the number of Janus droplets changing orientation upon exposure of the system to the analyte.

As illustrated in FIG. 1A, in some embodiments, system 100 comprises a plurality of Janus droplets such as Janus droplet 120. In certain embodiments, Janus droplet 120 comprises first phase 130 (e.g., comprising a hydrocarbon) and second phase 140 (e.g., comprising a fluorocarbon). As depicted illustratively in FIG. 1A, in some embodiments, first phase 130 and second phase 140 may have relatively the same volume in each Janus droplet. However, those skilled in the art would understand based upon the teaching of this specification that the volume of the first phase and the second phase may not be equal.

In some embodiments, as depicted in FIG. 1A, Janus droplet 120 has a particular orientation, such as orientation 100A. The orientation of a Janus droplet as described herein may be determined by measuring the angle of a planar surface defined by the interface (e.g., interface 125) between the first phase (e.g., first phase 130) and the second phase (e.g., second phase 140). In some embodiments, upon exposure of Janus droplet 120 to an analyte, the Janus droplet may change orientation (e.g., from orientation 100A to orientation 100B). In some such embodiments, the analyte may bind with a binding moiety present on the Janus droplet, resulting in the change in orientation of the Janus droplet. As illustrated in FIG. 1A, the orientation of interface 125 in orientation 100B is different than the orientation of interface 125 in orientation 100A. For example, in some embodiments, the Janus droplet may rotate upon exposure to the analyte (e.g., upon binding of the analyte with a binding moiety associated with the Janus droplet). In some embodiments, the change in orientation of the Janus droplet is determinable (e.g., measurable) such that it indicates the presence of an analyte.

The Janus droplets described herein may be useful in a number of applications. In an exemplary embodiment, the Janus droplets described herein may be used for sensing of an analyte. For example, in some such embodiments, the Janus droplets may change orientation upon exposure to an analyte such that the change in orientation can be detected (e.g., by a change in optical transmission, polarization, birefringence, etc. of the colloid). In another exemplary embodiment, the Janus droplets described herein may be used as tunable lenses. In certain embodiments, measurements of the optical properties (e.g., transmission, absorption, reflection, focal distance, and scattering) of the Janus droplets can be indicative of specific droplet orientations. For example, when a change in droplet orientation is correlated with an analyte of interest (i.e., enzyme, pollutant, virus, bacteria, DNA, RNA, etc.), then, the Janus droplets can be used as sensors in which an optical measurement serves as a readout mechanism of the presence of the analyte. In certain embodiments, for systems in which there is a change in an analyte of interest over time (e.g., progress of a chemical reaction, such as degradation of a chemical by an enzyme over time), tracking of the changes in optical properties of the Janus droplets over time can be used to, for example, analyze reaction rates or analyte concentrations. In some such embodiments, the orientation of the Janus droplets changes in the presence of an analyte such that the system obtains a transparent state over a particular range of time, or alternatively, obtains a relatively opaque state over a particular range of time.

Those skilled in the art would understand that changing a property of a Janus droplet refers to a property of the Janus droplet immediately before that differs in a substantially measurable way from the property of the Janus droplet at some relatively short time (e.g., seconds, minutes, hours) after exposure to the analyte. Those skilled in the art would also be capable of selecting methods for determining the change in the property of the Janus droplets (e.g., measuring the average birefringence, measuring the optical transmission at one or more wavelength, measuring the density, etc.) based upon the specification and examples below.

Figure 1B:
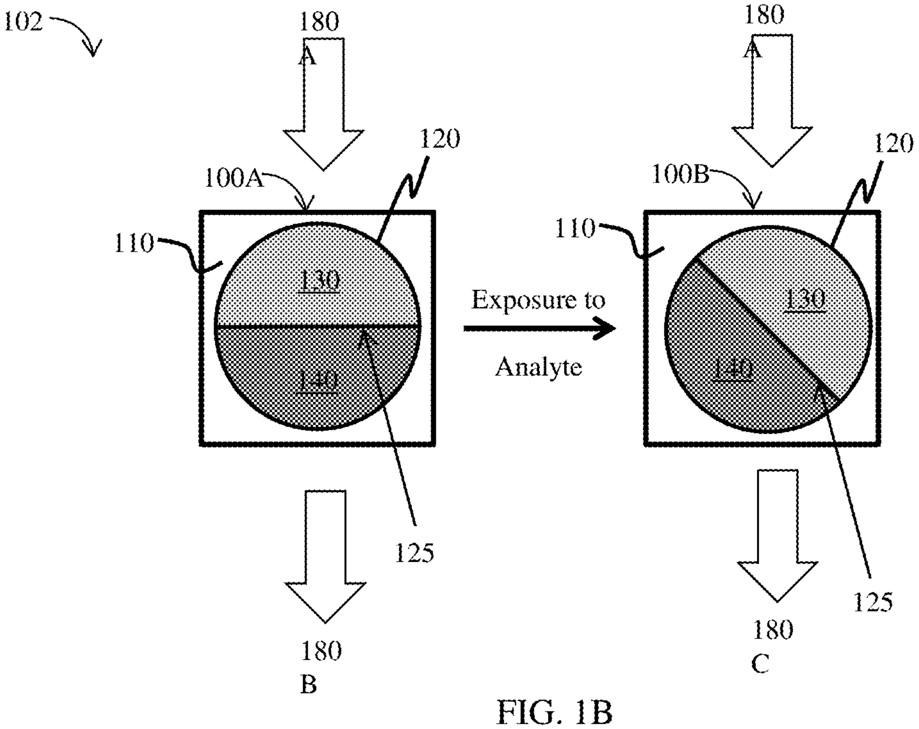
FIG. 1B illustrates a system including a Janus droplet, exposed to an analyte, according to one set of embodiments.

For example, as illustrated in FIG. 1B, system 102 comprises a plurality of Janus droplets such as exemplary Janus droplet 120. In some embodiments, electromagnetic radiation 180A interacts with Janus droplet 120. In certain embodiments, upon exposure of system 102 to an analyte (e.g., such that the analyte binds to a binding moiety associated with the Janus droplet), Janus droplet 120 changes orientation (e.g., from orientation 100A to 100B) sufficiently to change the interaction of electromagnetic radiation 180A with the Janus droplets as compared to the interaction of electromagnetic radiation 180A prior to exposure to the analyte. For example, prior to exposure to the analyte, Janus droplet 120 may interact with electromagnetic radiation 180A such that electromagnetic radiation 180B is produced. In some embodiments, electromagnetic radiation 180A and electromagnetic radiation 180B may be substantially the same. For example, Janus droplet 120 may have an orientation 100A such that electromagnetic radiation interacting with (e.g., transmitting perpendicular to interface 125 of Janus droplet 120) is not substantially changed in wavelength and/or amplitude.

For example, in some cases, the plurality of Janus droplets may be orientation such that the system is substantially optically transparent in a direction perpendicular to the surface of the interface between the first phase and the second phase (e.g., interface 125). In some cases, however, electromagnetic radiation 180B may be different than electromagnetic radiation 180A in wavelength and/or amplitude. In some embodiments, upon exposure of system 102 to an analyte, Janus droplet 120 changes orientation from orientation 100A to orientation 100B, such that electromagnetic radiation 180A interacts with Janus droplet 120 and produced electromagnetic radiation 180C, different than electromagnetic radiation 180B.

In some embodiments, the plurality of Janus droplets is changed in orientation (e.g., upon exposure to an analyte) sufficient to change electromagnetic radiation interacting with the plurality of Janus droplets in a detectable manner. In certain embodiments, at least a portion of the Janus droplets change orientation thereby changing the optical transmission of the article and/or thereby producing a detectable change in an optical property of the article. In some embodiments, the detectable change includes a change in color, average luminescence in one or more directions, and/or average optical transmission of the Janus droplet (or system comprising the plurality of Janus droplets).

In some embodiments the electromagnetic radiation (e.g., the electromagnetic radiation prior to interacting with the Janus droplet, the electromagnetic radiation after interacting with the Janus droplet) may comprise any suitable wavelength, including but not limited to infrared light (e.g., a wavelength between about 700 nm and about 1 cm), to visible light (e.g., a wavelength between about 400 nm and about 700 nm), and to ultraviolet (UV) light (e.g., a wavelength between about 10 nm and about 400 nm).

Figure 1C:
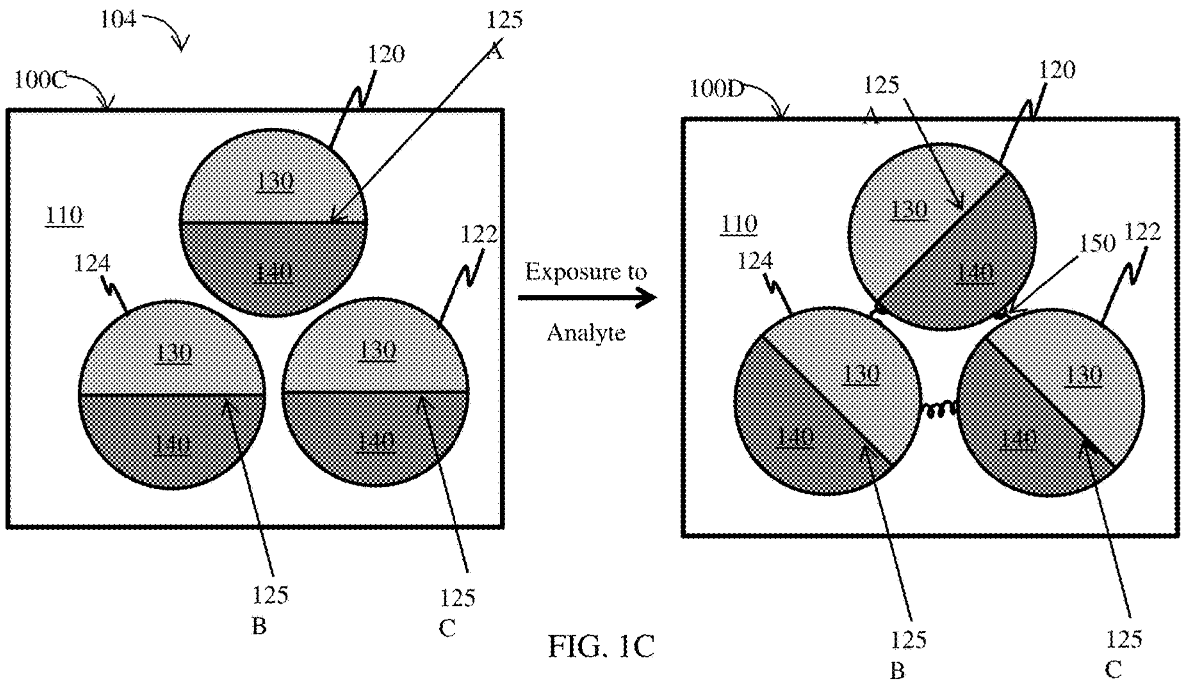
FIG. 1C illustrates a system including a plurality of Janus droplets, exposed to an analyte, according to one set of embodiments.

In certain embodiments, the plurality of Janus droplets (e.g., Janus droplets 120) is dispersed within an outer phase 110, as illustrated in FIGS. 1A-1C. In some embodiments, the outer phase is an aqueous phase (e.g., comprising water). The aqueous phase may also comprise, in some cases, solutes including organic molecules, proteins, ions, cells, DNA, RNA, cell lysates, or biological organisms. In some embodiments, exposing the system to the analyte comprises introducing the analyte into the outer phase. In certain embodiments, the analyte may be added to the outer phase such that the plurality of Janus droplets is exposed to the analyte.

In certain embodiments, the plurality of Janus droplets may be adjacent a surface 150, as illustrated in FIG. 1A. As used herein, when a component (e.g., a Janus droplet) is referred to as being "adjacent" another component (e.g., a surface), it can be directly adjacent to the component, or an intervening component (e.g., a fluid) also may be present. A component that is "directly adjacent" another component means that no intervening component is present (e.g., the component and another component are in contact with one another). Surface 150 may comprise a reflective surface such that exposing the system to an analyte causes a detectable change in an optical property of the Janus droplets such that the reflected electromagnetic radiation from surface 150 is also changed. In an exemplary embodiment, the plurality of Janus droplets is substantially transparent such that surface 150 is visible (e.g., when viewed perpendicular to surface 150) and, upon exposure to an analyte, the plurality of Janus droplets decrease in optical transmission such that at least a portion of surface 150 is obscured. Surface 150 may, in some cases, also be transparent such that light is transmitted through the surface and Janus droplets, such that exposure to an analyte will change the transmission of the light.

In some embodiments, at least a portion of the plurality of Janus droplets are orientated parallel (e.g., as measuring by the angle of a planar surface defined by the interface between the first phase and the second phase of the Janus droplet) to the surface. For example, referring again to FIG. 1A, in some embodiments, interface 125 of Janus droplet 120 (prior to exposure to an analyte) is orientated substantially parallel to surface 150 adjacent Janus droplet 120. In certain embodiments, the plurality of Janus droplets may be orientated substantially parallel to one another (e.g., substantially aligned). In some embodiments, prior to exposure to an analyte, the plurality of Janus droplets is aligned/oriented by the force of gravity (e.g., the first phase or the second phase having a greater density than the other phase) such that at least a portion of the plurality of Janus droplet are oriented substantially parallel with one another. In other embodiments, the forces that cause alignment of Janus droplets may include electrical or magnetic fields. For example, in certain embodiments, the plurality of Janus droplets may include a magnetic phase (e.g., including ferromagnetic particles) In some embodiments, exposure to an analyte results in the agglutination of a plurality of Janus droplets. For example, as illustrated in FIG. 1C, system 104 comprises a plurality of Janus droplets (e.g., exemplary Janus droplets 120, 122, and 124). In certain embodiments, the plurality of Janus droplets may be orientated (relative to interfaces 125A, 125B, and 125C) substantially parallel to one another. In some embodiments, the interface between the first phase and the second phase of at least a portion the plurality of Janus droplet is aligned normal to the primary direction of the force of gravity such that the plurality of Janus droplets are oriented substantially parallel to one another. In some embodiments, upon exposure to an analyte, at least a portion of the Janus droplets agglutinate. In certain embodiments, agglutination of the Janus droplets results in a change of orientation of at least a portion of the Janus droplets (e.g., as measured by the change in angle of interfaces 125A, 125B, and 125C).

In certain embodiments, a binding moiety associated with the Janus droplet may bind with the analyte such that the Janus droplets agglutinate. For example, referring again to FIG. 1C, upon exposure to an analyte, the analyte may bind to a binding moiety on two or more Janus droplets (e.g., forming a bound complex 150 between two or more Janus droplets such as between Janus droplet 120 and Janus droplet 122). One of ordinary skill in the art would understand, based upon the teachings of this specification, that while bound complex 150 is illustrated as binding between first phase 130 and second phase 140, that formation of a bound complex between first phase 130 and first phase 130 of two droplets, is also possible. For example, as shown illustratively in FIG. 15, droplet 120 and droplet 122 are agglutinated via bound complex 152 between first phase 130 of droplet 120 and first phase 130 of droplet 122. Other configurations are also possible.

Figure 1D:
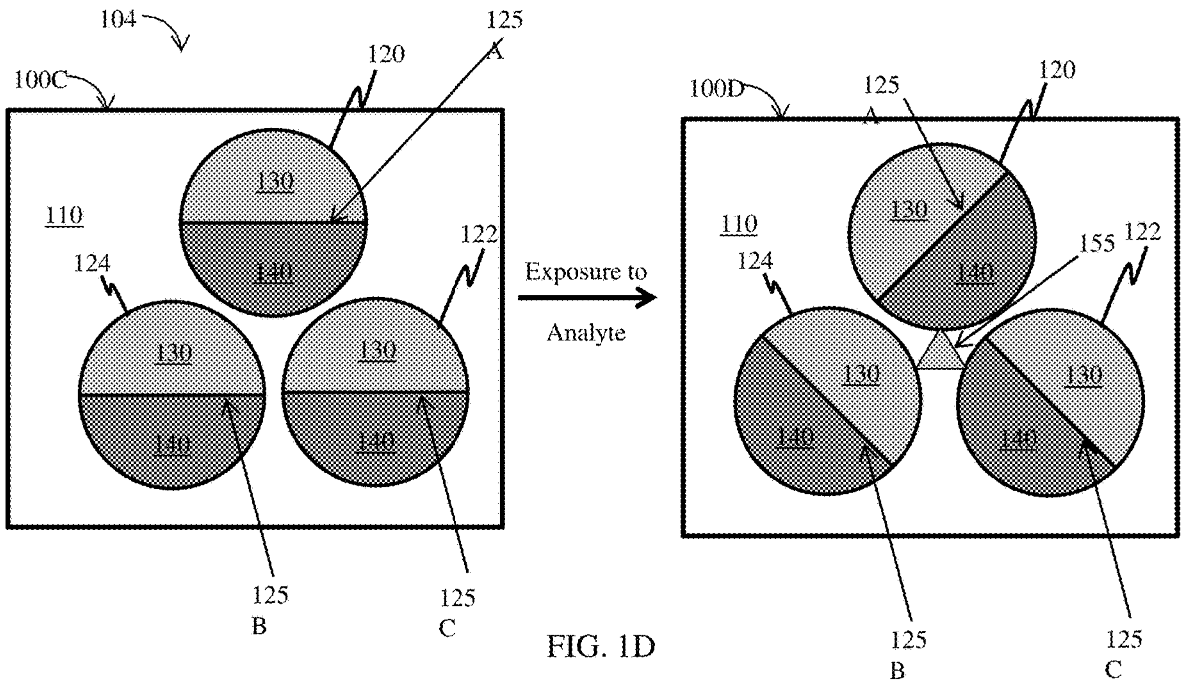
FIG. 1D illustrates a system including a plurality of Janus droplets, exposed to an analyte, according to one set of embodiments.

In some embodiments, a plurality of binding moieties (e.g., binding moieties associated with one or more Janus droplets) may bind with one or more analytes mutlivalently. For example, as illustrated in FIG. 1D, analyte 155 binds multivalently with Janus droplet 120, Janus droplet 122, and Janus droplet 124 such that the Janus droplets agglutinate. In some such embodiments, upon exposure and binding to the analyte, the Janus droplets change orientation sufficient to change electromagnetic radiation interacting with the plurality of Janus droplets in a detectable manner.

In some embodiments, upon agglutination of two or more Janus droplets, at least a portion of incident electromagnetic radiation may retroreflect amongst the droplets such that at least a portion of the electromagnetic radiation is reflected. For example, as shown illustratively in FIG. 15, system 106 comprises a plurality of Janus droplets (e.g., exemplary Janus droplets 120 and 122). In certain embodiments, the plurality of Janus droplets may be orientated (relative to interfaces 125A, and 125B) substantially parallel to one another (100C) and such that electromagnetic radiation 160 is transmitted through the interfaces. In some embodiments, upon exposure to an analyte, at least a portion of the Janus droplets agglutinate (100D). In certain embodiments, agglutination of the Janus droplets results in a change of orientation (100D) of at least a portion of the Janus droplets (e.g., as measured by the change in angle of interfaces 125A and 125B). In some embodiments, the Janus droplets change angle such that at least a portion of electromagnetic radiation 160 is reflected off of interfaces 125A and 125B. In some embodiments, at least a portion of electromagnetic radiation may still transmit through system 106. In some embodiments, the portion of electromagnetic radiation 160 that is reflected may be detected (e.g., by an optical detector, by a user) indicating the presence of the analyte (e.g., the analyte that results in agglutination of the Janus droplets) in the system.

Figure 2:
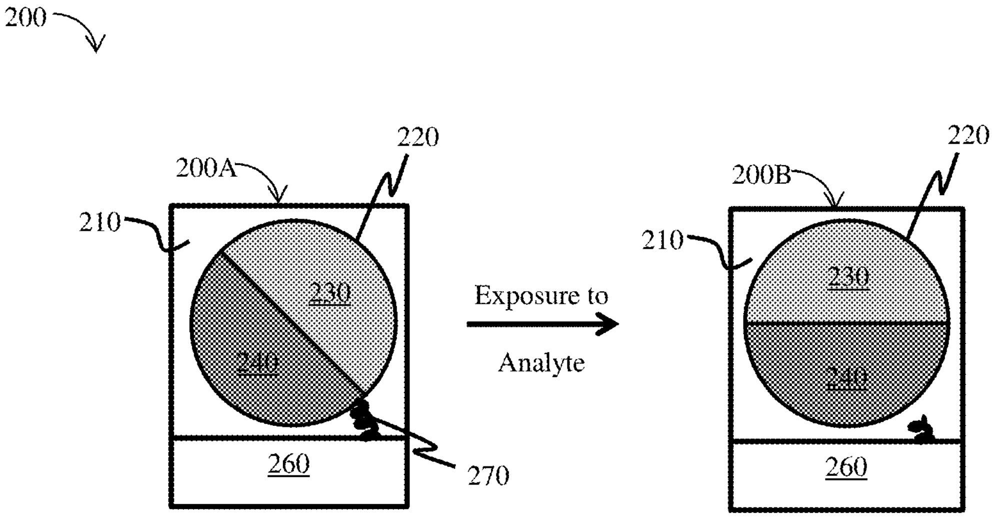
FIG. 2 illustrates a system including a Janus droplet, according to one set of embodiments.

In certain embodiments, the system may comprise a plurality of Janus droplets tethered (e.g., bound) to a surface. In some embodiments, exposure of the system to an analyte results in the breaking (e.g., cleavage) of the tether such that at least a portion of the Janus droplets change orientation (e.g., sufficient to change electromagnetic radiation interacting with the plurality of Janus droplets in a detectable manner). For example, as illustrated in FIG. 2, system 200 comprises Janus droplet 220 comprising first phase 230 and second phase 240, tethered to surface 260 adjacent Janus droplet 220 via tether 270. In some embodiments, exposure to an analyte results in the breaking of tether 270 such that Janus droplet 220 changes orientation (from orientation 200A prior to exposure to the analyte to orientation 200B upon exposure to the analyte). Those skilled in the art would understand based upon the teachings of this specification that surface 260 need not be planar and could be, for example, curved (e.g., the surface comprises a polymeric and/or inorganic particle). In some cases the surface may include an assembly of molecules such as proteins, DNA or RNA. In certain embodiments, the surface may comprise biological tissue (e.g., comprising skin (e.g., human skin), organ tissues, cells, or the like). In some cases, the surface may be a liquid immiscible with the outer phase and/or one or more phases present within the Janus droplets. In some embodiments, the surface comprises a polymeric material.

In some embodiments, the Janus droplet is tethered to the surface such that the interface between the first phase and the second phase is not parallel to the adjacent substrate and/or is not parallel with at least a portion of the plurality of Janus droplets. In some such embodiments, upon breaking of the tether by the analyte, at least a portion of the Janus droplets change orientation (e.g., such that at least a portion of the Janus droplets are parallel with one another and/or are parallel with an adjacent substrate). In some cases, breaking of the tether by the presence of an analyte resulting in an increase in the optical transmission of the system (e.g., such that a feature on the substrate is visible when viewed perpendicular to the surface). The tether may include, for example, one or more proteins, a polymer, one or more strands of DNA, one or more strands of RNA, or combinations thereof. Other tethers are also possible.

The analyte may break the tether in any suitable manner. For example, in some embodiments, the analyte may cleave the tether (e.g., via enzymatic degradation). In certain embodiments, the analyte may cleave the tether by changing the pH of the outer phase such that the tether breaks. In some embodiments, the analyte may cause the cleavage of the tether such that one or more binding moieties associated with (e.g., integrated within) the plurality of Janus droplets bind to the analyte. In some such embodiments, one or more binding moieties may be bound to the tether such that the Janus droplet is bound to the surface and, upon exposure to the analyte, the binding moiety unbinds from the tether and binds to the analyte.

In some cases, the binding moiety may comprise a biological or a chemical group capable of binding another biological or chemical molecule in a medium (e.g., aqueous phase). For example, the binding moiety may include a functional group, such as a thiol, aldehyde, ester, carboxylic acid, hydroxyl, and the like, wherein the functional group forms a bond with the analyte. In some cases, the binding moiety may be an electron-rich or electron-poor moiety wherein interaction between the analyte and the binding moiety comprises an electrostatic interaction. In some cases, the interaction between the analyte and the binding moiety includes binding to a metal or metal-containing moiety.

In some embodiment, the binding moiety and analyte interact via a binding event between pairs of biological molecules including proteins, nucleic acids, glycoproteins, carbohydrates, hormones, drugs, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of binding moieties include peptides, proteins, DNA, RNA, PNA. Other binding moieties and binding pairs are also possible. Binding moieties can also be attached to polymers, organic nanoparticles, inorganic nanoparticles, or metal nanoparticles.

In some embodiments, the binding moiety and the tether interact via a binding event between pairs of biological molecules including proteins, nucleic acids, glycoproteins, carbohydrates, hormones, and the like. In other embodiments the binding moieties can be also bound to a nanoparticle.

In an exemplary embodiment, the binding moiety comprises a protein. In some embodiments, the protein is a hyperthermophilic protein.

The analyte may comprise any suitable material (e.g., a vapor analyte, a liquid analyte, a solid analyte) such that the incorporation of the analyte into the system causes at least a portion of the plurality of Janus droplets to change orientation (e.g., via breaking of a tether and/or agglutination of the Janus droplets). Those skilled in the art would be capable of selecting analytes and components suitable for Janus droplets based upon the teaching of the specification and the examples below. Non-limiting examples of analytes include a biological compound, a drug, a macromolecule, a salt, an electrolyte, an enzyme, a nucleic acid, a carbohydrate, a peptide, a protein, a lipid, a phosphate, a sulfonate, a virus, a pathogen (e.g., bacteria, virus), an oxidant, a reductant, a toxin, a chemical warfare agent, an explosive, carbon dioxide, a surfactant, or combinations thereof. In some embodiments, the tether is a biological compound, a drug, a macromolecule, a salt, an electrolyte, an enzyme, a nucleic acid, a carbohydrate, a peptide, a protein, a lipid, a phosphate, a sulfonate, a virus, a pathogen, an oxidant, a reductant, a toxin, a chemical warfare agent, an explosive, carbon dioxide, a surfactant, or combinations thereof. In an exemplary embodiment, the analyte is a bacterium.

In an exemplary embodiment, an enzyme may be added to the system comprising a plurality of Janus droplets such that the enzyme interacts with one or more of the components, binding moieties, tethers, and/or amphiphilic compounds present in the plurality of Janus droplets. In some such embodiments, the enzyme may interact with the component, binding moiety, tether, and/or amphiphilic compound (e.g., such as a surfactant which is cleaved in the presence of the enzyme) such that at least a portion of the plurality of Janus droplets change orientation as described herein. In certain embodiments, the Janus droplets change orientation at a particular critical concentration of the analyte.

In another exemplary embodiment, one or more Janus droplets may comprise an amphiphilic compound such as a surfactant that is capable of interacting with a biological analyte. In some such embodiments, the Janus droplet may change orientation in the presence of a biological analyte such that the change in orientation can be detected (e.g., by optical transmission).

In some embodiments, the interaction between a binding moiety and the analyte includes a chemical transformation between the binding moiety and the analyte and/or the binding moiety and a tether. Non-limiting examples of chemical transformations include enzymatic degradation, enzymatic synthesis, ionization, cleavage, coupling, hybridization, aggregation, hydrolysis, isomerization, reduction, oxidation, and host-guest interactions of one or more components (or component materials such as a surfactant). Other chemical transformations are also possible.

As described herein, in some embodiments, the methods and systems comprise an outer phase and a plurality of Janus droplets dispersed within the outer phase. In certain embodiments, the plurality of Janus droplets comprises two or more phases. The two or more phases (e.g., a first phase and a second phase) may be substantially miscible over a range of temperatures (e.g., below a critical temperature, above a critical temperature). The two or more phases may also be substantially immiscible over a different range of temperatures (e.g., above the critical temperature, below the critical temperature) than the range of temperatures over which they are miscible. The use of two or more phases with differing miscibility at different temperatures may allow for the one-step formation (e.g., bulk) of such Janus droplets, unconstrained by the limits of previous methods (e.g., low yield of microfluidic devices, multi-step processes, the need for solvent addition and/or extraction, etc.).

Janus droplets described herein may be formed using any suitable method. For example, in some embodiments, an outer phase material, a first phase, and a second phase are mixed and emulsified, forming an outer phase and a plurality of Janus droplets dispersed within the outer phase. Suitable methods for emulsifying the fluid are known in the art and may comprise sonication, high shear mixing, shaking, passing the fluid through a membrane, or injecting the two or more components into the outer phase through a small diameter channel.

Non-limiting examples of methods for forming Janus droplets are described in more detail in commonly-owned U.S. Patent Publication Number 2016/0151753, entitled "Compositions and Methods for Forming Emulsions", filed Oct. 30, 2015 and in U.S. Patent Publication Number 2016/0151756, entitled "Compositions and Methods for Arranging Colloid Phases", filed Oct. 30, 2016, each of which is incorporated herein by reference in its entirety.

In some embodiments, the methods and emulsions comprise an outer phase and a plurality of droplets dispersed within the outer phase. In certain embodiments, the plurality of droplets comprises two or more components. The two or more components may be substantially miscible over a range of temperatures (e.g., below a critical temperature, above a critical temperature). The two or more components may also be substantially immiscible over a different range of temperatures (e.g., above the critical temperature, below the critical temperature) than the range of temperatures over which they are miscible. The use of two or more components with differing miscibility at different temperatures may allow for the one-step formation (e.g., bulk) of emulsions (e.g., complex emulsions), unconstrained by the limits of previous methods (e.g., low yield of microfluidic devices, multi-step processes, the need for solvent addition and/or extraction, etc.)

In some embodiments, the plurality of droplets comprises two or more components, wherein the two or more components are immiscible below or above a critical temperature. In some embodiments, the critical temperature is an upper consolute temperature of the two or more components. That is to say, in some such embodiments, the two components are substantially miscible above the upper consolute temperature of the two or more components and substantially immiscible below the upper consolute temperature of the two or more components. In some embodiments, the critical temperature is a lower consolute temperature of the two or more components. That is to say, in some such embodiments, the two components are substantially miscible below the lower consolute temperature of the two or more components and substantially immiscible above the lower consolute temperature of the two or more components. In some embodiments, the miscibility of the two or more components is reversible. That is to say, the miscibility of the two or more components can be changed, in some embodiments, by increasing or decreasing the temperature to a temperature greater than, or less than, the critical temperature.

In some embodiments, two or more components may have an upper consolute temperature greater than or equal to about 0° C., greater than or equal to about 5° C., greater than or equal to about 8° C., greater than or equal to about 10° C., greater than or equal to about 15° C., greater than or equal to about 18° C., greater than or equal to about 20° C., greater than or equal to about 22° C., greater than or equal to about 25° C., greater than or equal to about 27° C., greater than or equal to about 30° C., greater than or equal to about 35° C., greater than or equal to about 40° C., greater than or equal to about 50° C., greater than or equal to about 55° C., or greater than or equal to about 60° C. In certain embodiments, the upper consolute temperature of the two or more components is less than about 70° C., less than about 60° C., less than about 55° C., less than about 50° C., less than about 40° C., less than about 35° C., less than about 30° C., less than about 27° C., less than about 25° C., less than about 22° C., less than about 20° C., less than about 18° C., less than about 15° C., less than about 10° C., less than about 8° C., or less than about 5° C. Combinations of the above-referenced ranges are also possible (e.g., a upper consolute temperature of greater than or equal to about 0° C. and less than about 70° C.). Other ranges are also possible. Those skilled in the art would be capable of selecting suitable methods for determining the upper consolute temperature of two or more components.

In some embodiments, two or more components may have a lower consolute temperature greater than or equal to about 0° C., greater than or equal to about 5° C., greater than or equal to about 8° C., greater than or equal to about 10° C., greater than or equal to about 15° C., greater than or equal to about 18° C., greater than or equal to about 20° C., greater than or equal to about 22° C., greater than or equal to about 25° C., greater than or equal to about 27° C., greater than or equal to about 30° C., greater than or equal to about 35° C., greater than or equal to about 40° C., greater than or equal to about 50° C., greater than or equal to about 55° C., or greater than or equal to about 60° C. In certain embodiments, the lower consolute temperature of two components is less than about 70° C., less than about 60° C., less than about 55° C., less than about 50° C., less than about 40° C., less than about 35° C., less than about 30° C., less than about 27° C., less than about 25° C., less than about 22° C., less than about 20° C., less than about 18° C., less than about 15° C., less than about 10° C., less than about 8° C., or less than about 5° C. Combinations of the above-referenced ranges are also possible (e.g., a lower consolute temperature of greater than or equal to about 0° C. and less than about 70° C.). Other ranges are also possible. Those skilled in the art would be capable of selecting suitable methods for determining the lower consolute temperature of two or more components.

In some embodiments, the two or more components have a greater miscibility at a first temperature as compared to a second temperature. That is to say, at the first temperature, the two or more components may be miscible to some extent, and miscible to some lesser extent (e.g., immiscible to some extent) at the second temperature.

In some cases, the two or more components may be substantially miscible over a range of pressures (e.g., below a critical pressure, above a critical pressure). The two or more components may also be substantially immiscible over a different range of pressure (e.g., above the critical pressure, below the critical pressure) than the range of pressures over which they are miscible. The use of two or more components with differing miscibility at different pressures may allow for the one-step formation (e.g., bulk) of emulsions (e.g., complex emulsions), unconstrained by the limits of previous methods (e.g., low yield of microfluidic devices, multi-step processes, the need for solvent addition and/or extraction, etc.)

Those skilled in the art would be capable of selecting a suitable temperature and/or suitable pressure range for forming the emulsions described herein based upon the teachings of the specification and the examples below, and would generally understand these temperature ranges and/or pressure ranges to include ranges in which the two or more components remain substantially fluid (e.g., below the boiling point of the two or more components, above the freezing point of the two or more components.) In some embodiments, the two or more components are immiscible with the outer phase over the suitable temperature range and/or pressure range.

Immiscible, as used herein, refers to two components (or a phase and a component, or a first phase and a second phase) having an interfacial tension of greater than or equal to 0.01 mN/m as determined by an inverted pendant drop goniometer. Conversely, miscible, as used herein, refers to two components (or a phase and a component) having an interfacial tension of less than 0.01 mN/m as determined by an inverted pendant drop goniometer.

In some embodiments, at a temperature (and/or pressure) wherein the two or more components are immiscible, the two or more components comprise a first component and a second component at least partially encapsulated within the first component. In certain embodiments, at a temperature (and/or pressure) wherein the two or more components are immiscible, the two or more components do not encapsulate each other but interface with the outer phase (or an additional component at least partially encapsulating the two or more components) to form Janus droplets. Janus droplets are generally droplets where the droplet is divided into two or more distinct parts comprising two or more different components that do not encapsulate each other. For example, in some embodiments, the emulsion comprises an aqueous phase and a plurality of droplets comprising a hydrocarbon and a fluorocarbon, wherein the plurality of droplets are Janus droplets.

The term component, as used herein, generally refers to a portion of a droplet comprising a group of substantially similar molecules, a group of substantially similar compounds, and/or a phase (e.g., a non-aqueous phase, an aqueous phase). Those skilled in the art would understand that is not intended to refer to single molecules or atoms. In some embodiments, the component is a liquid phase (e.g., a gas phase, an aqueous phase, a non-aqueous phase) comprising a group of substantially similar compounds and/or molecules. For example, in some cases, each component may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more components.

The term phase, as used herein, generally refers to a portion of a droplet or fluid comprising a group of substantially similar molecules, and/or a group of substantially similar compounds. Those skilled in the art would understand that is not intended to refer to single molecules or atoms. In some embodiments, the phase is a liquid phase (e.g., an aqueous phase, a non-aqueous phase) comprising a group of substantially similar compounds and/or molecules and/or polymers. For example, in some cases, each phase may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more phases.

In some embodiments, at least one of the two or more phases (e.g., the first phase) comprises a hydrocarbon. Non-limiting examples of suitable hydrocarbons include alkanes (e.g., hexane, heptane, decane, dodecane, hexadecane), alkenes, alkynes, aromatics (e.g., benzene, toluene, xylene, benzyl benzoate, diethyl phalate), oils (e.g., natural oils and oil mixtures including vegetable oil, mineral oil, and olive oil), liquid monomers and/or polymers (e.g., hexanediol diacrylate, butanediol diacrylate, polyethylene glycols, trimethylolpropane ethoxylate triacrylate), alcohols (e.g., butanol, octanol, pentanol), ethers (e.g., diethyl ether, diethylene glycol, dimethyl ether), nitromethane, halogenated liquids (e.g., chloroform, dichlorobenzene, methylene chloride, carbon tetrachloride), brominated liquids, iodinated liquids, lactates (e.g., ethyl lactate), acids (e.g., citric acid, acetic acid), liquid crystals (4-cyano-4'-pentylbiphenyl), trimethylamine, liquid crystal hydrocarbons (e.g., 5-cyanobiphenyl), combinations thereof, and derivatives thereof, optionally substituted. In some embodiments, the hydrocarbon comprises a halogen group, sulfur, nitrogen, phosphorous, oxygen, or the like. Other hydrocarbons and solutes are also possible.

As described herein, in some embodiments, one of the two or more phases (e.g., the hydrocarbon phase) may comprise a liquid crystal (LC). In some embodiments, a droplet (e.g., a Janus droplet) comprises a liquid crystal and a fluorocarbon. Accordingly, LC complex colloids are described herein. In some embodiments, one component is a LC and the other is an isotropic fluorocarbon oil and may demonstrate how the anisotropic nature of the LC compartment can introduce new functionalities and unusual behaviors.

The substitution or inclusion of isotropic hydrocarbon oils by LCs results, in some embodiments, in a destabilization of the internal interface with the fluorocarbon phase thereby leading to the formation of non-spherical double emulsions. As a result, new methods to decrease these internal interfacial tensions are described to stabilize spherical structures over the range of droplet morphologies: LC-in-fluorocarbon-in-water double emulsions (LC/F/W), Janus emulsions, and inverted double emulsions (fluorocarbon-in-LC-in-water, F/LC/W).

Figure 24:
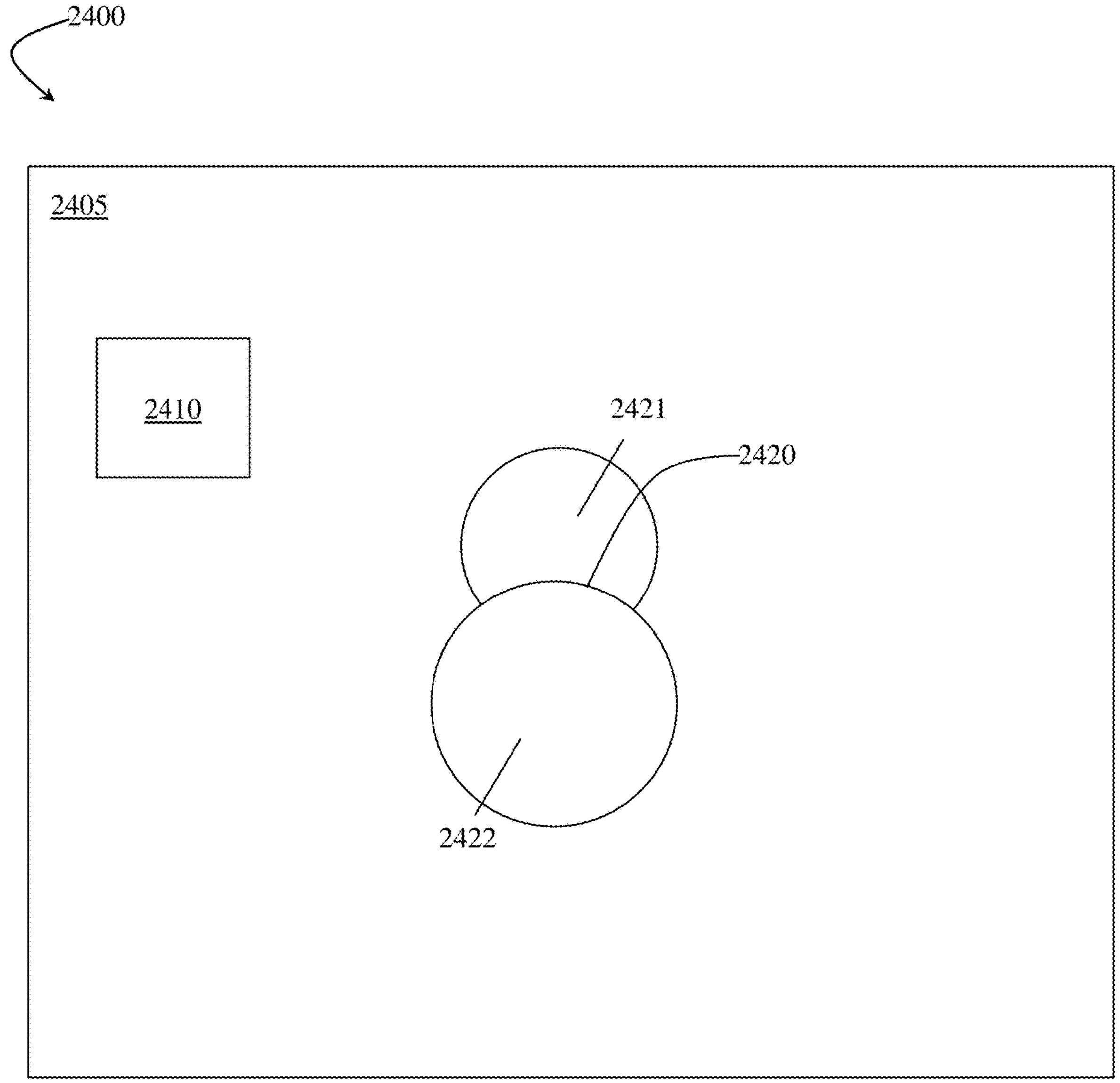
FIG. 24 is a schematic cross section of a colloid, with a droplet, the droplet comprising a hydrocarbon phase and fluorocarbon phase, according to some embodiments.

Referring now to FIG. 24, the colloid 2400 comprises an aqueous phase 2405, a droplet 2420, droplet 2420 comprises the hydrocarbon phase 2421 and the fluorocarbon phase 2422. Colloid 2400 may also comprise a surfactant, such as surfactant 2410. The inclusion of a liquid crystal in hydrocarbon phase 2421 can change the interfacial tension between hydrocarbon phase 2421 and fluorocarbon phase 2422. For example, as schematically shown in FIG. 24, fluorocarbon phase 2422 is slightly larger than hydrocarbon phase 2421 to provide a "snowman"-like geometry. The liquid crystal composition of the hydrocarbon phase can be used to tune the relative geometries between the hydrocarbon phase and the fluorocarbon phase. While FIG. 24 shows the fluorocarbon phase as slightly larger than the hydrocarbon phase, it should be understood that in some embodiments, the hydrocarbon phase can be larger, while in other embodiments, the fluorocarbon phase and the hydrocarbon phase are substantially similar in size.

In some embodiments, new mesogenic surfactants are described for creating LC complex colloids exhibiting different internal configurations. In some cases, the ability to control the anchoring and interfacial tension at each LC-interface may enable defined configurations with thermodynamically stable defects of varied topologies. In some cases, LC generated topological defects are powerful templates for the spatial organization of biomolecules at the droplet's interface for future biological and sensing technologies. In some embodiments, the LC can comprise magnetic particles.

Certain embodiments comprise a cholesteric phase. Cholesteric or chiral nematic phase as described herein is given its ordinary meaning in the art to describe liquid nematic crystals with a helical structure and/or the liquid crystals comprise a chiral compound (e.g., a dopant).

In some embodiments, dynamically reconfigurable complex emulsions comprising two immiscible liquids, a liquid crystal and a fluorocarbon oil are described. Without wishing to be bound by any theory, the high intrinsic surface tension between the LC and the fluorocarbon phase gives a non-spherical, snowman morphology as described in the context of FIG. 24. Producing stable spherical LC droplets may require the simultaneous balancing of many (e.g., all) interfacial tensions, which may be accomplished by the use of designed monomeric or polymeric internal surfactants. In certain embodiments, once the interfaces are stabilized, spherical LC droplet morphologies may be dynamically switched between LC/F/W double emulsions, Janus emulsions, and/or inverted F/H/W double emulsions. For some cases, the nematic LC stabilization developed for 5CB, can be extended to 8CB, a smectic A LC, creating droplets with more complex internal nanostructures as described later in the Examples. By using the surfactants described herein, droplets with different LC director fields can be created. In addition, by the design of LCs, droplets can be oriented in a radial direction (perpendicular to the interface) or in planar fashion (parallel to the interface). In some cases, these designs may be executed at both internal LC/F interfaces and the LC/W interface. In some embodiments, the control of the position of the topological singularities may allow for the precision assembly of antibodies. Dynamic complex colloids with controlled structures may provide access to a multitude of sensing applications.

In some embodiments, at least one of the two or more phases (e.g., the second phase) comprises a fluorocarbon. Non-limiting examples of suitable fluorocarbons include fluorinated compounds such as perfluoroalkanes (e.g., perfluorohexanes, perfluorooctane, perfluorodecalin, perfluoromethylcyclohexane), perfluoroalkenes (e.g., perfluorobenzene), perfluoroalkynes, and branched fluorocarbons (e.g., perfluorotributylamine). Additional non-limiting examples of suitable fluorocarbons include partially fluorinated compounds such as methoxyperfluorobutane, ethyl nonafluorobutyl ether, 2H,3H-perfluoropentane, trifluorotoluene, perfluoroidodide, fluorinated or partially fluorinated oligomers, 2,2,3,3,4,4,5,5,6,6,7,7,8,8,9,9-hexadecafluorodecane-1,10-diyl bis(2-methylacrylate), perfluoroiodide, and 2-(trifluoromethyl)-3-ethoxydodecafluorohexane. Other fluorocarbons are also possible.

In some embodiments, at least one of the two or more components phases a silicone such as silicone oil. Non-limiting examples of suitable silicone oils include polydimethylsiloxane and cyclosiloxane fluids.

In some embodiments, at least one of the two or more phases comprises water.

In some embodiments, at least one of the two or more phases comprises an ionic liquid (e.g., an electrolyte, a liquid salt). In some embodiments, at least one of the two or more inner phases comprises an ionic liquid (e.g., an electrolyte, a liquid salt, 1-allyl-3-methylimidazolium bromide, 1-allyl-3-methylimidazolium chloride, 1-benzyl-3-methylimidazolium hexafluorophosphate, 1-butyl-1-methylpyrrolidinium hexafluorophosphate). In some embodiments, the outer phase comprises water. In certain embodiments, at least one of the two or more phases comprises a deuterated compound (e.g., a deuterated hydrocarbon).

In some embodiments, at least one of the two or more phases comprises a chlorinated solvent (e.g. chloroform, carbon tetrachloride).

In some embodiments, at least one of the two or more components comprises a polymer (e.g., polyethylene glycol). In certain embodiments, the polymer is a block copolymer. In certain embodiments, the polymer is a liquid crystal polymer (e.g., a thermotropic liquid crystal polymer). In certain embodiments, the polymer is a biopolymer (e.g. gelatin, alginate)

Non-limiting examples of combinations of components present in the emulsion described herein include hexane and perfluorohexane, carbon tetrachloride and perfluorohexane, chloroform and perfluorohexane, hexane and perfluorodecalin, hexane and perfluoromethylcyclohexane, hexane and perfluorotributylamine, isopropanol and hexadecane, ethyl lactate and heptane, acetic acid and decane, and triethylamine and water. Other combinations and materials are also possible.

In some embodiments, at least one of the two or more components comprises a gas (e.g., a perfluoropentane gas).

In some embodiments, at least one of the two or more phases comprises a combination of the materials described above (e.g., comprising a hydrocarbon, a fluorocarbon, a silicone, or combinations thereof). Non-limiting examples of combinations of phases present in the Janus droplets described herein include hexane and perfluorohexane, carbon tetrachloride and perfluorohexane, chloroform and perfluorohexane, hexane and perfluorodecalin, hexane and perfluoromethylcyclohexane, hexane and perfluorotributylamine, isopropanol and hexadecane, ethyl lactate and heptane, acetic acid and decane, and triethylamine and water. Other combinations and materials are also possible.

In some embodiments, at least one of the two or more components comprises a combination of the materials described above (e.g., comprising a hydrocarbon, a fluorocarbon, a silicone, or combinations thereof).

Those skilled in the art would be capable of selecting suitable phases based upon the teachings of the specification and the examples below such that the two or more phases are immiscible under a particular range of temperatures and/or conditions, as described above.

The outer phase may comprise any suitable material. Generally, the two or more phases comprising the plurality of Janus droplets may be substantially immiscible with the outer phase. In some embodiments, the outer phase is an aqueous phase (e.g., comprising water). The aqueous phase may, in some cases, have ions and/or be mixed with a biological fluid (e.g., sputum, blood, plasma, urine). In certain embodiments, the outer phase is a non-aqueous phase. In some embodiments, the non-aqueous phase comprises a hydrocarbon, a fluorocarbon, a silicone, or the like, as described above in the context of the two or more phases, substantially immiscible with the two or more phases. Those skilled in the art would be capable, based upon the teachings of the specification and the examples below, of selecting suitable materials for use as an outer phase based upon the miscibility of those materials (e.g., such that the two or more phases are substantially immiscible with the outer phase). The use of a non-aqueous outer phase may be advantageous in certain applications where the emulsion is used in low humidity environments. For example, a plurality of Janus droplets comprising fluorocarbon/hydrocarbon phases can be created in a liquid silicone matrix.

Those skilled in the art would be capable, based upon the teachings of the specification and the examples below, of selecting suitable materials for use as an outer phase based upon the miscibility of those materials (e.g., such that the two or more components are substantially immiscible with the outer phase). The use of an non-aqueous outer phase may be advantageous in certain applications where the emulsion is used in low humidity environments. For example, a plurality of droplets comprising fluorocarbon/hydrocarbon phases can be created in a liquid silicone matrix. The silicone can be crosslinked of polymerized to change its mechanical properties. In some embodiments, at least a portion of the droplets may be deformed and/or aligned by mechanically deforming (e.g., applying a mechanical force to) the outer phase.

In some embodiments, the Janus droplet comprises an amphiphilic compound. In certain embodiments, the binding moiety is associated with the amphiphilic compound. For example, the binding moiety may be bound to at least a portion of the amphiphilic compound.

In certain embodiments, the amphiphilic compound is miscible in the outer phase. In some embodiments, the amphiphilic compound is miscible in at least one of the two or more phases (e.g., the first phase, the second phase). In certain embodiments, the amphiphilic compound has a greater miscibility in at least one of the two or more phases than a miscibility in the outer phase. In other embodiments the amphiphilic compound is added to the Janus droplet though a dispersion, such as an aqueous micelle structure or dissolution method (e.g., comprising injecting a dispersion of the amphiphilic compound into the solution containing the Janus droplets). In some embodiments, the amphiphilic compound is disposed at the interface between the outer phase and the plurality of Janus droplets. Amphiphilic compounds may also be generated, in some embodiments, by reaction of a solute in one phase with solute in another phase. For example, without wishing to be bound by theory, a reactive group in an organic phase may, in some cases, react with a solute from an aqueous phase to create a amphiphilic molecule at the surface of a droplet. In certain embodiments, the amphiphilic compound is disposed at the interface between at least two of the two or more phases (e.g., the interface between the first phase and the second phase). The amphiphilic compound may preferentially interact with one or more phases or the outer phase. Those skilled in the art would be capable of selecting a suitable amphiphilic compound based upon the teachings of the specification and examples below.

In some embodiments, the amphiphilic compound is a surfactant. Non-limiting examples of suitable surfactants include ionic surfactants, non-ionic surfactants, and zwitterionic surfactants. In some embodiments, the surfactant is a fluorosurfactants (e.g., commercially available fluorosurfactants such as Zonyl® or Capstone®). In certain embodiments, the surfactant is anionic surfactants (e.g., sodium dodecyl sulfate (SDS)), cationic surfactants (e.g., alkyltrimethyl ammonium chloride, alkylmethyl ammonium bromide), non-ionic surfactants (e.g., alkyl poly(ethylene oxide)), zwitterionic surfactants (e.g., alkyl betain, C8-lecitin), polymeric surfactants, gemini surfactants, particulate surfactants (e.g., graphene oxide, silica particles, gold nanoparticles, polymer nanoparticles), and combinations thereof. Other surfactants are also possible. In some embodiments, the amphiphilic compound is a nucleic acid (e.g., DNA, RNA). In certain embodiments the amphiphilic compound comprises an amino acid (e.g., a peptide, a protein). In some embodiments, the amphiphilic compound comprises a biomaterial. Non-limiting examples of suitable biomaterials include carbohydrates or derivatives thereof, saccharides or derivatives thereof (e.g., sialic acid), lipids or derivatives thereof, enzymes, chromophores or the like. Those skilled in the art would be capable of selecting suitable biomaterials based upon the teachings of the specification and the examples below.

In some embodiments, the amphiphilic compound comprises a perfluorinated segment. In some embodiments, the amphiphilic compound comprises ethylene glycol.

In some embodiments, the amphiphilic compound is capable of forming metal complexes.

In some embodiments, the amphiphilic compound is gallic acid or derivatives thereof (e.g., tridodecyl gallic acid).

In some embodiments, the amphiphilic compound has a structure as in formula (I):

(I)

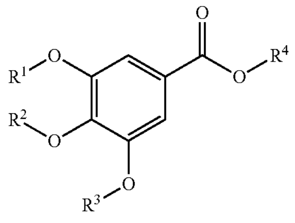

wherein each $R^1$-$R^3$ is the same or different and comprises hydrogen or alkyl, optionally substituted, and wherein $R^4$ is capable of binding to a biological analyte. In some embodiments, each of $R^1$-$R^3$ are the same or different and are $C_nH_{n+1}$, where n is an integer greater than or equal to 10 and less than or equal to 30 (e.g., 10, 11, 12, 13, 14, 15, 16, 17, 18, 19, 20, 21, 22, 23, 24, 25, 26, 27, 28, 29, 30). In some embodiments, $R^1$, $R^2$, and/or $R^3$ may be a saturated or unsaturated alkyl chain, optionally substituted. In some embodiments, $R^4$ comprises or is derived from methyl, carbonyl, carboxyl, N-hydroxysuccinimide, 1-ethyl-3-(3-dimethylaminopropyl)carbodiimide, and N-(2-aminoethyl)maleimide.

In some embodiments, the amphiphilic compound is capable of forming a bond with an analyte (e.g., a biological analyte). In some embodiments, $R^4$ is capable of forming the bond with the analyte. In some embodiments, $R^4$ is capable of interacting with the analyte via formation of a bond, such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus, nitrogen, carbon-nitrogen, metal-oxygen, or other covalent bonds. The hydrogen bond may be, for example, between hydroxyl, amine, carboxyl, thiol, and/or similar functional groups.

In some embodiments, $R^4$ comprises one or more binding moieties as described herein.

In some embodiments, the amphiphilic compound may comprise a polymer (e.g., a block copolymer), as described herein. Non-limiting examples of suitable polymers for use as amphiphilic compounds include:

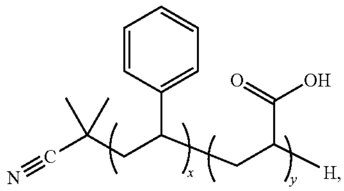

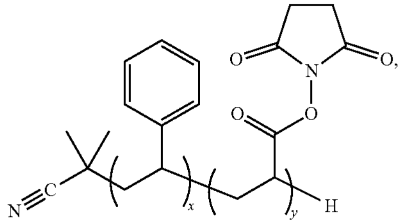

and

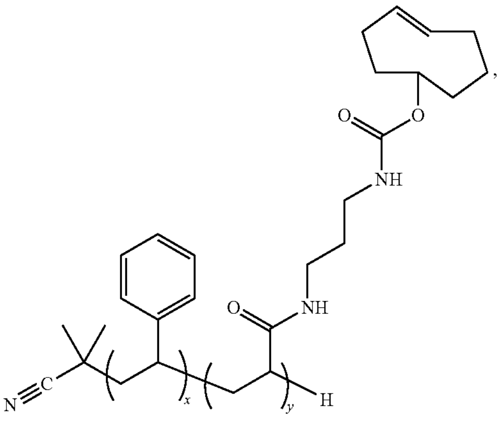

where x is 0-1, y is 0-1, and x+y=1. In some embodiments, a tetrazine click reaction may be used to form and/or react with the amphiphilic compound (e.g., the polymer).

In some embodiments, the one or more phases (e.g., the first phase, the second phase) and/or the outer phase comprises an additional compound dispersed in the one or more phases and/or the outer phase. In certain embodiments, the additional compound is miscible/dispersible in the first phase and immiscible/not dispersible in the second phases. In some cases, at least a portion of the additional compound is dispersible in the first phases and not dispersible in the second phases (e.g., a surfactant). In some embodiments, the additional compound may be dispersible or not dispersible in the outer phase. Non-limiting examples of suitable additional compounds include particles (e.g., magnetic particles/nanoparticles, silica particles), biological molecules (e.g., insulin), pharmaceutical compounds, polymers, surfactants, cells, bacteria, viruses, active pharmaceutical ingredients, and metals or metal particles. Other additional compounds are also possible and those skilled in the art would be capable of selecting such compounds based upon the teachings of this specification.

As described above, in some embodiments, the colloids, articles, system, and/or methods described herein may include magnetic particles (e.g., magnetic nanoparticles, $Fe_3O_4$ nanoparticles). The inclusion of magnetic nanoparticles may provide movement, for example, to double emulsions (e.g., Janus droplets) as described herein. The particles may be functionalized (e.g., amine functionalized) such that they may bind or interact with one phase (e.g., the hydrocarbon phase) of the Janus droplet while not binding or interacting with the other phase (e.g., the fluorocarbon phase). The attraction and repulsion of the emulsions to applied magnetic fields may result in controlled orientational changes and rotational movement. Furthermore, incorporation of liquid crystals into the double emulsions may add additional templating capabilities for precision assembly of magnetic nanoparticles, both along the interface and at point defects of the double emulsion. In some embodiments, the magnetic particles are associated with a liquid crystal (e.g., a hydrocarbon phase comprising a liquid crystal)

In some embodiments, a phase (e.g., a hydrocarbon phase, a liquid crystal containing phase) may be functionalized to selectively bind or attach a magnetic particle (e.g., an $Fe_3O_4$ nanoparticle). For example, the magnetic particle may be functionalized with an amine functional group, and the hydrocarbon phase and/or the fluorocarbon phase may be functionalized with an aldehyde or aldehyde-hydrate functional group such that the magnetic particles can selectively react to form an imine that attaches the magnetic particle to the hydrocarbon phase and/or the fluorocarbon phase. However, other functional groups of the magnetic particles are also contemplated (e.g., hydroxyl, thiol) and the hydrocarbon phase and/or the fluorocarbon phase can be functionalized with other carbonyl-containing moieties (e.g., a ketone, a carboxyl, an amide) in order to provide attachment of the magnetic particles as this disclosure is not so limited.

In some embodiments, the emulsion can be formed by adjusting the temperature of a fluid comprising the outer phase and the two or more immiscible components such that the two or more components become substantially miscible with each other, and emulsifying the fluid (e.g., thus forming the plurality of droplets). In certain embodiments, the method comprises adjusting the temperature of the fluid comprising the plurality of droplets such that the two or more components become substantially immiscible.

In some embodiments, the plurality of Janus droplets can be formed by adjusting the temperature of a fluid comprising the outer phase and the two or more immiscible phases such that the two or more phases become substantially miscible with each other, and emulsifying the fluid (e.g., thus forming the plurality of Janus droplets). In certain embodiments, the method comprises adjusting the temperature of the fluid comprising the two phases such that the two or more phases become substantially immiscible. In other embodiments, the method comprises the addition of a solvent that creates a stable uniform composition prior to emulsification, and the solvent is removed by evaporation or extraction to give phase separation and produce a Janus droplet.

Figure 3A:
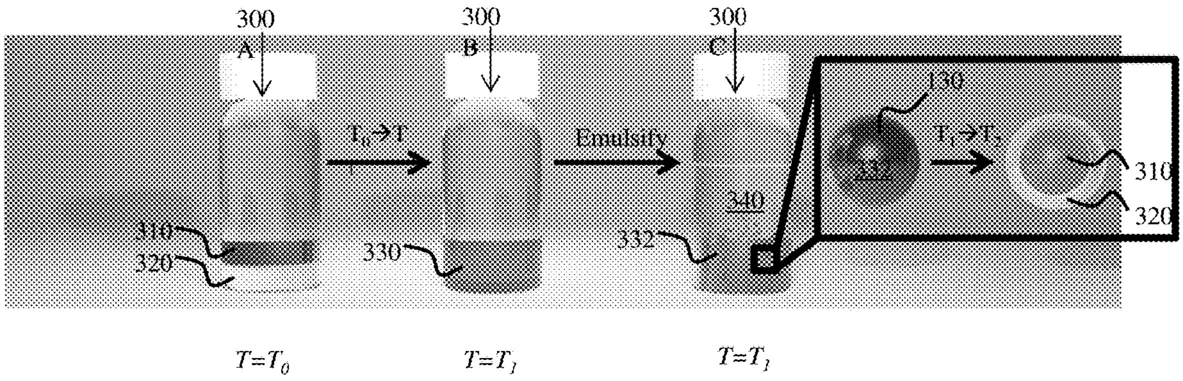
FIG. 3A illustrates the formation of complex emulsions, according to one set of embodiments.
Figure 3B:
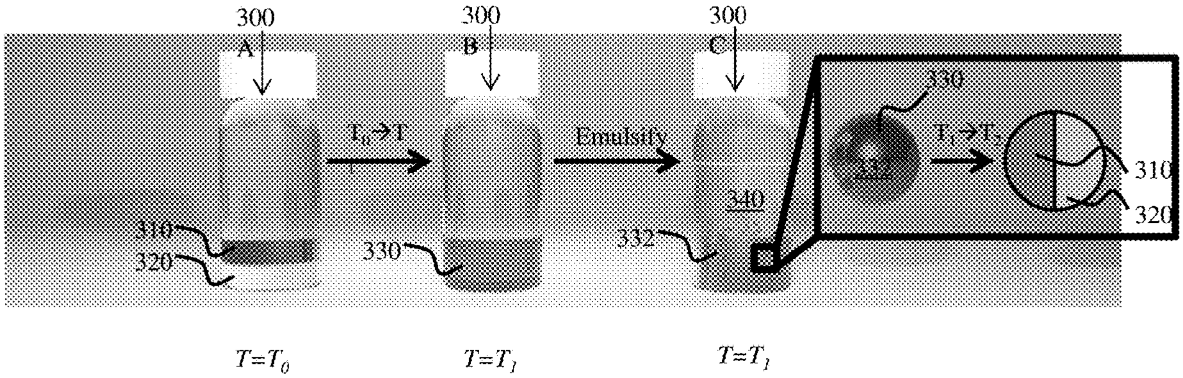
FIG. 3B illustrates the formation of complex emulsions, according to one set of embodiments.

For example, as illustrated in FIG. 3B, a fluid 300A comprises first phase 310 (e.g., a hydrocarbon) and second phase 320 (e.g., a fluorocarbon) which are immiscible at a first temperature $T_0$. In some embodiments, $T_0$ is adjusted to a second temperature $T_1$ (e.g., where $T_1$ is greater than $T_0$, or where $T_1$ is less than $T_0$) such that the first component and second component form a miscible mixture 330 in fluid 300B. For example, in some embodiments, the first phase and the second phase, which are initially substantially immiscible, may be heated such that they are miscible. In certain embodiments, the first phase and the second phase, which are initially substantially immiscible, may be cooled such that they are miscible. Miscible mixture 330 can, in certain embodiments, be emulsified to form emulsion 300C comprising plurality of droplets 332. Plurality of droplets 332 may comprise miscible mixture 330 and be present in an outer phase 340. In some cases, outer phase 340 may be added prior to changing the temperature from $T_0$ to $T_1$. In certain embodiments, outer phase 340 may be added after changing the temperature but prior to emulsification.

In some embodiments, T1 is adjusted to a temperature T2 (e.g., where T2 is greater than T1 or where T2 is less than T1) such that droplet 332 comprises first component 310, and second component 320 substantially immiscible with first component 310, contained within the droplet. In some such embodiments, first component 310 may be at least partially encapsulated by second component 320. In some embodiments, first component 310 and second component 320 are not encapsulated but form a Janus particle (FIG. 3B).

In some embodiments, $T_1$ is adjusted to a temperature $T_2$ (e.g., where $T_2$ is greater than $T_1$ or where $T_2$ is less than $T_1$) such that droplet 332 comprises first phase 310, and second phase 320 substantially immiscible with first component 310, forming a Janus droplet.

In some embodiments, $T_1$ is greater than a critical temperature of the two or more phases (e.g., an upper consolute temperature of the two or more phases). In certain embodiments, $T_1$ is less than a critical temperature of the two or more phases (e.g., a lower consolute temperature). Those skilled in the art will be capable of selecting suitable methods for determining the critical temperature (e.g., the upper consolute temperature, the lower consolute temperature) of two or more phases.

Suitable methods for emulsifying the fluid are known in the art and may comprise sonication, high shear mixing, shaking, passing the fluid through a membrane, or injecting the two or more components into the outer phase through a small diameter channel.

Colloids (e.g., droplets) described herein offer numerous advantages to colloids known in the art, including the ability to reversibly, dynamically, and/or controllably change the arrangement and/or configuration of the components within the colloid (e.g., in response to an external stimulus, a change in temperature, or an analyte). In some embodiments, the colloid comprises an outer phase and a plurality of droplets (or regions) comprising two or more components. For example, in certain embodiments, the colloid comprises an outer phase and a plurality of droplets comprising a first component and a second component. In some cases, the colloid comprises an outer phase, and a plurality of droplets (or regions) comprising a first component, a second component, and a third component. Additional components are also possible.

In certain embodiments, the colloid comprises an outer phase and a plurality of droplets where a first component encapsulates a second component. In some embodiments, the colloid may be stimulated (e.g., by a first stimulus such as a change in temperature or exposure to an analyte) such that the components change arrangement and the second component encapsulates the first component. Those skilled in the art would understand that changes in arrangement as described herein do not refer to the motion of immiscible phases in a colloid due to regular fluid motion driven by passive diffusion and/or Brownian motion, but instead refer to the controlled change in arrangement of phases as a result of the addition of a particular stimulus or condition not present prior to the rearrangement of phases (or removal of a particular stimulus or condition, present prior to the rearrangement of phases), and are described in more detail below. In certain cases, a change in temperature may increase the passive diffusion and/or Brownian motion of phases present in the colloid but does not result in rearrangement of phases as described herein (e.g., until the temperature reaches a critical temperature as described in more detail below).

Figure 3C:
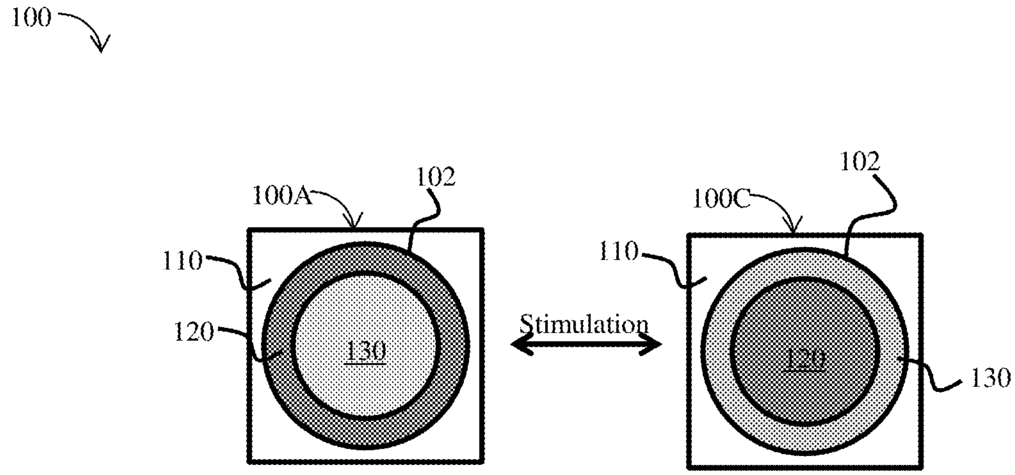
FIGS. 3C-3F are schematic drawings illustrating changing the arrangement of colloid droplet phases, according to one set of embodiments.

Referring to FIG. 3C, in some embodiments, colloid 100 comprises an outer phase 110, and a plurality of droplets (shown as exemplary droplet 102) comprising a first component 120 and a second component 130 at least partially encapsulated by the first component (configuration 100A). In certain embodiments, colloid 100 having configuration 100A may be stimulated (e.g., by a first stimulus) such that at least a portion of the plurality of droplets obtain a second configuration 100C, such that second component 130 at least partially encapsulates first component 120. That is to say, in certain embodiments, the first component and the second component may transpose. In some embodiments, the rearrangement between the first configuration and the second configuration may be reversible. For example, in some cases, colloid 100 comprising a plurality of droplets having second configuration 100C may be stimulated (e.g., by a second stimulus) such that at least a portion of the plurality of droplets return to first configuration 100A.

Figure 3D:
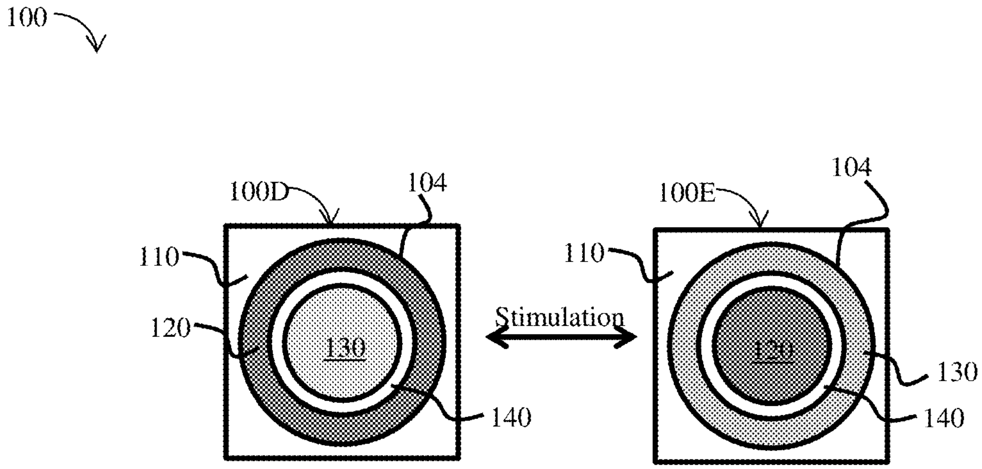

In some embodiments, the colloid comprises a plurality of droplets comprising three or more components. In some such embodiments, the colloid may be stimulated such that two or more of the three of more components change arrangement. In an exemplary embodiment, a colloid comprises a plurality of droplets comprising a first component at least partially encapsulating a second component, the second component at least partially encapsulating a third component, and upon stimulation, the first component changes arrangements with the second and/or third components. For example, as illustrated in FIG. 3D, colloid 100 may comprise outer phase 110 and a plurality of droplets (shown as exemplary droplet 104) comprising a first component 120, a second component 130, and a third component 140. In certain embodiments, the third component at least partially encapsulates the second component, and the first component at least partially encapsulates the second and third components. In certain embodiments, colloid 100 having configuration 100D may be stimulated (e.g., by a first stimulus) such that at least a portion of the plurality of droplets obtain a second configuration 100E, such that the second component at least partially encapsulates the first and third components. In some embodiments, the rearrangement between configuration 100D and 100E are reversible. For example, in some cases, colloid 100 comprising a plurality of droplets having configuration 100E may be stimulated (e.g., by a second stimulus) such that at least a portion of the plurality of droplets return to configuration 100D.

In certain embodiments, the colloid may be stimulated such that two or more components become miscible. Referring now to FIG. 3F, in some embodiments, the colloid comprises outer phase 110, and a plurality of droplets (shown as exemplary droplet 108) comprising a first component 120 and a second component 130 at least partially encapsulated by the first component (configuration 100A). In certain embodiments, colloid 100 having configuration 100A may be stimulated (e.g., by a first stimulus) such that at least a portion of the plurality of droplets obtain a second configuration 100F, such that the first component and the second component form a miscible mixture 125. Those skilled in the art would understand that droplets comprising two or more, three or more, or four or more components may, upon stimulation, have two or more, three or more, or four or more components form a miscible mixture.

In some cases, the colloid may comprises two or more miscible components that, upon stimulation, become immiscible. Referring again to FIG. 3F, in certain embodiments, the colloid having a plurality of droplets comprising mixture 125 such that (configuration 100F), upon stimulation, the mixture separates into first component 120 and second component 130, at least partially encapsulated by first component 120 (configuration 100A).

While exemplary configurations for a plurality of droplets having two or more components, are described above, those skilled in the art would understand based upon the teaching of this specification that additional reconfigurations and rearrangements are also possible (e.g., the third component encapsulating the first and second components, etc.). Those skilled in the art would also understand, based upon the teachings of this specification, that droplets comprising four or more, five or more, or six or more components are also possible and that such droplets may also be stimulated such that two or more of the components rearrange.

Those skilled in the art will understand that while much of the specification refers to a plurality of droplets, the colloid may comprises an outer phase and a plurality of regions comprising two or more components, such that the two or more components change configuration (e.g., after stimulation).

In some cases, the methods and colloids described herein may be useful for the formation of Janus droplets. For example, in certain embodiments, the first component and second component may change configuration upon stimulation such that neither component encapsulates the other component in the new configuration. In some such embodiments, the colloid may comprise a plurality of Janus droplets. In some such embodiments, the colloid is stimulated such that the plurality of droplets form Janus droplets.

Figure 3E:
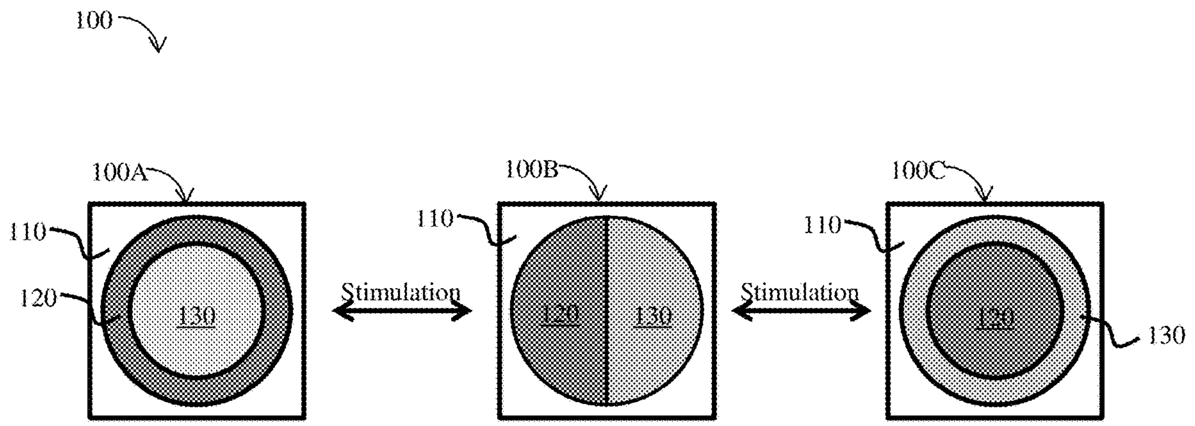
Figure 3F:
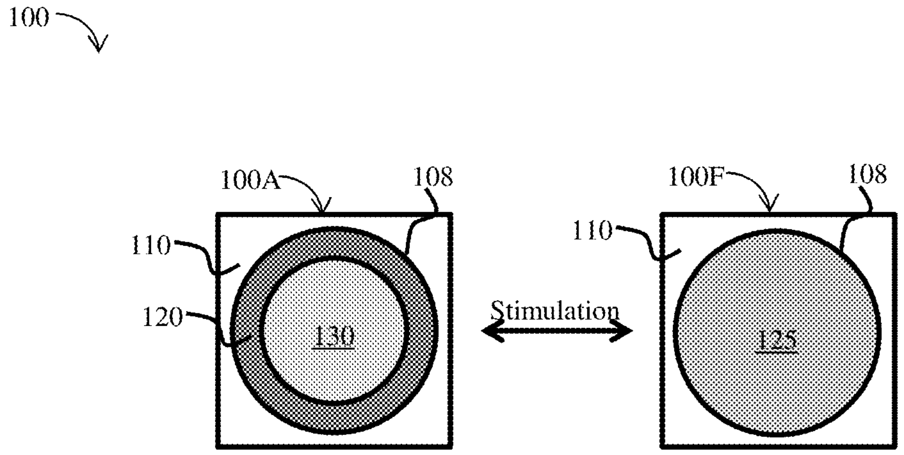

For example, as shown in FIG. 3E, second configuration 100B may comprise a Janus droplet. That is to say, in certain embodiments, the two or more components do not encapsulate each other but interface with the outer phase to form Janus droplets. Janus droplets are generally known in the art and comprise droplets wherein the droplet is divided into two distinct parts comprising two different components. For example, in some embodiments, the emulsion comprises an outer phase and a plurality of droplets comprising a first component and a second component, wherein the plurality of droplets are Janus droplets.

In some embodiments, colloid 100 may, upon stimulation, change configuration from first configuration 100A, to an intermediate configuration 100B. In some cases, colloid 100 may reversibly return (upon a second stimulation) to first configuration 100A, or obtain third configuration 100C. In certain embodiments, the change in configuration between configuration 100A and configuration 100B, or between configuration 100C and configuration 100B, is reversible. That is to say, in some embodiments, colloid 100 may change arrangement from the second configuration and/or the third configuration to the first configuration in the presence of a second stimulus, different than a first stimulus.

The first stimulus and the second stimulus may be the same type of stimulus (e.g., light, heat, force, an analyte, an acid) but differ in a property of the stimulus (e.g., different intensities of light, different magnitudes of temperature change, different magnitudes of force, different analytes, different analyte concentrations). In an exemplary embodiments, the first stimulus may be an analyte present at a first concentration, and the second stimulus comprises the analyte present in a second concentration, less than the first concentration (e.g., the degradation of an analyte below a particular concentration results stimulates the colloid).

In some cases, the first stimulus and the second stimulus may be different (e.g., a different type of stimulus, a different property of the stimulus).

An exemplary screening test for determining suitable stimuli includes preparing a colloid having a plurality of droplets comprising a first component and a second component at least partially encapsulated by the first component. The second component further comprises a dye (miscible in the outer phase but not present in the outer phase), dispersed within the second component, the dye being immiscible and not dispersed within the first component. Upon adding or exposing the colloid to the stimulus, as described herein, the first component and second component rearrange such that the second component at least partially encapsulates the first component and the dye is observed in the outer phase.

The colloid may be stimulated for any suitable amount of time. For example, in some cases, the stimulus is added to the colloid and not removed. In certain embodiments, the stimulus is applied for a specific amount of time. In some such embodiments, the stimulus may be applied for between about 1 second and about 10 seconds, between about 5 seconds and about 60 seconds, between about 30 seconds and about 2 minutes, between about 1 minute and about 5 minutes, between about 2 minutes and about 10 minutes, between about 5 minutes and about 15 minutes, between about 10 minutes and about 30 minutes, between about 15 minutes and about 60 minutes, between about 30 minutes and about 2 hours, between about 1 hour and about 6 hours, or between about 2 hours and about 24 hours. In some cases, the colloid may be stimulated for greater than 24 hours.

In certain embodiments, the second stimulus is the removal of the first stimulus. That is to say, in some embodiments, the two or more components in the plurality of droplets have a first configuration and change arrangement in the presence of a first stimulus to a second configuration. In some such embodiments, the two or more components may return to the first configuration upon removal of the first stimulus. Stimuli are described in more detail, below. The term component, as used herein, generally refers to a portion of a droplet comprising a group of substantially similar molecules, a group of substantially similar compounds, and/or a phase (e.g., a non-aqueous phase, an aqueous phase) comprising such molecules and/or compounds. Those skilled in the art would understand that the term component is not intended to refer to a single molecule or atom. In some embodiments, the component is a liquid phase (e.g., a gas phase, an aqueous phase, non-aqueous phase) comprising a group of substantially similar compounds and/or molecules. For example, in some cases, each component may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more components present within each droplet.

In some embodiments, the plurality of droplets comprise two or more components (e.g., three or more components, four or more components, five or more components) such that at least two of the two or more components change configuration in the presence of a stimulus. In some cases, the two or more components may be substantially miscible over a range of temperatures (e.g., below a critical temperature of the two or more components, above a critical temperature of the two or more components). In some cases, the two or more components may also be substantially immiscible over a different range of temperatures (e.g., above the critical temperature of the two or more components, below the critical temperature of the two or more components) than the range of temperatures over which they are miscible.

In some embodiments, the two or more components may be selected such that the interfacial tension between the two or more components allows for slight changes in interfacial tension (e.g., in response to a stimulus that changes the conformation and/or a property of the one or more components) to change the configuration of the two or more components within at least a portion of the plurality of droplets. The morphology of the plurality of droplets is generally controlled by interfacial tension between two or more components within the droplets. For example, a complex emulsion of any immiscible liquids F and H (at a given volume ratio) in a third immiscible liquid W has interfacial tensions of the H-W interface, $\gamma_H$, the F-W interface, $\gamma_F$, and the F-H interface, $\gamma_{FH}$. In some cases, $\gamma_F$ and $\gamma_H$ may be greater than $\gamma_{FH}$ such that combinations of liquids H and F have low interfacial tension just below a critical temperature of the two liquids.

Figure 3G:
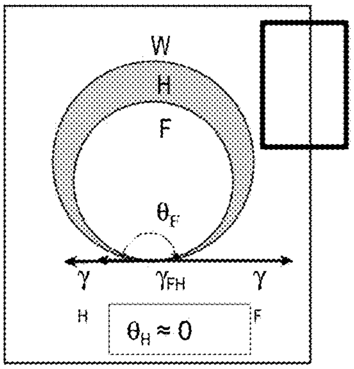
FIG. 3G is a schematic of the effect of interfacial tensions on the configuration of a complex droplet where encapsulation of a fluorocarbon (F) by a hydrocarbon (H) in water (W) is favored, according to one set of embodiments.
Figure 3H:
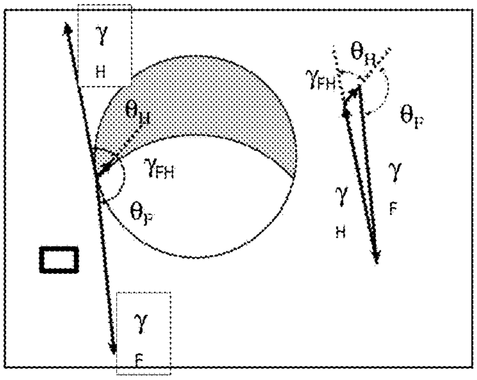
FIG. 3H is a schematic of the effect of interfacial tensions on the configuration of a complex droplet where the formation of a Janus droplet of a fluorocarbon (F) and a hydrocarbon (H) in water (W) is favored, according to one set of embodiments.
Figure 3I:
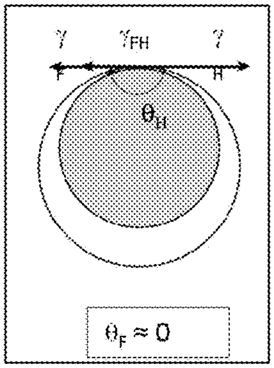
FIG. 3I is a schematic of the effect of interfacial tensions on the configuration of a complex droplet where encapsulation of a hydrocarbon (H) by a fluorocarbon (F) in water (W) is favored, according to one set of embodiments.

Generally, such multi-phase droplets may have equilibrium spherical shapes and may exhibit, for example, thermodynamically-permissible internal configurations including (1) liquid H completely engulfs liquid F (FIG. 3G), (2) liquids H and F form a Janus droplet (FIG. 3I), and (3) liquid F completely engulfs liquid H (FIG. 3H). These droplet configurations may be characterized, in some cases, by two contact angles, $\theta_H$ between the H-W and F-H interfaces, and $\theta_F$ between the F-H and F-W interfaces. The three interfacial tensions acting along the interfaces must be in equilibrium for the droplet configuration to be stable as can be expressed by the following equations:

$$\cos\theta_H = \frac{\gamma_F^2 - \gamma_H^2 - \gamma_{FH}^2}{2\gamma_{FH}\gamma_H}$$

-continued $$\cos\theta_F = \frac{\gamma_H^2 - \gamma_F^2 - \gamma_{FH}^2}{2\gamma_{FH}\gamma_F}$$

In some cases, $\theta_H$ approaches 0 and $\theta_F$ approaches 0, yielding the following two relationships:

$$\theta_H = 0 \Rightarrow \gamma_F = \gamma_H + \gamma_{FH}$$

$$\theta_F = 0 \Rightarrow \gamma_F = \gamma_H + \gamma_{FH}$$

These equations generally indicate that when $\gamma_F - \gamma_H \geq \gamma_{FH}$, the droplets can rearrange to configuration (1) in FIG. 2A. Conversely, when $\gamma_H - \gamma_F \geq \gamma_{FH}$, the droplets can rearrange to configuration (3) in FIG. 2C. However, when the difference between $\gamma_H$ and $\gamma_F$ is on the order of $\gamma_{FH}$, the droplets can rearrange to a Janus droplet geometry associated with configuration (2) in FIG. 3H. As such, slight changes in the balance of $\gamma_H$ and $\gamma_F$ may induce changes in the droplet's morphology. In some embodiments, the two or more components may be selected such that changes in the balance of $\gamma_H$ and $\gamma_F$ result in the reversible change of configuration of the two or more components within a portion of the plurality of droplets.

Those skilled in the art would be capable of selecting suitable components such that the components have a first configuration (i.e. arrangement) in the absence of a stimulus and a second configuration (i.e. arrangement) in the presence of the stimulus. In some embodiments, the components have a first configuration (i.e. arrangement) in the presence of a first stimulus and a second configuration (i.e. arrangement) in the presence of a second stimulus.

The term stimulating as used herein generally refers to the addition, removal, or change of a condition, a compound, or the environment (e.g., temperature, pressure, pH) such that the interfacial tension between two or more components is changed. Those skilled in the art will be capable of selecting suitable stimulus for use with the colloid described herein based upon the teachings of the specification and will understand stimulation does not comprise substantially removing a component and/or replacing the entirety of a component with a new component. However, in some embodiments, stimulating the colloid may result in a component, additional compound, and/or surfactant present in the colloid changing molecular conformation such that the component, additional compound, and/or amphiphilic compound is chemically distinguishable after stimulation (e.g., an acid cleavable component, additional compound, and/or amphiphilic compound that cleaves in the presence of an acid, a photosensitive component, additional compound, and/or amphiphilic compound that changes conformation or molecular structure after exposure to light) as compared to before stimulation. In certain embodiments, stimulating the colloid may result in a change in interfacial tension between two or more components such that the two or more component rearrange and/or mix.

In some embodiments, stimulating the colloid changes the arrangement of the colloid, as described herein. For example, in certain embodiments, stimulating the colloid changes the molecular conformation of at least one of the two or more components. In certain embodiments, stimulating the colloid releases at least one of the two or more components, additional compounds, and/or amphiphilic compounds, from a portion of the plurality of droplets. In some embodiments, stimulating the colloid changes an average birefringence of the colloid (e.g., increases the birefringence, decreases the birefringence). In certain embodiments, stimulating the colloid changes the color of the colloid and/or changes an average optical transmission of the colloid. In some cases, stimulating the colloid may change an average luminesce of the colloid. In certain embodiments, stimulating the colloid may change an average density of the colloid.

Those skilled in the art would understand that changing a property of a colloid refers to a property of the colloid immediately before that differs in a substantially measurable way from the property of the colloid at some relatively short time (e.g., seconds, minutes, hours) after stimulation. Those skilled in the art would also be capable of selecting methods for determining the change in the property of the colloid (e.g., measuring the average birefringence, measuring the optical transmission, measuring the density, etc.) based upon the specification and examples below.

In some embodiments, stimulating the colloid comprises exposing the colloid to an external stimulus (e.g., such that the configuration of two or more components is changed). In some such embodiments, the external stimulus comprises electromagnetic radiation, ionizing radiation, a magnetic field, an electric field, a mechanical force (e.g., pressure, direct contact), or combinations thereof. Those skilled in the art would be capable of selecting suitable components and methods of applying such external stimuli based upon the teachings of the specification and examples below. For example, in some such embodiments, at least one of the two or more components may comprise a magnetic particle such that, in the presence of a magnetic field, the at least one of the two or more components transposes or changes configuration with at least one additional component of the two or more components.

Figure 7A:
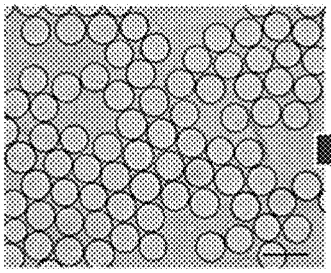
FIGS. 7A-7F show image processing based of Janus droplets upon exposure to an analyte, according to one set of embodiments.
Figure 7B:
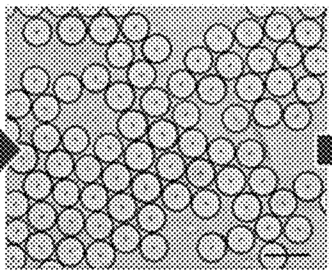

In certain embodiments, the external stimulus comprises photochemical stimulation (e.g., exposing the colloid to light). The light may comprise any suitable wavelength, including but not limited to radio waves (e.g., a wavelength between about 1 cm and about 100 m), infrared light (e.g., a wavelength between about 700 nm and about 1 cm), visible light (e.g., a wavelength between about 400 nm and about 700 nm), ultraviolet (UV) light (e.g., a wavelength between about 10 nm and about 400 nm), and x-rays (e.g., a wavelength between about 0.01 nm and about 10 nm). For example, in some embodiments, at least one of the two or more components comprises a light-sensitive surfactant (e.g., azobenzene) such that the light-sensitive surfactant reversibly changes molecular confirmation in the presence of UV light and/or visible blue light, causing the at least one component to transpose or change configuration with at least one additional component (FIG. 7B).

In some embodiments, stimulating the colloid comprises changing the temperature of the colloid (e.g., such that the configuration of two or more components is changed). In certain embodiments, changing the temperature of the colloid comprises heating the colloid. In some embodiments, changing the temperature of the colloid comprises cooling the colloid. In some embodiments, the colloid is at a first temperature, below a critical upper consolute temperature of two or more components, and the temperature is increased to a second temperature above the critical upper consolute temperature of the two or more components such that two or more of the two or more components change configuration. Those skilled in the art would be capable of selecting suitable methods of heating or cooling the colloid based upon the teaching of the specification and examples below.

In certain embodiments, stimulating the colloid comprises applying a force and/or pressure to the colloid such that the configuration of two or more components is changed.

In some embodiments, stimulating the colloid comprises adjusting the ionic strength and/or adjusting the pH of the colloid. For example, in some embodiments, adjusting the pH of the colloid comprises adding an acid (e.g., HCl) or a base (e.g., NaOH). For example, in some such embodiments, at least one of the two or more components comprises a pH-sensitive surfactant (e.g., N-dodecylpropane-1,3-diamine) and/or an acid-cleavable surfactant (e.g., sodium 2,2-bis(hexyloxy)propyl sulfate) such that the pH-sensitive surfactant and/or the acid-cleavable surfactant changes charge and/or cleaves in the presence of an acid or a base, causing the at least one component to transpose or change configuration with at least one additional component.

In certain embodiments, stimulating the colloid comprises adding an analyte to the colloid. The analyte may comprise any suitable material (e.g., a vapor analyte, a liquid analyte, a solid analyte) such that the incorporation of the analyte into a portion of the plurality of droplets or the outer phase causes the two or more components to change configuration. Those skilled in the art would be capable of selecting analytes and components suitable for colloid based upon the teaching of the specification and the examples below. Non-limiting examples of suitable analytes includes a biological compound, a drug, a macromolecule, a salt, an electrolyte, an enzyme, a nucleic acid, a carbohydrate, a peptide, a protein, a lipid, a phosphate, a sulfonate, a virus, a pathogen, an oxidant, a reductant, a toxin, a chemical warfare agent, an explosive, carbon dioxide, a surfactant, or combinations thereof. Components can be selected such that two or more components have a first interfacial tension in the absence of an analyte, and a second interfacial tension in the presence of the analyte such that the configuration of the two or more components is different in the presence of the analyte than in the absence of the analyte.

In an exemplary embodiment, an enzyme may be added to the colloid comprising a plurality of droplets such that the enzyme interacts with one or more of the components, additional compounds, and/or amphiphilic compounds present in the plurality of droplets. In some such embodiments, the enzyme may interact with the component, additional compound, and/or amphiphilic compound (e.g., such as a surfactant which cleaved in the presence of the enzyme) such that the two or more components change configuration, as described herein.

In another exemplary embodiment, one or more components may comprise an additional compound such as a surfactant that is capable of interacting with a biological analyte. Non-limiting examples of biological analytes include glucose, cholesterol, triglycerides, and bilirubin. In some such embodiments, the colloid may reversibly change arrangement of two or more components in the presence of a biological analyte such that the change in arrangement can be detected (e.g., by optical transmission). In certain embodiments, the colloid changes arrangement at a particular critical concentration of the biological analyte.

In some embodiments, stimulating the colloid causes a chemical transformation of one or more components present in the colloid such that two or more components change configuration. Non-limiting examples of chemical transformations which may result in two or more components changing configuration include enzymatic degradation, enzymatic synthesis, ionization, cleavage, coupling, hybridization, aggregation, hydrolysis, isomerization, reduction, oxidation, and host-guest interactions of one or more components (or component materials such as a surfactant). Other chemical transformations are also possible. In some embodiments, a portion of the plurality of droplets can be solidified (e.g., polymerized) such that a first configuration, a second configuration different than the first configuration, and/or a Janus droplet configuration solid droplets can be fabricated. Those skilled in the art will be capable of selecting appropriate materials for solidifying droplets and may include, in some embodiments, adding a crosslinker (e.g., a fluorinated acrylate) to the colloid such that the crosslinker crosslinks at least one of the two or more components, wherein the at least one of the two or more components comprises a crosslinkable polymer. In certain embodiments, solidifying droplets comprises adding a gelling agent (e.g., calcium-crosslinked alginate, gelatin, agar, or the like). In some embodiments, solidifying droplets comprises drying the droplets. In certain embodiments, solidifying droplets comprises changing the temperature such that one or more components solidify (e.g., a component comprising a liquid crystal or liquid crystal polymer that solidifies below the new temperature, a component comprising a liquid with a relatively high freezing point such that changing the temperature solidifies the liquid). Other methods of solidifying droplets are also possible and are known in the art.

Colloids described herein may be formed using any suitable method. For example, in some embodiments, an outer phase material, a first component, and a second component are mixed and emulsified, forming an outer phase and a plurality of droplets in the outer phase having a first component and a second component at least partially encapsulated by the first component. Suitable methods for emulsifying the fluid are known in the art and may comprise sonication, high shear mixing, shaking, passing the fluid through a membrane, or injecting the two or more components into the outer phase through a small diameter channel.

In certain embodiments, the outer phase material, the first component, and the second component may be mixed at a temperature at which the first component material and the second component material are miscible. In some such embodiments, the temperature of the mixture may be changed (e.g., increased, decreased) to a temperature such that the first component and the second component are immiscible and form a plurality of droplets in the outer phase having a first component and a second component at least partially encapsulated by the first component. While much of the description herein applies to two components, those skilled in the art would understand that such methods may be useful for the formation of colloids comprising a plurality of droplets having three or more, four or more, or five or more components.

The colloids described herein may be useful in a number of applications. In an exemplary embodiment, the colloids described herein may be used for sensing of an analyte. For example, in some such embodiments, two or more phases in the colloid may change arrangement in the presence of an analyte such that the change in arrangement can be detected (e.g., by a change in optical transmission, birefringence, etc. of the colloid). In another exemplary embodiment, the colloids described herein may be used as tunable lenses. In certain embodiments, measurements of the optical properties (e.g., transmission, absorption, reflection, focal distance, and scattering) of either individual droplets or of the bulk colloid can be indicative of specific droplet arrangements. For example, when a change in droplet arrangement is correlated with an analyte of interest (i.e., enzyme, pollutant, virus, etc.), then, the colloids can be used as sensors in which an optical measurement serves as a readout mechanism of the presence of the analyte. In certain embodiments, for systems in which there is a change in an analyte of interest over time (e.g., progress of a chemical reaction, such as degradation of a chemical by an enzyme over time), tracking of the changes in optical properties of the colloid over time can be used to, for example, analyze reaction rates or analyte concentrations. In some such embodiments, the arrangement of the components of the colloid changes in the presence of a stimulus such that the colloid obtains a transparent state over a particular range of time.

In yet another exemplary embodiment, the colloids described herein may be used for release of a macromolecule such as an active pharmaceutical ingredient or biomolecule (e.g., insulin). For example, in some such embodiments, the colloid comprising a plurality of droplets having two or more components may comprises an active pharmaceutical ingredient or biomolecule miscible and present within one of the components at least partially encapsulated by another component. In the presence of an analyte (e.g., glucose), two or more components may change arrangement such that the component containing the active pharmaceutical ingredient or biomolecule at least partially encapsulates the remaining components and the active pharmaceutical ingredient or biomolecule is released into the outer phase.

As used herein, the term "active pharmaceutical ingredient" (also referred to as a "drug") refers to an agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients include, without limitation, agents listed in the United States Pharmacopeia (USP), Goodman and Gilman's The Pharmacological Basis of Therapeutics, 10th edition, McGraw Hill, 2001; Katzung, B. (editor), Basic and Clinical Pharmacology, McGraw-Hill/Appleton & Lange, 8th edition (Sep. 21, 2000); Physician's Desk Reference (Thomson Publishing); and/or The Merck Manual of Diagnosis and Therapy, 17th edition (1999), or the 18th edition (2006) following its publication, Mark H. Beers and Robert Berkow (editors), Merck Publishing Group, or, in the case of animals, The Merck Veterinary Manual, 9th edition, Kahn, C. A. (ed.), Merck Publishing Group, 2005. Preferably, though not necessarily, the active pharmaceutical ingredient is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In certain embodiments, the active pharmaceutical ingredient is a small molecule. Exemplary active pharmaceutical ingredients include, but are not limited to, anti-cancer agents, antibiotics, antiviral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, prostaglandins, etc.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

In some embodiments, a portion of the plurality of droplets can be solidified (e.g., polymerized) such that a first configuration, a second configuration different than the first configuration, and/or a Janus droplet configuration solid droplets can be fabricated. Those skilled in the art will be capable of selecting appropriate materials for solidifying droplets and may include, in some embodiments, adding a crosslinker (e.g., a fluorinated acrylate) to the colloid such that the crosslinker crosslinks at least one of the two or more component, wherein the at least one of the two or more component comprises a crosslinkable polymer. In certain embodiments, solidifying droplets comprises adding a gelling agent (e.g., calcium-crosslinked alginate, gelatin, agar, or the like). In some embodiments, solidifying droplets comprises drying the droplets. In certain embodiments, solidifying droplets comprises changing the temperature such that one or more components solidify (e.g., a component comprising a liquid crystal or liquid crystal polymer that solidifies below the new temperature, a component comprising a liquid with a relatively high freezing point such that changing the temperature solidifies the liquid). Other methods of solidifying droplets are also possible and are known in the art.

The plurality of Janus particles may have any suitable average cross-sectional dimension. In some embodiments, the average cross-sectional dimension of the plurality of Janus particles is greater than or equal to 400 nanometers, greater than or equal to 500 nanometers, greater than or equal to 600 nanometers, greater than or equal to 800 nanometers, greater than or equal to 1 micron, greater than or equal to 2 microns, greater than or equal to 5 microns, greater than or equal to 10 microns, greater than or equal to 20 microns, greater than or equal to 30 microns, greater than or equal to 50 microns, greater than or equal to 60 microns, greater than or equal to 75 microns, greater than or equal to 100 microns, greater than or equal to 150 microns, greater than or equal to 200 microns, greater than or equal to 300 microns, or greater than or equal to 400 microns. In certain embodiments, the average cross-sectional dimension of the plurality of Janus particles may be less than or equal to 500 microns, less than or equal to 400 microns, less than or equal to 300 microns, less than or equal to 200 microns, less than or equal to 150 microns, less than or equal to 100 microns, less than or equal to 75 microns, less than or equal to 60 microns, less than or equal to 50 microns, less than or equal to 20 microns, less than or equal to 10 microns, less than or equal to 5 microns, less than or equal to 2 microns, less than or equal to 1 micron, less than or equal to 800 nanometers, less than or equal to 600 nanometers, or less than or equal to 500 nanometers. Combinations of the above-referenced ranges are possible (e.g., greater than or equal to 400 nanometers and less than or equal to 500 microns, greater than or equal to 400 nanometers and less than or equal to 100 microns, greater than or equal to 30 microns and less than or equal to 200 microns). Other ranges are also possible.

EXAMPLES

The following examples illustrate embodiments of certain aspects of the invention. It should be understood that the methods and/or materials described herein may be modified and/or scaled, as known to those of ordinary skill in the art.

Example 1

The following example describes the general formation of an emulsion. For example, hydrocarbon and fluorocarbon liquids were heated until miscible and emulsified. The temperature required varied depending on the solutions. Solutions were emulsified either in bulk by shaking or by coaxial glass capillary microfluidics and cooled to induce phase separation. For hexane-perfluorohexane emulsions, the emulsions were chilled on ice prior to imaging and often imaged while immersed in a cool water bath to maintain a temperature below 20° C. For microfluidics, syringe pumps were used to inject the outer phase and inner phase using a glass capillary microfluidic device made from an outer square capillary and inner cylindrical capillary pulled to a 30 μm tip using a Micropipette Puller (Sutter Instrument Company). The microfluidic setup was heated above the $T_c$ of the inner phase solution using a heat lamp. Emulsions were then cooled below $T_c$ to induce phase separation. Emulsions were observed to be stable during the time periods used (e.g., on the order days).

Example 2

The following example describes the formation of an emulsion. According to the methods described in Example 1.

Figure 10:
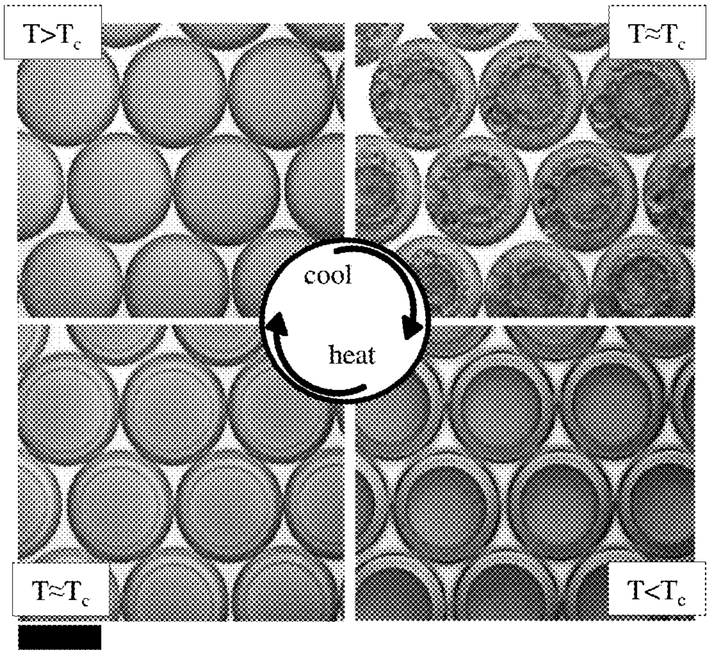
FIG. 10 shows photographs of the formation of complex emulsions comprising hexane and perfluorohexane, according to certain embodiments.
Figure 11A:
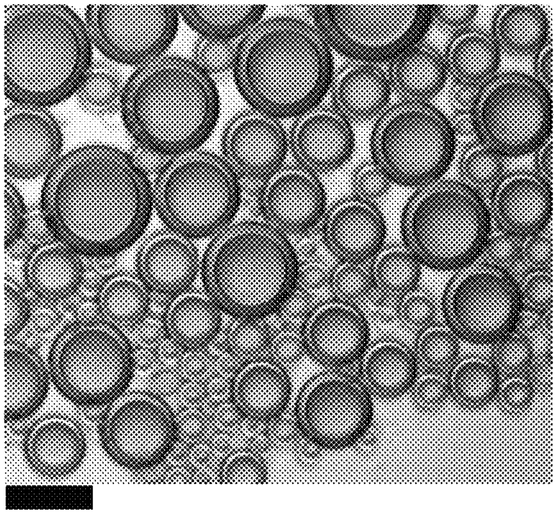
FIG. 11A shows photographs of a complex emulsion comprising hexane and perfluorohexane, formed according to one set of embodiments.
Figure 11B:
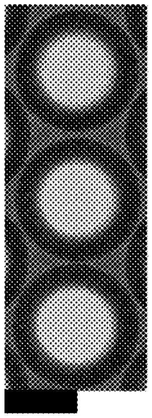
FIG. 11B shows a photograph of a complex emulsion comprising hexane and perfluorohexane, formed according to one set of embodiments.

Fluorocarbons are generally lipophobic as well as hydrophobic and many fluorocarbon and hydrocarbon liquids are immiscible at room temperature but have a low upper consolute temperature ($T_c$) and mix with gentle heating. Hexane and perfluorohexane, for example, have a $T_c$ of 22.65° C. A 1:1 volume ratio of hexane and perfluorohexane was mixed and emulsified above $T_c$ in an aqueous solution of Zonyl FS-300 fluorosurfactant (FIG. 10, top left). Cooling below $T_c$ induced phase separation and yielded structured complex droplets (FIG. 2. Bottom right). Above $T_c$, hexane and perfluorohexane are miscible and emulsified in 0.1% Zonyl (FIG. 10, top left). Below $T_c$, hexane and perfluorohexane phase separate to create a hexane-in-perfluorohexane-in-water (H/F/W) double emulsion (FIG. 10, bottom right). This phase separation was reversible. These complex emulsions were readily produced in bulk by shaking warm hexane-perfluorohexane liquid in a surfactant solution (FIG. 11A). Although these droplets were polydisperse, the morphology and composition of the droplets was highly uniform. Chemical partitioning during phase separation gave directed compartmentalization of solutes (FIG. 11B), forming hexane/perfluorohexane/water double emulsion droplets in a microfluidic device. Therefore, temperature-induced phase separation of liquids provides a facile, scalable approach to fabrication of complex functional emulsions.

Example 3

The following example describes the formation of an emulsion comprising Janus droplets.

Figure 12A:
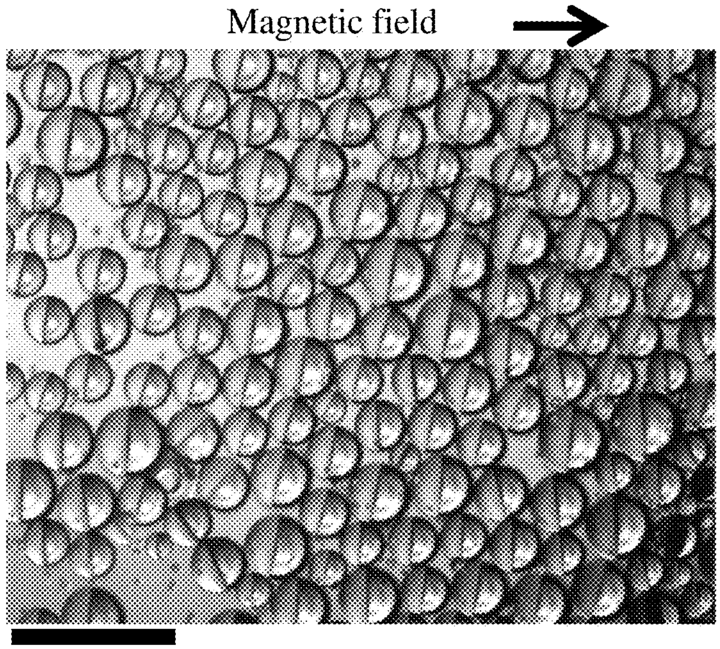
FIG. 12A shows a photograph of Janus droplets, formed according to one set of embodiments.

Liquid droplets and solid droplets with asymmetric properties were created by affecting different chemistries in the separate compartments of a fluorous-hydrocarbon Janus droplet. To create directionally-orientable and movable liquid Janus droplets, magnetic $Fe_3O_4$ nanoparticles stabilized with oleic acid were synthesized for preferential partitioning into the hydrocarbon phase. Magnetite nanoparticles were made as follows: 25 mL of concentrated NH3OH was added to an acidified solution of 1.6 g of $FeCl_3$ and 1 g of $FeCl_2 \cdot 4H_2O$ in 50 mL of water at 80° C. The magnetite nanoparticle precipitate was collected with a magnet, washed with water, and redispersed. 1 g of sodium oleate in 10 mL of water was added under stirring at room temperature. The oily black precipitate was extracted with hexanes. Solid was collected by evaporation of solvent and subsequently redispersed in dichlorobenzene. Janus droplets were obtained by heating the nanoparticle/dichlorobenzene solution and ethyl nonafluorobutyl ether above the Tc and shaking in 0.2% SDS and 0.2% Zonyl in a 2.5:1 ratio. The droplets were oriented using a neodymium magnet. Upon inclusion in a Janus emulsion of dichlorobenzene and ethyl nonafluorobutyl ether, the nanoparticle/dichlorobenzene hemispheres are rapidly oriented and move in the direction of a magnet (FIG. 12A).

Figure 12B:
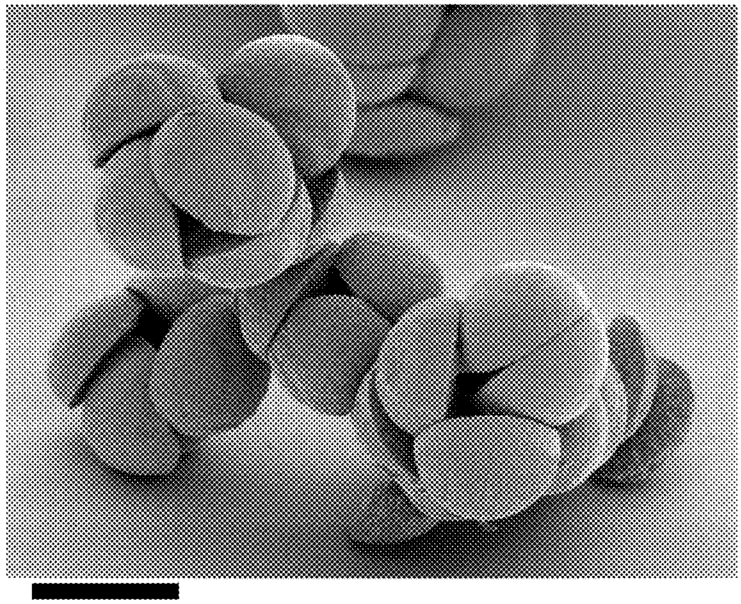
FIG. 12B shows a scanning electron micrograph of particles formed from polymerized Janus droplets, formed according to one set of embodiments.
Figure 12C:
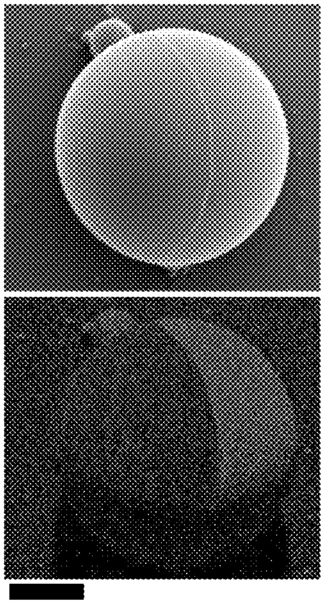
FIG. 12C shows a scanning electron micrograph (top) and an energy dispersive x-ray map highlighting fluorine (bottom) of a Janus particle, formed according to one set of embodiments.

To generate solid hemispherical droplets, an emulsion consisting of a liquid polymer precursor, 1,6-hexanediol diacrylate, as the hydrocarbon phase and methoxyperfluorobutane as the fluorous phase, was polymerized (FIG. 12B). 1-6, hexanediol diacrylate with 4% Darocur 1173 photoinitiator was heated with equal volume methoxyperfluorobutane above the Tc and emulsified. 1% SDS and 1% Zonyl in a 3:2 ratio yielded Janus droplets which were then polymerized under a UV lamp while kept cold on ice. By replacing methoxyperfluorobutane with a fluorinated acrylate oligomer and crosslinker, spherical solid Janus droplets with fluorinated and non-fluorinated sides were created (FIG. 12C).

Example 4

Figure 13:
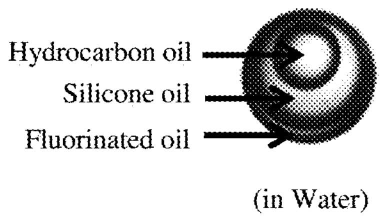
FIG. 13 shows a four-phase emulsion, formed according to one set of embodiments.

The same principles of droplet transformations observed in three-phase emulsions, and described in Example 1, were extended to a four-phase system thereby generating reconfigurable droplets of even higher order complexity. A system comprising of silicone oil (Si), hydrocarbon oil (H, mineral oil and octadecane), and fluorinated oil (F, ethyl nonafluorobutyl ether) was designed such that the liquids mixed with heating and separated into three phases at room temperature (FIG. 13). Light mineral oil with 20 wt % octadecane (used to reduce the Tc in a mixture with the other liquids), silicone oil, and ethyl nonafluorobutyl ether were used as the inner phases in a volume ratio of 6:7:13. The mineral oil and ethyl nonafluorobutyl ether both partitioned into the silicone oil such that upon phase separation, the silicone oil phase is enriched with some quantity of the two other phases. Aqueous mixtures of varying ratios of 1% Zonyl and 1% SDS were used as the outer phase, and emulsions were formed in the bulk by shaking.

Example 5

The following examples demonstrate the use of systems for the detection of analytes.

Surfactants specially designed with recognition elements to bind targeting analytes (species/molecules of interest) multivalently were synthesized. The binding interaction was able to transform a plurality of Janus droplets from an upright position to a horizontally tilted position against gravity. This transformation generated a distinct optical signal (scattering of a light beam) in the presence of analytes. The opposite response was also possible wherein a plurality of Janus droplets were pre-titled by binding to a surface or particle and is initially in a scattering position. In this case, the action of an analyte was to disrupt the linkage between the surface or particle and allow a relaxation to an upright position that allowed for reduced scattering. The optical signal could be recorded via a smartphone by for example using a QR code for binary on/off detection, using low magnification images that are processed computationally to quantify the amount of analytes in the emulsion mixture, and/or the monitoring the transmission of focused light beams through the samples. Such systems could be used in biosensor applications including aqueous liquid phase detection. The emulsions (comprising Janus droplets) with only low molecular weight surfactant molecules were relatively inexpensive to fabricate and stable over multiple weeks with no further precautions. In cases where greater emulsion stability may be required, polymeric surfactant molecules and structures could be employed. Additionally, the Janus droplets were highly selective and sensitive for detection of pathogens as, in some cases, small changes in the concentration and/or the identity of the surfactants lead to significant changes in the orientation of the Janus droplets. Janus droplets were fabricated using either bulk emulsification, which generated polydisperse droplets, or in a microfluidic device, which generated monodisperse droplets. For surfactants soluble in water, a solution containing the functionalized surfactants was used as the continuous phase. Hydrocarbon phase (such as hexane, ortho-dichlorobenzene, phthalate, etc.) and fluorocarbon phase (such as perfluorohexane, ethyl nonafluorobutyl ether, methoxy perfluorobutane) were mixed and heated over the upper critical temperature to generate the single droplet phase. When the droplet phase was dispersed into the continuous (outer) phase containing surfactants, single emulsions were generated; and upon cooling, the hydrocarbon and fluorocarbon phases separated to generate Janus droplets. The composition of each droplet was substantially similar because they were generated from the same single droplet phase. In addition, surfactants were able to be incorporated into the droplet phase. Surfactants that were not soluble in water were dissolved in the hydrocarbon phase or the fluorocarbon phase before mixing. The droplet phase containing surfactants could then be dispersed into the continuous water phase, which may contain additional surfactants and surfactant assemblies to generate the droplets. In both cases, Janus droplets were used as sensing particles with surfaces covered by with functionalized surfactants. The surfactants or surfactant assemblies could contain polymer surfactant/stabilizers or macromolecules of biological significance, including proteins, enzymes, nucleic acids, DNA, RNA.

Sensing of Pathogenic Bacteria

Figure 4A:
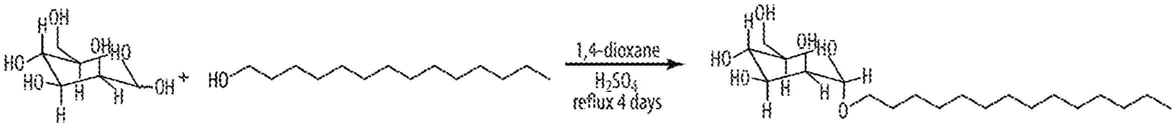
FIG. 4A shows an exemplary surfactant for use in a system including Janus droplets, according to one set of embodiments.
Figure 4B:
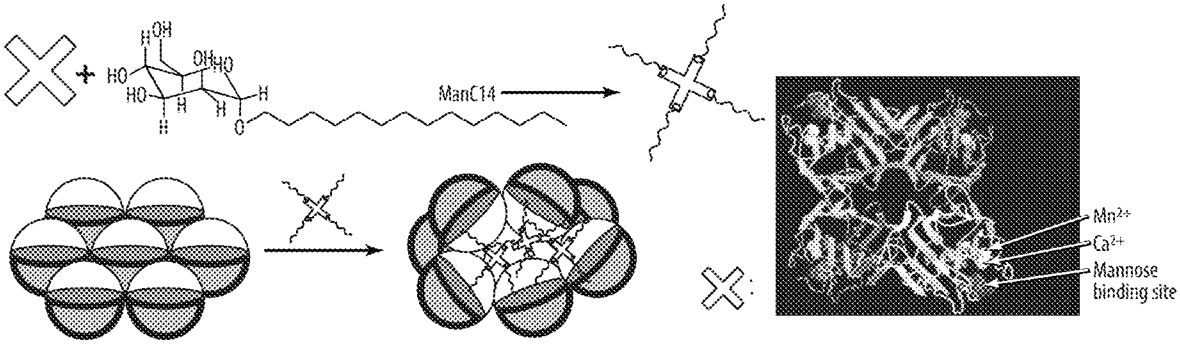
FIG. 4B shows the agglutination of a plurality of Janus droplets in the presence of analyte, according to one set of embodiments.

Our approach to detect pathogenic bacteria took advantage of the general affinity that different bacteria exhibit for specific patterns of carbohydrate. One of the targeting analytes, *Escherichia coli* (*E. coli*), is a bacterium that can be easily spread in contaminated food and water. While most strains of *E. coli* are harmless, certain strains that produce toxins could cause serious and fetal illness. To detect the *E. Coli* bacteria, surfactants were carefully designed that interact with the surfaces of the cell via the carbohydrate-lectin interaction. This weak interaction between lectin on the surfaces of *E. coli* and D-mannose typically creates a challenge to detect bacteria with high sensitivity when relying on a single interaction. Thus, a surfactant that functionalizes one phase of the Janus droplets to increase the concentration of the mannose moiety on the surface was designed. The increase in the concentration of the mannose moiety significantly enhanced binding affinity between the bacteria and the droplets, transforming a droplet into a selective sensing particle. The binding between Concanavalin A (ConA), a lectin known to bind D-mannose, was initially investigated using the Janus droplets as a model system. This technology could be relatively easily adapted for other analytes by, for example, changing the active surfactants. A novel surfactant bearing a D-mannose head group (ManC14) was synthesized (FIG. 4A). FIG. 4A shows the scheme for Mannose surfactant (ManC14) synthesis. FIG. 4B shows a schematic illustration of Janus droplets aligning with Concanavalin A (ConA). The denser perfluorohexane phase aligned at the bottom and the hexane on the top of the Janus droplets.

For this particular sensing platform, the Janus droplets were fabricated using the following method. The surfactants ManC14 and Zonyl® FS 300 (a commercially available fluorocarbon surfactant) were dissolved in a HEPES buffer solution (pH=7.5) as the continuous phase. A mixture of hexane and perfluorohexane (single droplet phase) was dispersed into the surfactant solution and cooled down to generate Janus droplets. The hexane phase on the Janus droplets was functionalized with mannose groups where the surfactant ManC14 aligned preferentially at the hexane/water interface. Without wishing to be bound by theory, due to gravity and the higher density of perfluorohexane in relative to that of hexane, Janus droplets aligned with perfluorohexane phase in the bottom (FIG. 4B). ConA was dissolved in HEPES buffer solution with final concentration of 0.5 mg $mL^{-1}$. An increasing amount of this solution (10 L to 40 L) was added to the Janus droplets; and after swirling the solution, the two-faced Janus droplets started aligning in a unique tilted configuration. The surfaces that were stabilized by ManC14 surfactant agglutinated together to form droplet complexes (FIG. 4B).

Without wishing to be bound by theory, the agglutination phenomenon occurred because ConA has four subunits, each with a binding site for mannose. This four-site binder acted similarly to an antibody that binds multiple particles and joins them together to make agglutinated droplet complexes. When Janus droplets agglutinate, the solution changes from transparent to opaque. This large and easily observable change is particularly powerful because detection events will not generally require, for example, any external power input. The Janus droplet agglutination level could be characterized both qualitatively and quantitatively as described herein.

Tuning the Surface Chemistry

Surface recognition is a general phenomenon that can be applied to many different types of methods. The use of a ligand surfactant binding with a multivalent receptor, which can be a protein, cell, or pathogen, nanoparticle was described above. This scheme can be reversed where a receptor is immobilized at the surface of a droplet and then use a multivalent ligand scaffold (natural or synthetic) to bind the Janus droplets and hold them in a tilted (scattering) state relative to the aligned non-scattering state favored by gravity. The ligands can be designed to have a lower affinity than a target analyte and hence exposure to the analyte can result in a displacement that breaks the linkage (e.g., tether) between the polyvalent ligand and the droplet. Similarly, the tether between the droplet and the ligand can be cleaved. This could be affected by an enzyme that cleaves a peptide, such as an ester or a degraded RNA. It could also be affected by catalytic or heavy metal ions or select nucleophiles (sulfides). In some cases, the ligands could be bound to a surface. It is also possible that the ligands reside on another droplet.

Individual droplets that are tilted or alternatively not tilted (aligned by gravity) can be relatively easily quantified. This gives rise to the ability to, in some cases, detect single analytes. For example, it is possible that a single molecule of DNA can be detected if the droplet is anchored to a surface by a DNA duplex. Disruption of this duplex by a complementary target DNA analyte can be observed. One aligned droplet in a sea of other tilted droplets would be readily detected. This scheme has an advantage that, for example, there would be many potential binding sites for the DNA molecule and hence thus the target DNA would not be required to find a rare binding site. Similarly, a cluster of tilted droplets in a sea of aligned droplets can be detected and, in doing so, would be able to detect a single analyte.

Detection of Agglutinated Janus Droplets

Figure 5A:
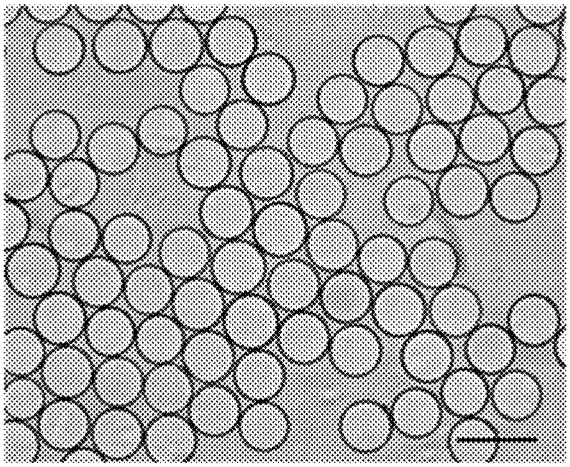
FIG. 5A shows a monodispersed plurality of Janus droplets, according to one set of embodiments.
Figure 5B:
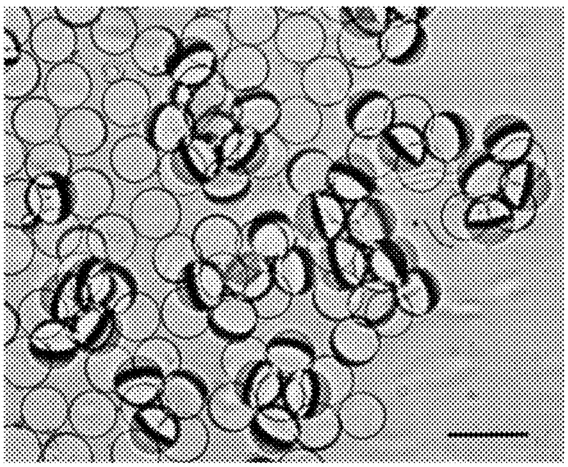
FIG. 5B shows a plurality of Janus droplets with altered orientation, according to one set of embodiments.
Figure 6A:
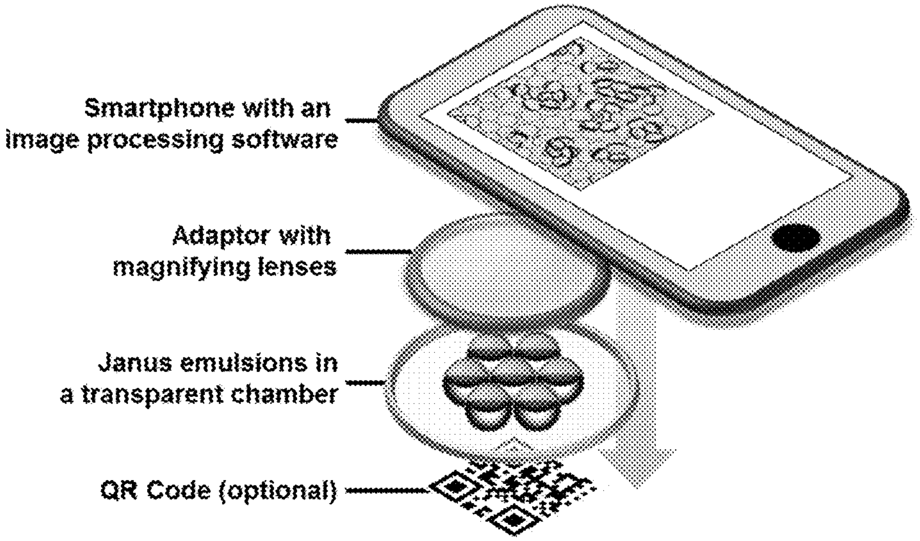
FIGS. 6A-6B show an exemplary system comprising a plurality of Janus droplets which, upon exposure to an analyte, changes an optical property of the system, according to one set of embodiments.

The solution of Janus droplets generally turns from transparent to opaque when the emulsions are agglutinated. FIG. 5A shows a solution of Janus droplets before exposure to an analyte. FIG. 5B shows a solution of Janus droplets after exposure to the analyte. Such large and easily observable differences may be incorporated into the use of image processing algorithms to analyze the optical micrographs. These optical micrographs are readily taken from, for example, any common smartphone equipped with magnifying lenses to enable low-magnification of 4× and 10× (FIG. 6A).

Figure 6B:
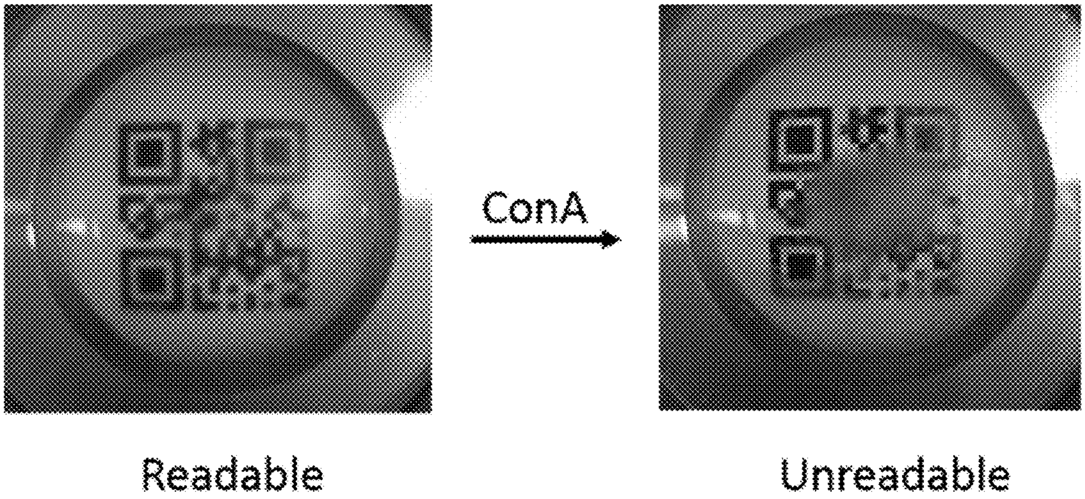

For qualitative purposes, the detection may use the significant changes in the optical transparency between pristine and agglutinated Janus droplets to generate a binary response. For example a transparent analysis chamber containing the Janus droplets was placed on top of a two-dimensional QR code, as shown in FIG. 6B. In the presence of ConA, the chamber became opaque and covered a portion of the QR code. This transformation inhibited a smartphone from reading the QR code.

Figure 7C:
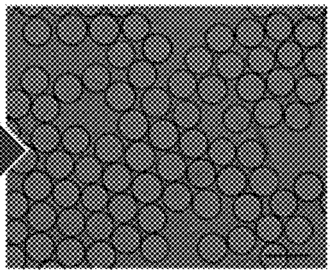
Figure 7D:
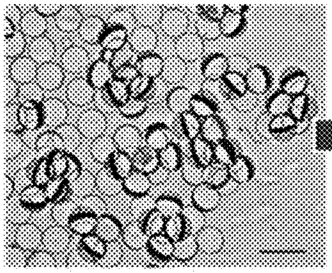
Figure 7E:
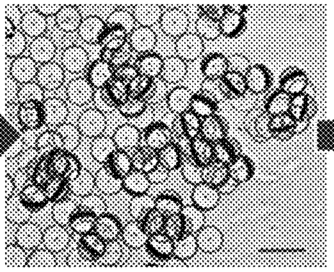
Figure 7F:
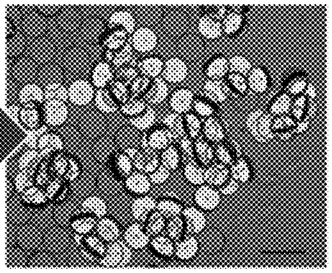
Figure 8A:
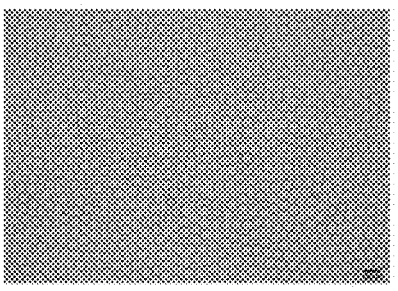
FIGS. 8A-8F show image processing based of Janus droplets upon exposure to an analyte, according to one set of embodiments.
Figure 8B:
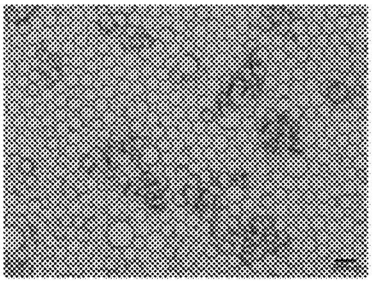
Figure 8C:
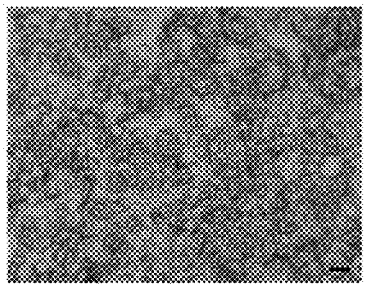
Figure 8D:
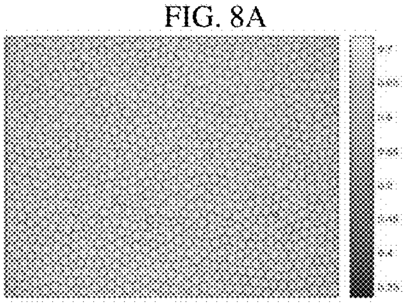
Figure 8E:
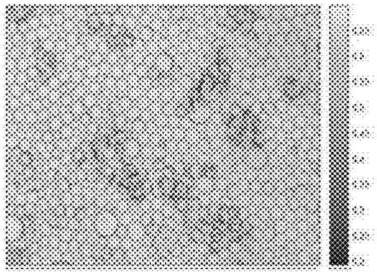
Figure 8F:
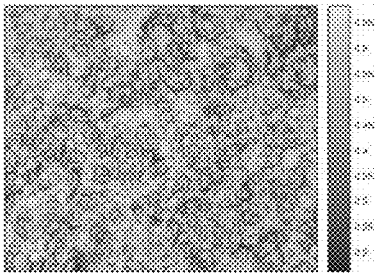

To quantify the degree of agglutination, an image processing program that calculates the percentage of area covered by agglutinated Janus droplets by two distinct logics was implemented: 1) the amount of overlapping droplets and 2) the difference in optical intensity of the images. FIGS. 7A-7C show the quantification of a plurality of Janus droplets in the absence of a targeted analyte. FIGS. 7D-7F show the quantification of a plurality of Janus droplets exposed to a targeted analyte.

Specifically, the image processing program analyzed the raw optical micrographs (FIG. 7A and FIG. 7D) by mapping out the locations of each Janus droplet and measuring their radii (FIG. 7B and FIG. 7E). Using this information, the program then sought overlapping emulsions. As described above, during agglutination the Janus droplets joined together to form droplet complexes of agglutinated Janus droplets. The program distinguished each droplet with more than two overlapping neighbors as a part of a droplet complex and rejected any droplet with zero, one, or two overlapping neighbors (FIG. 7C and FIG. 7F). The percentage of area covered by agglutinated Janus droplets were then calculated for both pristine sample (FIG. 7C) and agglutinated sample (FIG. 7F).

The area covered by these Janus droplet agglutinations were then further correlated with the analysis of optical intensity within the images. Similar to the qualitative detection, the image analysis can distinguish regions of agglutinated Janus droplets due to the lower optical transparency. The program used an adaptive thresholding algorithm to distinguish areas with higher transparency (pristine Janus droplets) from the opaque regions (agglutinated Janus droplets), FIGS. 8A-8F. The combination of the two distinct logics—identifying the overlapping Janus droplets and analyzing changes in optical intensity—can accurately detect the regions of agglutinated Janus droplets. Furthermore, the whole process can be completed within seconds from capturing the image to final calculation.

In some cases, the Janus droplets behave as individual lenses. Such droplets can be interrogated with a scanning light beam or a number of beams simultaneously. In this case (e.g., FIGS. 8A-8F), the light beams transmit through the sample and impinge on an array of light detectors. Signals can be deduced by changes in the intensity that represents the straight path of the light beam and the light that is refracted (e.g., deviating from a straight path). Without wishing to be bound my theory, lower intensity at the point of the straight path and higher intensity of light that is refracted from that path, indicate an increase in the tilt of one or more droplets. Similarly, higher intensity of light in the straight path and lower intensity that has been refracted may indicate a decrease in the tilt of the droplet. Such lensing permits detection of changes in a single droplet. For example, the ability to detect single events that can lead to the detection of single pathogens, cells, catalysts, or molecules.

Figure 9:
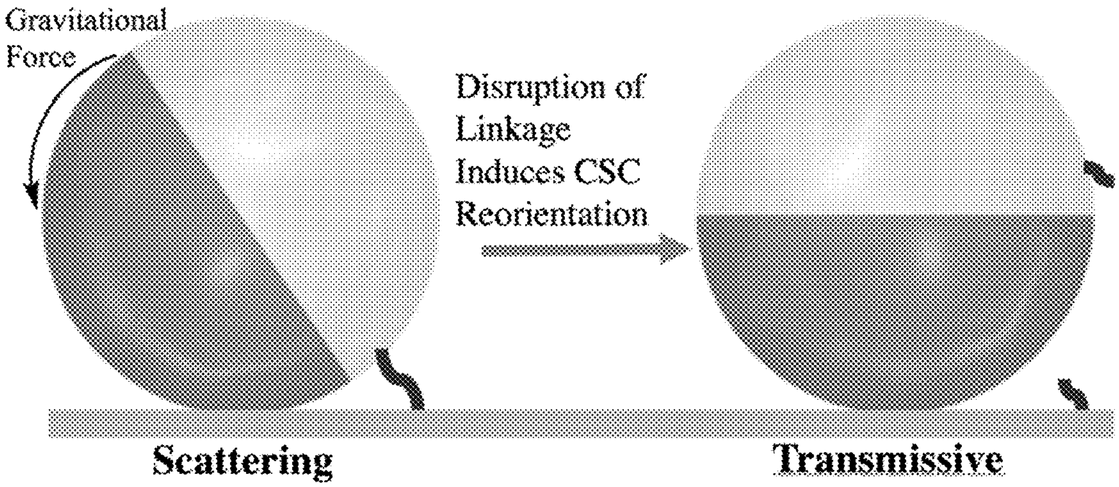
FIG. 9 shows an illustrative embodiment of interaction with an analyte resulting in the change of orientation of a Janus droplet, according to one set of embodiments.

FIG. 9 details a strategy wherein breaking a single linkage (tether) can potentially generate a sensor response that is visible to the naked eye. In this system, the red phase of the Janus droplet (CSC) had a higher density, and a gravitational force worked to orient the particles. Disrupting a chemical bond or complementary DNA interaction tehter, which has pinned the Janus droplet in a tilted scattering configuration, produced a relaxation to the transmissive equilibrium orientation. An advantage of this method is, for example, that only one droplet in a multitude of droplets need be rotated to be detected. Additionally by tethering to patterned surfaces, arrays of sensors can be produced that can detect multiple types of analytes in a single device.

Formation of Droplets

Materials. For the detection of ConA, hexane and perfluorohexane were chosen as the hydrocarbon and fluorocarbon phases respectively. In other cases, different pairs of hydrocarbon (ortho-dichlorobenzene, phthalate, etc.) and fluorocarbon (ethyl nonafluorobutyl ether, methoxy perfluorobutane, etc.) phases can be substituted to tune the upper critical temperature ($T_c$) of the mixture and the differences in density for suitable applications. For the continuous water phase, surfactants ManC14 and Zonyl® FS 300 were chosen to stabilize and generate the Janus droplets. The two surfactants were dissolved in HEPES buffer solution (pH=7.5) separately with concentration of 0.0005% and 0.01% by weight, respectively. In both bulk emulsification and microfluidics method, the final volume ratio between ManC14 solution and Zonyl FS 300 solution was kept at 1.2:1 to generate two-hemisphere Janus droplets. For surfactants that are soluble in water (such as ManC14 and Zonyl® FS 300), a solution containing the functionalized surfactants was used as the continuous phase.

Bulk emulsification for polydispersed Janus droplets. To generate Janus droplets via bulk emulsions, we began by preparing an equal-mixture of hexane and perfluorohexane with a total volume of 1 mL in a 5 mL glass vial. The mixture initially formed an immiscible solution at room temperature. The vial containing the mixture was then heated to above the $T_c$ using a standard heat gun until the mixture was miscible; for hexane-perfluorohexane mixture, the $T_c$ is 20° C. For other combinations of hydrocarbon and fluorocarbon, the $T_c$ may vary depending on the two liquids. In another 5 mL glass vial, 1 mL of the continuous phase containing ManC14 and Zonyl FS 300 (concentrations of both reported in the previous section) was also heated to the same temperature as the vial containing hexane-perfluorohexane mixture. This precaution may mitigate the phase segregation of hexane and perfluorohexane upon addition before emulsification. 50 μL of heated and miscible hexane-perfluorohexane mixture was then injected into the heated continuous phase via a pipette. The Janus droplets were then generated by shaking the vial using a vortex mixer at 3000 RPM for 5 seconds. The solution of Janus droplets was then cooled down below $T_c$ using an ice bath. This method of bulk emulsification generated polydispersed droplets with diameters ranging from 30 to 200 μm as observed by an optical microscope.

Generation of monodispersed Janus droplets via microfluidics. Both coaxial glass capillary microfluidics and commercial available microfluidic chips were used to generate emulsions. For coaxial glass capillary microfluidics, devices were made from an outer square capillary (OD=1.5 mm, ID=1.05 mm, AIT Glass) and inner cylindrical capillary (OD=1 mm, World Precision Instruments) pulled to a 30 μm tip using a P-1000 Micropipette Puller (Sutter Instrument Company). For commercial microfluidic device, Focused Flow Droplet Generator chip (channel width=100 μm, channel depth=20 μm, tip width=10 μm, glass) from Micronit was used. In both microfluidics system, Harvard Apparatus PHD Ultra syringe pumps were used to inject the outer phase (continuous phase) and inner phase (droplet phase). The flow rates were 50 μL $min^{-1}$ for the continuous phase and 30 μL $min^{-1}$ for the droplet phase. The solution of monodispersed droplets was first collected via 20 mL glass vial and later diluted with both ManC14 solution and Zonyl® solution to achieve a final droplet phase concentration of 6% by volume while maintaining the 1.2:1 volume ratio of the two surfactants. The microfluidic setup was heated above the $T_c$ of the inner phase solution using a heat lamp. Janus droplets were then cooled below $T_c$ to induce phase separation. For hexane-perfluorohexane emulsions, the emulsions were chilled on ice prior to imaging and often imaged while immersed in a cool water bath to maintain a temperature below 20° C. The average diameter of the monodispersed droplets generated from this setup were 60±10 μm. The composition of each droplet was nearly identical because each droplet was generated from the same single droplet phase.

Stability and sample storage. The Janus droplets generated from either method described above were observed to be stable on the order of weeks under room temperature. After emulsification, the Janus droplets were kept within the continuous phase at room temperature in a closed glass vial without mechanical perturbation. The diameter of the Janus droplets was not observed to change significantly after weeks of storage.

Sensing

Sample preparation for sensing of ConA. Monodispersed or polydispersed Janus droplets used for sensing experiments were fabricated using methods described above. Janus droplets were loaded into a stainless steel sample holder with a 1 cm deep well and a 1.5 cm diameter viewing window. 0.5 mL of mixed surfactant solution containing 30 μL of hexane-perfluorohexane droplet phase was loaded into sample holder to create a monolayer of Janus droplet that covered the whole viewing window. The sample holder and solution of the Janus droplets were kept below 20° C., the $T_c$ of hexane-perfluorohexane mixture, during the sensing of ConA and image acquisition.

Model system: Sensing of ConA. ConA was dissolved in HEPES buffer solution with final concentration of 0.5 mg mL- and used as the analyte. 10 μL of ConA solution was added using a micropipette to the sample holder containing Janus droplets. Solution was then swirled gently and agglutination of Janus droplets were observed within seconds. Image were recorded before and after adding ConA solution. An increasing volume (up to 40 μL) of ConA solution were added afterwards to get a correlation between agglutination level and analyte concentration. Agglutination level were analyzed both qualitatively and quantitatively as described below.

Surface Chemistry

Fabrication of DNA-functionalized surface. Glass substrates were cleaned by sonication in acetone and isopropyl alcohol for 5 min each to remove dust. After drying completely, the glass substrates were immersed in piranha solution ($H_2SO_4$:$H_2O_2$, 1:1, v/v) for 1 h, rinsed thoroughly with distilled water, and then dried under $N_2$. The glass substrates were then immersed and reacted with a toluene solution of trichlorosilane linker terminated with an N-hydroxysuccinimide (NHS) for 1 h to form NHS covalently functionalized glass substrates. Afterwards, a solution of 10 μM ssDNA dissolved in a sodium tetraborate buffer at pH 9 was reacted to form an amide bond, which attach the ssDNA onto surface of the glass slides. ssDNA was functionalized with alkyl chain to form a surfactant molecule. Janus droplets residing on the surface of ssDNA functionalized glass substrate were tilted against gravity. A solution of the complementary strand dissolved in 0.25 M NaCl solution was added to Janus droplets to hybridize the DNA strands. Janus droplets were released from the glass substrate to be aligned with gravity at areas where DNA strands were hybridized. X-ray photoelectron spectroscopy was used to analyze the elements on glass substrates to ensure successful functionalization of ssDNA.

Detection

Sample preparation for detection. For both qualitative and quantitative methods of detection, Janus droplets were imaged in a stainless steel sample holder. For qualitative detection, a two-dimensional QR code (1 cm×1 cm) was placed 1 cm below the viewing window of the analysis chamber. For quantitative detection, a white background was used instead of the QR code to provide contrast. The analysis chamber and the solution of the Janus droplets were kept in an ice bath, well below the $T_c$ of the hexane-perfluorohexane mixture to maintain the morphology of the Janus droplets.

Qualitative analysis using QR code. Qualitative analysis was performed using the QR code from unmagnified images taken from the smartphone. The distance from the phone to the analysis chamber containing the Janus droplets was approximately 10 cm. The exact distance was calibrated by the image processing software by using the known dimension of the QR code (1 cm×1 cm). The binary response measured was whether the QR code could be read via the software. If the QR code was readable, the Janus droplets were considered not agglutinated, and vice versa.

Image acquisition for quantitative analysis. To acquire the low-magnification images for quantitative analysis, an adaptor with magnifying lenses was adapted onto the smartphone. With this modification, optical micrographs with 4× and 10× magnification were obtained. The working distance from the smartphone to the analysis chamber was 1 cm. The working distance and the dimension of the images were calibrated by the calibrated marking underneath the analysis chamber with 10 μm tick marks. The image processing software then pre-processed the captured images by transforming them into greyscale images and adjusting the brightness and contrast to the reference image of blank analysis chamber. For each sample, 100 pictures were taken, forming a 10×10 array of images to span the majority of the area of the analysis chamber.

Identification of overlapping Janus droplets. From the pre-processed images with 10× magnification (greyscale images with adjusted brightness and contrast), the image processing program first estimated the range of diameters of the Janus droplets by using the calibrated marking underneath the analysis chamber. The program then sought out and mapped the centers and calculated the diameters of every Janus droplet. This process was done by a modified method based on the Circle Hough Transform. With the coordinates of the centers and the diameters of the Janus droplets, the program then evaluated overlapping droplets. Specifically, if the distance between two centers of two droplets was smaller than the sum of the two radii, the droplets were considered overlapping. Using this logic, the program could effectively map out the number of overlapping neighbors for every identified droplet.

Identification of droplet complexes. A Janus droplet was considered to be a part of a droplet complex if the number of its overlapping neighbor exceeded three. This threshold was set in some cases to prevent over-counting of the droplets at the edges of the droplet complexes and accidental overlapping of droplets. This measurement was further collaborated by the analysis based on the optical intensity. The area occupied by the agglutinated droplet complexes was then calculated.

Analysis of changes in optical intensity. Using the preprocessed images of 4× magnification (greyscale images with adjusted brightness and contrast), the program first applied the adaptive thresholding algorithm to distinguish the darker edges of the Janus droplets from the droplet complexes with tilted particles. More specifically, the program ignored the edges of the droplets that have inherent low-light intensity and only sought the area of droplet complexes. A threshold was set using areas with light intensity of less than 45% of the brightest regions to be considered part of the droplets complex. From this information, the area occupied by the droplet complexes was then calculated.

Example 6

The following example generally relates to bioconjugation of droplets, according to some embodiments.

Emulsion Assays and Surfactants Design Dynamic complex emulsions

Complex Emulsions were Fabricated at Temperatures Above the Upper Critical solution temperature of the internal phases to create materials with precisely determined compositions. Specifically, droplets containing equal volume of hydrocarbon (diethylbenzene) and fluorocarbon (HFE7500) liquid were emulsified around 40° C., which is above Tc (37° C.) in an aqueous continuous phase containing Zonyl FS-300 (hereafter 'Zonyl'), which is a nonionic fluorosurfactant. Surfactants generally lower the interfacial tension between two immiscible liquids and stabilize emulsion droplets. Droplets containing both hydrocarbon and fluorocarbon may switch morphologies between H/F/W (hydrocarbon-in-fluorocarbon-in-water), Janus, and F/H/W (fluorocarbon-in-hydrocarbon-in-water), with changes in the relative strength of the fluorocarbon and hydrocarbon surfactants.

Surfactant Design

Figure 14:
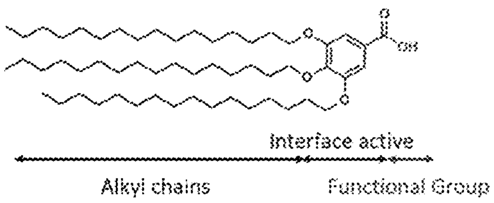
FIG. 14 shows the structure of exemplary tridodecyl gallic acid (GA120H) surfactant, according to one set of embodiments.

Creating surfactant molecules that interact with analytes is the helpful to create couplings to droplet morphology and orientation. The orientation in the absence of perturbation may be controlled by the density differences of the internal phases and gravity. The droplets are dynamic lenses and both morphology and orientation produce large optical signals. Optical transduction in these cases makes use of the light transparency because vertically aligned Janus droplets with internal phases having specific refractive indices. A transparency to highly scattering state may be triggered by small distortions in droplet morphology or agglutinated (tilting). To extend these methods, a generic surfactant platform was produced, shown in FIG. 14, for droplet bioconjugation with proteins, nucleic acids, and carbohydrates. The three alkyl chains in the tridodecyl gallic acid shown (GA12OH) provide for a robust hydrophobic anchor and the carbonyl based functional site provides for bioconjugation. The gallic structure was observed to be an intrinsic surfactant molecule that provides sufficient stability to prevent speciation of the generic reactive droplets. This design builds on the observation that aromatic rings with peripheral alkane chains organize at the oil-water interfaces to enhance the effectiveness at lowering interfacial tensions.

To validate the interfacial behavior of the gallic derived surfactant, emulsions with and without GA12OH in the hydrocarbon oil phase were produced in the same continuous phase (0.01 wt % Zonyl in PBS buffer). The pristine emulsion droplets without GA12OH, are in double emulsion morphology (FIG. 3E), namely hydrocarbon-in-fluorocarbon-in-water, whereas the emulsion droplets with 10 mg/mL GA12OH dissolved in the hydrocarbon phase appear in Janus configuration (FIG. 3E, 100B). These results confirm that GA12OH is a good surfactant that lowers the surface tension at the oil/water interface. Aside from helping with the control droplet formation, this feature indicates that the carboxylic acid groups are presented at the aqueous interface for chemical modification.

Emulsion Assays for Bioconjugation

Interfacial Functionalization on Emulsion Droplets

Figure 15A:
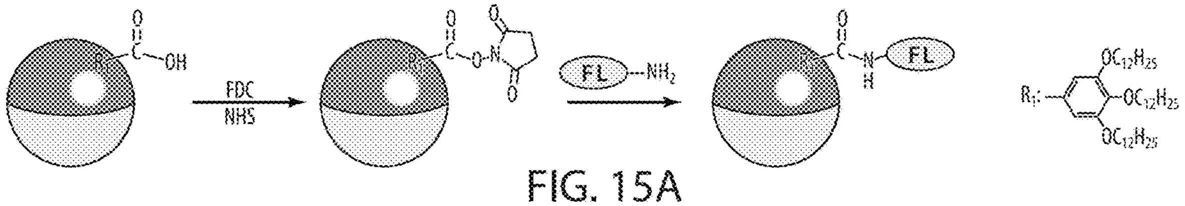
FIGS. 15A-15C show interfacial functionalization on a Janus droplet, according to one set of embodiments.

After confirming the surfactant behavior of GA12OH, the chemical reactivity at the droplet interface was studied using the EDC/NHS coupling reaction. As shown in FIG. 15A, GA12OH was loaded into the droplet phase and the droplets adopted a Janus morphology. EDC and NHS solutions were then added in the continuous phase. Fluoresceinamine was used as a model reactant for biomolecules bearing amine groups, and upon addition to the water phase reacts with the in situ generated NHS ester. The unreacted fluoresceinamine in the continuous water phase is removed by washing the droplets and a bright green fluorescence was observed at the hydrocarbon-water interface with confocal microscopy. The localized green fluorescence is attributed to the fluoresceinamine-NHS reaction to form a covalent amide bond at the droplet interface. Another dye, Sulfo-Cyanine 3 amine is separately functionalized to the droplet surface using the same method described above. When two batches of droplets functionalized with different dyes were combined together, no sign of mixing dyes was observed under microscopy even after extended period of time. This further confirmed the covalent bond formation at the hydrocarbon-water interface and that we can produce droplets that do not fuse or transfer functional groups between them. This latter feature is particularly useful for multiplexed detection schemes.

GA12-NHS Assay for Amine Conjugation

Figure 15B:
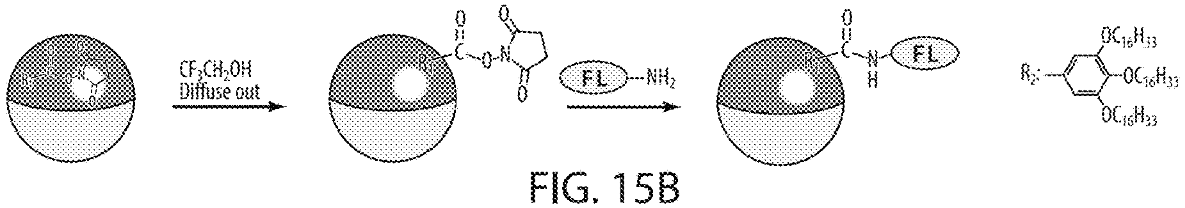
Figure 15C:
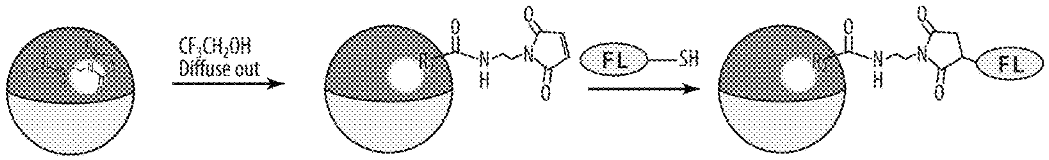

To investigate the scope of interfacial functionalization, surfactant GA12-NHS was pre-synthesized and dissolved in the droplet hydrocarbon phase (FIG. 15B). Trifluoroethanol was added the hydrocarbon and fluorocarbon droplet phase to lower the upper critical mixing temperature. After droplets are formed in the water phase, trifluoroethanol partitions into the continuous phase and internal phases then undergo phase separation to produce double emulsions. It was believed that the GA12-NHS has some portioning to hydrocarbon-water interface as a result of its surfactant behavior. The continuous phase was exchanged twice to remove the trifluoroethanol. This is facilitated because the droplets are denser than water and remain on the bottom of flask. The continuous phase solvent exchange does not affect the stability nor the morphology of the droplets. It was observed that fluoresceineamine functionalization with pre-synthesized GA12-NHS has a higher yield and resulted in 50% more intense fluorescence under confocal microscopy with relative to an internal dye reference (described later in this example). As a result, GA12-OH and in situ NHS formation is not quantitative.

GA16-MA Assay for Thiol Conjugation

Figures 16A, 16B:
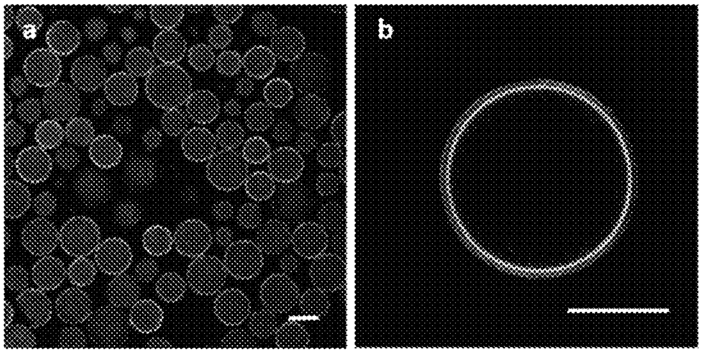
FIGS. 16A-16B show confocal microscopy images of cysteine-BODIPY functionalized droplets using interfacial maleimide-thiol chemistry. Scale bar in 50 μm.

To implement a maleimide-thiol bioconjugation scheme, GA16-MA (FIG. 15C) was pre-synthesized and loaded into the droplets. The longer hexadecyl chains increased the surfactant GA16-MA solubility in hydrocarbon phase. BODIPY-FL-Cysteine was used as the reactive model compound for biomolecules bearing thiol groups. Upon addition (FIG. 15C), this dye was covalently linked to the surface of the droplets and bright fluorescence from the BODIPY dye was observed at the hydrocarbon-water interface as shown in FIG. 16A-16B. In the control experiments under the same conditions without GA16-MA in the droplet phase, no fluorescent ring was observed by confocal microscopy.

Controlled Conjugation Reactivity of the Emulsion Assays

These complex emulsion assays generally use the interfacial functionalization and the recognition characteristics thereof. The droplet interface is dynamic and the morphology switches between H/F/W, Janus, and F/H/W with changes in the interfacial tensions between hydrocarbon-water interface and fluorocarbon-water interface. Another advantage of the emulsion droplets is that they can provide hydrolytic stability for the reactants that are localized in an internal phase that initially doesn't share an interface with water. With controlled activation the reactant can be used for functionalization later times.

Figure 17:
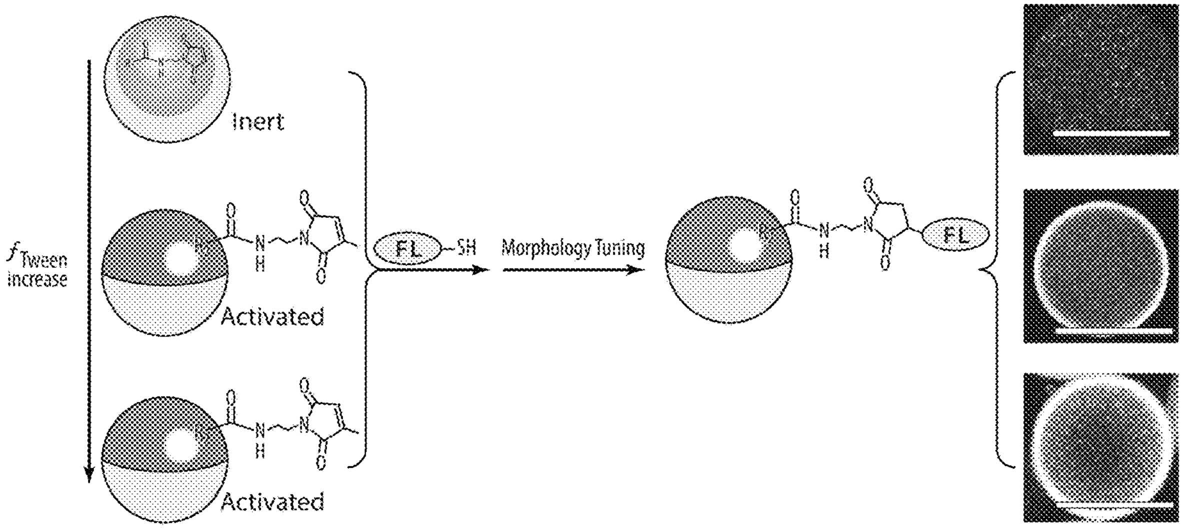
FIG. 17 shows dynamic emulsion droplets with controlled reactivity, according to one set of embodiments. Droplets start in different morphology and functionalized at the hydrocarbon-water interface. Droplets were then tuned to the Janus morphology for imaging. Higher intensity indicates higher level of functionalization at the interface.

As shown in FIG. 17, GA16-MA and BODIPY-FL-Cysteine was used to demonstrate the controlled interfacial conjugation. Tween 20 was chosen as the continuous phase "activating" hydrocarbon surfactant. Together with Zonyl as the continuous phase fluorocarbon surfactant, it is possible to tune the morphology of the droplets to facilitate maleimide-thiol conjugation. Tween 20 was chosen because of its mild surfactant behavior, which means it will not completely cover the hydrocarbon-water interface but is still able to change the morphology of the droplets. In the H/F/W morphology state, wherein the hydrocarbon oil was encapsulated inside the fluorocarbon phase, GA16-MA is rendered inert. When the droplet morphology was switched to Janus or F/H/W by the addition of Tween 20, the hydrocarbon phase now has a reactive interface with water and the interfaces are activated for functionalization reactions.

Quantification of the Interfacial Conjugation Reaction

Figure 18:
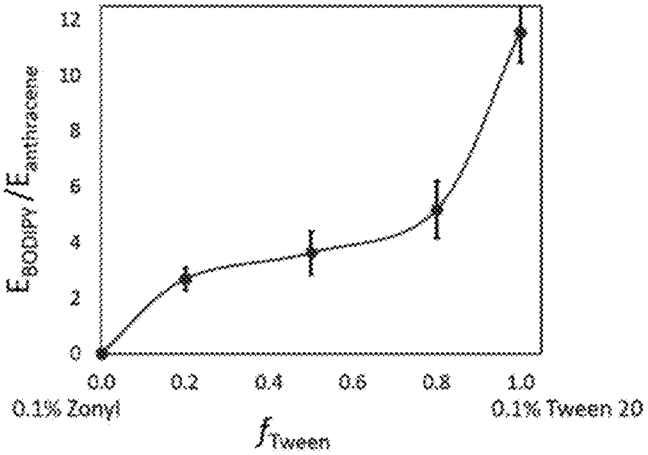
FIG. 18 shows the ratio of emission intensity at the interface ($E_{BODIPY}$) and inside ($E_{anthracene}$) relative to the continuous tween 20 surfactant concentration, according to one set of embodiments.

To further quantify the level of covalent functionalization at the interface, anthracene with different emission wavelength from BODIPY was used as an internal fluorescent reference to indicate the amount of fluorophore functionalized at the droplet interface. As shown in FIG. 17, the droplets with different starting morphology were functionalized with BODIPY using maleimide-thiol chemistry. After the reaction, the morphology of the droplets was tuned to the exact Janus state for confocal imaging by changing the continuous phase surfactant with either Zonyl or Tween 20. The fluorescent intensity of both fluorophores are analyzed through the open access software ImageJ (National Institute of Health, Bethesda, MD, USA) and the relative intensity ratio between $E_{anthracene}$ and $E_{BODIPY}$ was plotted against the initial droplet morphology, indicated by relative surfactant ratio $f_{Tween}$ (FIG. 18). The more surface area at the hydrocarbon-water interface during conjugation, the more thiol functionalization is to the droplets as indicated by the BODIPY fluorescent intensity.

Biomolecule Functionalized Emulsion Assays

Protein A Functionalized Assay for IgG Detection

Figure 19:
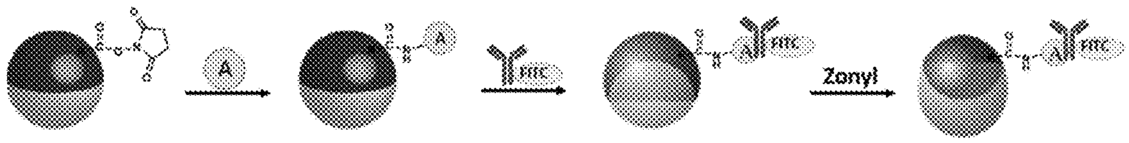
FIG. 19 shows exemplary droplet functionalization with protein A and detection scheme with immunoglobulin (IgG), according to one set of embodiments.
Figure 20A:
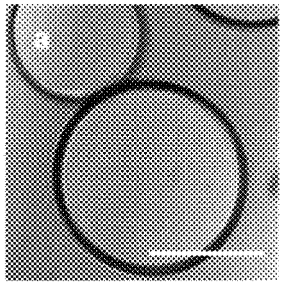
FIGS. 20A-20C show Protein A functionalized emulsion droplet for the detection of anti-mouse IgG, according to one set of embodiments. Scale bar in 50 μm.
Figure 20B:
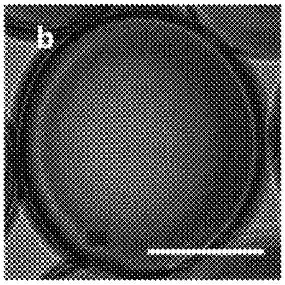
Figure 20C:
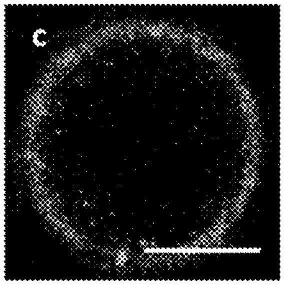

The examples above show that the emulsion droplets containing gallic acid (GA) based reactive surfactants can be functionalized with molecules bearing free amine or thiol group. Functionalization with biomolecules is useful to achieve broad utility in biosensing assays. As a prove-of-concept, a Protein A functionalized emulsion assay was targeted for the binding of anti-mouse IgG. As shown in FIG. 19, Protein A reacts through lysine amines with Janus emulsion droplets containing GA12-NHS. After functionalization, the emulsion droplets maintained a Janus morphology (FIG. 20A). Addition of FITC (fluorescein isothiocyanate) labelled anti-mouse IgG to the continuous phase results in binding to Protein A on the surface of droplets. This modification resulted in a change in droplet morphology from Janus to a F/H/W double emulsion (FIG. 20B). It was rationalized that the large IgG molecule provides additional hydrophilic character, which increases the surfactant strength at the hydrocarbon-water interface, thereby expanding the organic water interface. This morphology change from Janus (transparent) to F/H/W (opaque) is easily visualized with the transmission of natural light through thin gravity aligned layers of emulsion droplets. The binding of IgG to the droplet surface was further validated with confocal microscopy. The bright green fluorescence from the FITC labeled IgG was observed under confocal microscopy and was only located at the hydrocarbon-water interface (FIG. 20C). The GA12-NHS is therefore established as an active biomolecular reactive group for functionalization of the hydrocarbon-water interface.

Figures 21A, 21B:
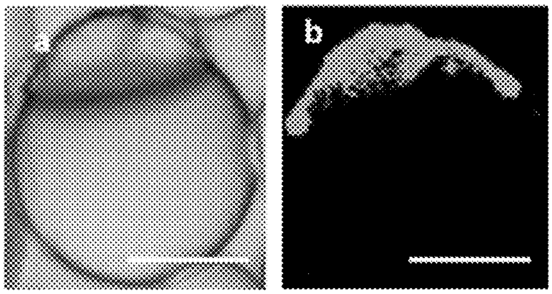
FIGS. 21A-21B show images of Zonyl forced droplets after IgG binding to protein A, according to one set of embodiments. Scale bar in 50 μm.

To demonstrate there is covalent bond between the droplet and Protein A/IgG complex, additional Zonyl surfactant was added in the continuous phase to force a morphology change from F/H/W to H/F/W. The Protein A/IgG complex is not dislodged from the hydrocarbon-water interface and the added Zonyl produces a deformation (FIG. 21) from a perfect sphere. If the droplet was not functionalized with proteins, the hydrocarbon phase would become an inner phase of a double emulsion, H/F/W. This experiment also shows that the interface was still dynamic after functionalization of either Protein A or IgG. Preserving a dynamic interface is central to sensing opportunities and producing changes in droplet morphology.

Nucleic Acid and Carbohydrate Functionalization

Figure 22A:
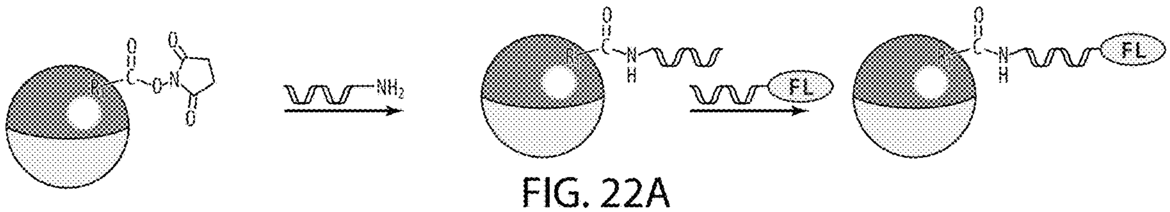
FIG. 22A shows bioconjugation with oligonucleotide followed by hybridization, according to one set of embodiments
Figure 22B:
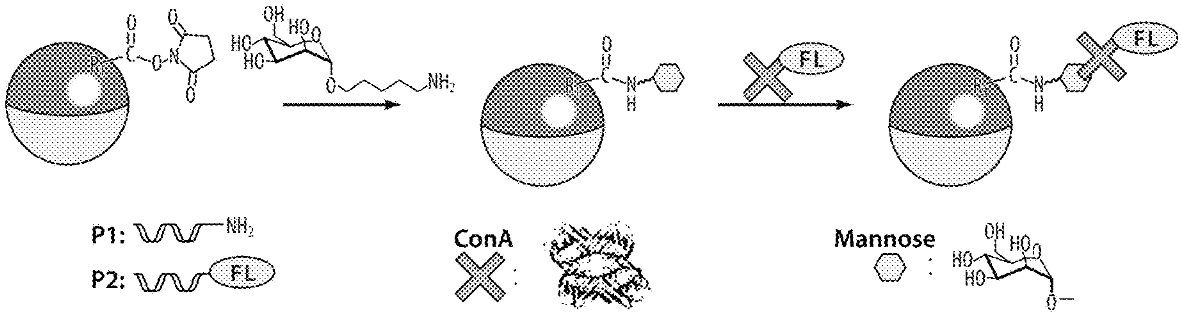
FIG. 22B shows bioconjugation with mannose derivative for the binding of concanavalin A, according to one set of embodiments.

To demonstrate the generic bioconjugation capabilities of the emulsion assay, broader types of biomolecules were functionalized to the droplets (FIGS. 22A-22B). A strand of oligonucleotide 5'-amine C6 linker modified P1 was covalently functionalized to the droplet surface with GA12-NHS and amine reaction. A complementary strand P2 bearing a (6-carboxyfluorescein) 6-FAM tag at the 5' was added in the continuous phase. After removing unreacted oligonucleotide by washing, fluorescence from FAM was observed under confocal microscopy at the hydrocarbon-water interface, which indicates the oligonucleotide still maintains the reactivity. A mannose bearing amine was functionalized to the droplets using NHS-amine chemistry. Concanavalin A (ConA) labelled with FITC was added in the continuous phase. After washing the excess ConA from the mixture, fluorescence from FITC was observed under confocal microscopy, showing the carbohydrate-lectin binding interactions were preserved.

Conclusion

An emulsion assay capable of bioconjugation using NHS-amine or maleimide-thiol chemistry was designed. This assay has provided a generic platform for functionalization of biomolecules to the emulsion droplets as biosensors for the detection of antibodies, enzymes, nucleic acids and carbohydrates. The dynamic interface and droplet morphologies enable the controlled interfacial reactivity. The reactions modify the morphological changes that are easily detected with natural light transmission. Quantitative optical method and sensing of other targeted biomolecule will be demonstrated in follow-up studies.

Experimental Section

General Methods and Instrumentation

Diethylbenzene (DEB), 2-(trifluoromethyl)-3-ethoxydodecafluorohexane (HFE7500), hydroxylamine, trifluoroethanol, phosphate-buffered saline (PBS, pH=7.6) (1M), Tris buffer (pH=8.0), HEPES buffer (pH=7.6), Zonyl FS-300, fluoresceinamine, tris(2-carboxyethyl)phosphine hydrochloride (TCEP), N-(3-Dimethylaminopropyl)-N'-ethylcarbodiimide hydrochloride (EDC), N-hydroxysuccinimide (NHS), Concanavalin A-FITC, anti-mouse IgG-FITC and Protein A were purchased from Sigma-Aldrich. BODIPY FL L-Cystine was purchased from ThermoFisher. Sulfo-Cyanine3 amine was purchased from Lumiprobe. Solvents were purchased from Sigma-Aldrich and used as received. Oligonucleotides were purchased from Integrated DNA Technologies (IDT) and used without further purification.

EDC and NHS were dissolved in PBS at 1M and prepared fresh before each usage. Continuous phase surfactants were prepared as stock solution in PBS, including 0.1 wt % and 0.01 wt % Zonyl FS-300 as the fluorocarbon surfactant and 0.1 wt % Tween 20 as the hydrocarbon surfactant. Hydroxylamine was prepared as 1M solution in PBS to quench unreacted NHS groups at the droplet interface.

NMR spectra were recorded using a Bruker Avance 400 MHz NMR spectrometer and were referenced to the proton resonances resulting from incomplete deuteration of NMR solvent (1H). Confocal microscopy images were taken at room temperature with Nikon AiR Ultra-Fast Spectral Scanning Confocal Microscope.

Emulsion Assay Preparation

Bulk emulsification for polydispersed complex emulsion droplets Complex emulsions, composed of equal volumes of diethylbenzene and HFE7500 in aqueous continuous phase were fabricated using bulk emulsification, which generates polydisperse droplets (20-100 m in diameter). In this process, the hydrocarbon phase (DEB) and fluorocarbon phase (HFE7500) were mixed and heated above the upper critical temperature (around 40° C.) to generate a single droplet phase. This single droplet phase was then dispersed into the aqueous phase containing the continuous phase surfactants to generate single phase emulsions and upon cooling to room temperature, the DEB and HFE7500 phases separated to generate complex emulsions. The composition of all droplets was identical because every droplet originated from the same single phase.[11] A generic assay contains 0.5 mL of continuous phase and 20 μL droplet phase.

GA12OH assay preparation

To generate emulsion droplets containing GA120H for interfacial functionalization, GA12OH was dissolved with gentle heat at 10 mg/mL in DEB. Polydispersed complex emulsion droplets were fabricated via bulk emulsification described above with 0.01 wt % Zonyl as the continuous phase surfactant. 25 μL of EDC solution was added to the emulsion and reacted for 15 min followed by addition of 25 μL of NHS solution. The reaction was set at room temperature for 1 h on a rocker (Rocker II from Boekel Scientific). The resulting assay is in equivalent to a GA12-NHS assay.

GA12-NHS assay preparation and fluoresceinamine functionalization

GA12-NHS was dissolved at 10 mg/mL in DEB. Trifluoroethanol was added at 10% in volume to the hydrocarbon and fluorocarbon mixture to decrease the mixing temperature. A mixture of 0.1 wt % Zonyl:0.1 wt % Tween 1:1 (v/v) was used as the continuous phase to increase the hydrocarbon-water surface area for bioconjugation. After emulsification, the continuous phase was exchanged twice with the same mixture of 0.1 wt % Zonyl:0.1 wt % Tween 1:1 (v/v) to remove the trifluoroethanol from the emulsion assay. Fluoresceinamine was prepared as 0.5 mg/mL solution in PBS. 25 μL of the fluoresceinamine solution was added to the GA12-NHS assay and reacted at room temperature overnight on a rocker. The continuous phase was washed 5 times after reaction to remove the excess amount of dye before imaging.

Sulfo-Cyanine 3 amine was prepared as 1 mg/mLl solution in PBS. 25 μL of the Sulfo-Cyanine 3 amine solution was added to the GA12-NHS assay. The reaction was carried out overnight at room temperature. Two vials containing different dye functionalized droplets were combined together. The mixture was settled for 48 h before imaging.

GA16-MA Assay Preparation and BODIPY-FL-Cysteine Functionalization

GA16-MA was dissolved at 10 mg/mL in DEB and the assay was prepared using the same method as described for the GA12-NHS assay.

BODIPY-FL-Cysteine was first dissolved in PBS at 1 mg/mL and activated with TCEP. The activated dye solution become bright green within 15 min and 25 μL of the activated dye solution was added to the GA16-MA assay. The continuous phase was washed 5 times after overnight reaction to remove excess amount of dye before imaging.

Protein a Functionalization and IgG Detection

Protein A was dissolved at 0.5 mg/mL in PBS buffer. 25 μL of the Protein A solution was added to a GA12-NHS assay and reacted overnight at room temperature on a rocker. The reaction was stopped with 25 μL of hydroxylamine solution to quench any unreacted NHS groups at the droplet surface. The continuous phase was washed with surfactant solution for three times. 25 μL anti-mouse IgG with FITC label from Sigma-Aldrich was added to the Protein A functionalized assay and reacted for 2 h. The continuous phase was then washed with surfactant solution for five times to remove unreacted IgG before imaging.

Oligonucleotide Functionalization GA12-NHS assay was prepared as described in the previous section. 3 μL of oligonucleotide P1 with a sequence of 5'-$NH_2$-$(CH_2)_6$-TTT TTT TTT T AGA GTT GAG CAT-3' at 2 mM in PBS solution was added in the continuous phase. The conjugation reaction was carried out overnight at room temperature. The reaction was quenched with addition of 100 μL of 1M Tris buffer solution. 3 μL of complementary strand of oligonucleotide P2 with a sequence of FAM-5'-TTT TTT TTT T ATG CTC AAC TCT-3' at 1 mM in PBS solution was added. The solution was heated up to 50° C. and held for 15 min using a water bath. The emulsion assay was then allowed to cool down to room temperature and the continuous phase was washed 5 times to remove the unreacted oligonucleotide.

Carbohydrate Functionalization

GA12-NHS assay was prepared as described in the previous section. Man-C5-$NH_2$ was dissolved in PBS at 1 mg/ml. 50 μL of Man-5-$NH_2$ solution was added in the continuous phase and reacted overnight at room temperature. The reaction was quenched with 100 μL of 1M Tris buffer solution. 10 L of 1 mg/mL FITC labelled Con A in HEPES buffer was added and reacted for 30 min. The solution was then washed 5 times to remove the excess lectin before imaging.

1. Synthetic Procedures 1.1. Synthesis of GA12OH

Figure 23A:
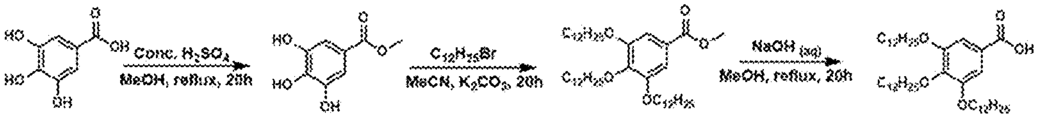
FIG. 23A shows a synthetic procedure for GA12OH, according to one set of embodiments.

GA12OH was synthesized as shown in FIG. 23A.

Figure 23B:
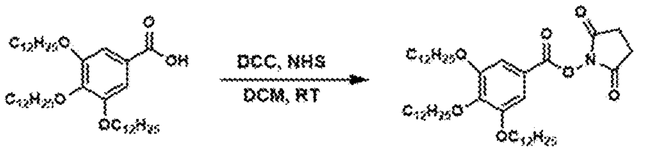
FIG. 23B shows a synthetic procedure for GA12-NHS, according to one set of embodiments.

1.2. Synthesis of GA12-NHS GA12-NHS was synthesized as shown in FIG. 23B. GA12OH (1 g, 1.3 mmol), N,N'-dicyclohexylcarbodiimide (0.347 g, 1.7 mmol) and N-hydroxysuccinimide (0.194 g, 1.7 mmol) were dissolved in 50 mL dichloromethane followed by addition of catalytic amount of DMF. The solution was stirred at room temperature overnight. The crude material was purified by silica gel column chromatography using hexane and EtOAc (4/1).

$^1$H NMR (400 MHz, CDCl3): δ 7.32 (s, 2H), 4.07-3.99 (m, 6H), 2.92-2.89 (m, 4H), 1.85-1.78 (m, 4H), 1.75-1.70 (m, 2H), 1.50-1.43 (m, 6H), 1.36-1.26 (m, 48H), 0.89-0.86 (m, 9H)

1.3 Synthesis of GA16-MA

Figure 23C:
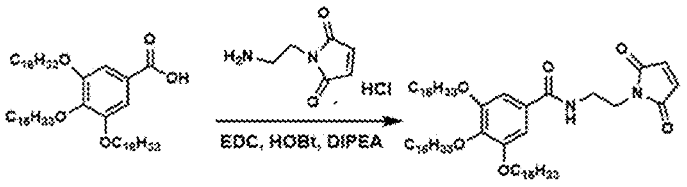
FIG. 23C shows a synthetic procedure for GA16-MA, according to one set of embodiment.

GA16OH was used for the synthesis of GA16-MA to increase the solubility in hydrocarbon (see FIG. 23C). To a solution of GA16OH (0.5 g, 0.60 mmol) in dichloromethane (10 mL) was added N,N-diisopropylethylamine (0.85 ml, 6 mmol). The mixture was treated with N-(3-dimethylaminopropyl)-N'-ethylcarbodiimide hydrochloride (0.19 g, 1 mmol), 1-hydroxybenzotriazole (0.13 g, 1 mmol) and N-(2-aminoethyl)maleimide hydrochloride (0.116 g, 0.66 mmol) and stirred at room temperature overnight. The reaction was quenched with droplet of HCl (1M) solution and washed with water for three times. The organic portion was dried over $Na_2SO_4$. The crude material was purified by silica gel column chromatography using hexane and EtOAc (4/1 to 3/1).

Example 7

The following example describes the preparation of LC double emulsions, according to some embodiments.

Figure 25A:
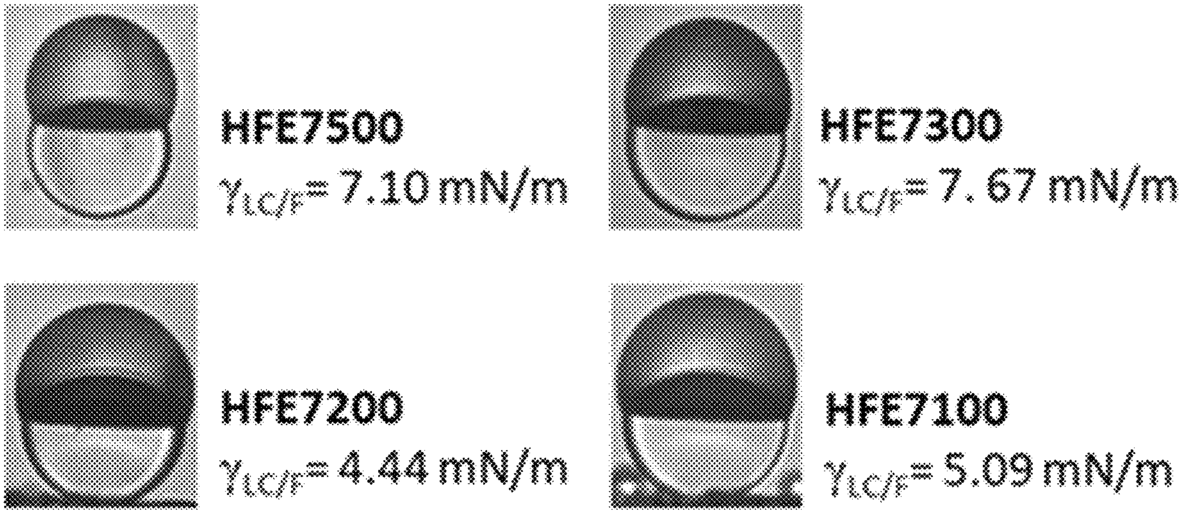
FIG. 25A. schematically depicts a side-view microscope images and γLC/F interfacial tension varying the fluorocarbon phase of a "snowman-shaped" Janus droplets, according to one set of embodiments.
Figure 25B:
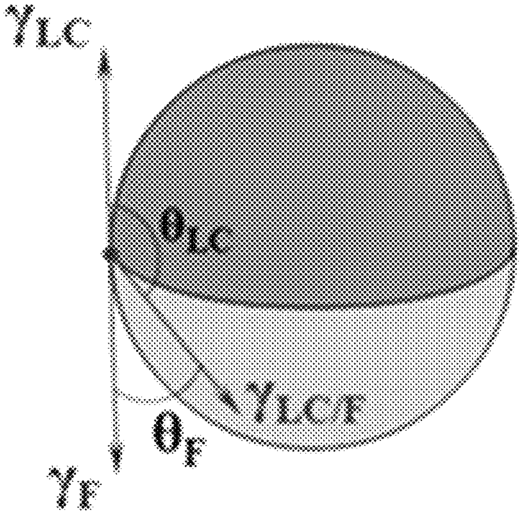
FIG. 25B is a schematic representation of interfacial tensions of a Janus droplet, according to some embodiments.
Figure 25C:
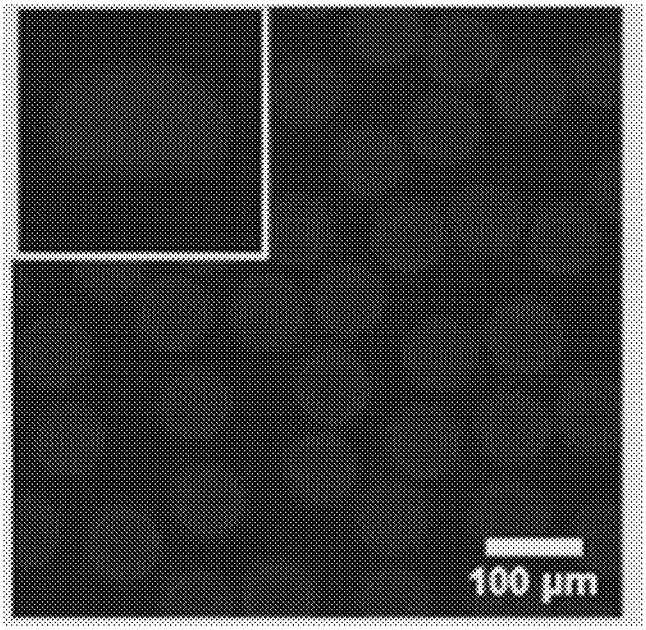
FIG. 25C shows confocal microscopy images (inset: side-view 3D visualization of the LC compartment), according to some embodiments.

To produce dynamic multicompartment emulsions containing LCs, the nematic LC 4-cyano-4'-pentylbiphenyl (5CB) ($T_{N-I}$=35° C.) was chosen for the hydrocarbon phase and hydrofluoroethers (HFEs) as the fluorocarbon phase. The temperature-induced phase separation process to create droplets was limited to materials with easily accessible upper critical temperatures ($T_c$). Unfortunately, the $T_c$ of 5CB/HFE mixtures was outside of convenient temperature ranges. Therefore, an evaporation-induced phase separation method was utilized. Two immiscible fluids (5CB and HFEs) generated a homogenous mixture with the addition of dichloromethane (DCM). In a typical preparation, a 1:1:2 volume ratio of 5CB/HFEs/DCM was emulsified in an aqueous solution containing 0.1 wt. % of the nonionic surfactant Tween-20. After complete evaporation of DCM, "snowman-shaped" Janus droplets with two phase-separated compartments were formed (FIG. 25A). Without wishing to be bound by theory, the morphology of these complex liquid droplets was controlled by the relative interfacial tensions between LC-W ($\gamma_{LC}$), F-W ($\gamma_F$), and LC-F ($\gamma_{LC/F}$). These three interfacial tensions determined the equilibrium droplet configuration (FIG. 25B), which can be characterized by the contact angles between $\gamma_{LC}$ and $\gamma_{LC/F}$ ($\theta_{LC}$) and between $\gamma_F$ and $\gamma_{LC/F}$ ($\theta_F$) at the junction point (where the three phases came into contact). This balance of forces can be expressed by the following equations:

$$\cos(\theta_{LC}) = \frac{\gamma_F^2 - \gamma_H^2 - \gamma_{LC/F}^2}{2 \cdot \gamma_{LC/F} \cdot \gamma_F}$$

$$\cos(\theta_F) = \frac{\gamma_{LC}^2 - \gamma_F^2 - \gamma_{LC/F}^2}{2 \cdot \gamma_{LC/F} \cdot \gamma_F}$$

When $\gamma_{LC/F}$ is significantly smaller than $\gamma_{LC}$ and $\gamma_F$, droplets adopted spherical shapes and slight changes in the balance of interfacial tensions with the water induce dramatic changes in the droplet morphology. However, as $\gamma_{LC/F}$ increased, droplets sought to minimize LC-F interfacial area and become "snowman-shaped". This relationship was explored by comparing the morphology of double emulsions comprising 5CB and varying HFE oils and the corresponding $\gamma_{LC/F}$ seen in Table 1 below.

TABLE 1

Average interfacial tension (γ) values for 5CB dispersed in HFE solvents.

| FC phase | HFE-7300 | HFE-7500 | HFE-7100 | HFE-7200 |
|---|---|---|---|---|
| $\gamma_{LC/F}$ (mN/m) | 7.67 ± 0.03 | 7.10 ± 0.02 | 5.09 ± 0.02 | 4.44 ± 0.02 |

In agreement with above equations, as $\gamma_{LC/F}$ decreased gradually from 7.67 to 4.44 mN/m, Janus droplets exhibited an increased LC-F surface area (FIG. 25A). Afterwards, HFE7200 was used as fluorocarbon phase to achieve near-spherical morphology as a result of the lower $\gamma_{LC/F}$ with LC phases.

Figure 32A:
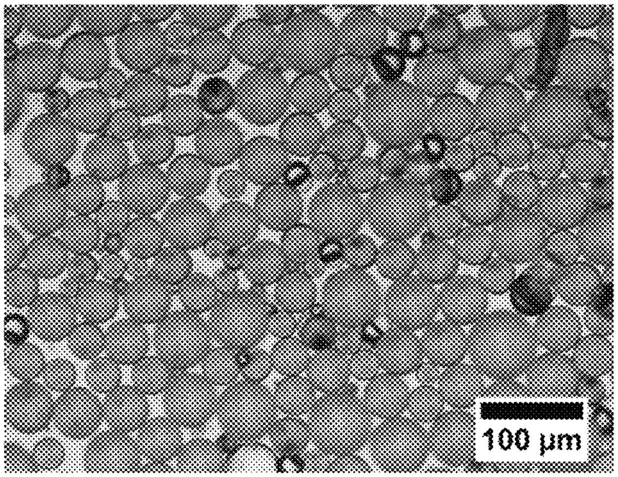
FIGS. 32A-32B show polarized-light optical microscopy images without (left) and with (right) crossed polarizers of LC complex droplets prepared by bulk emulsification, according to some embodiments.
Figure 32B:
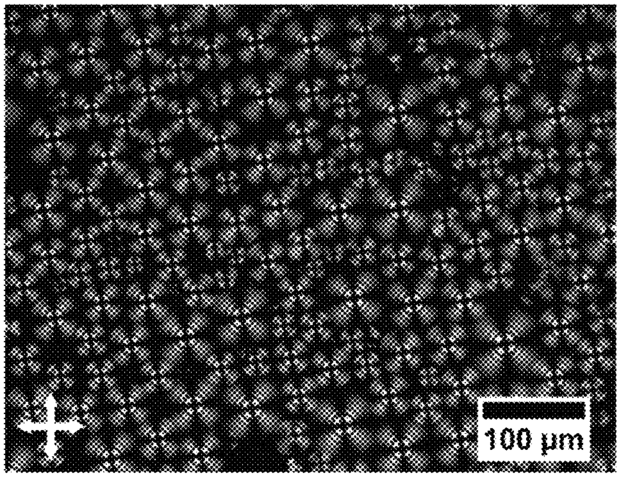

Bulk emulsification lead to polydispersed droplet sizes (FIG. 32), but it enabled rapid fabrication with standard laboratory equipment and provides droplets with highly uniform morphology and composition. The evaporation-driven phase separation route is also compatible with microfluidic routes to monodisperse complex LC colloids on a large scale (FIG. 25D).

Figure 25D:
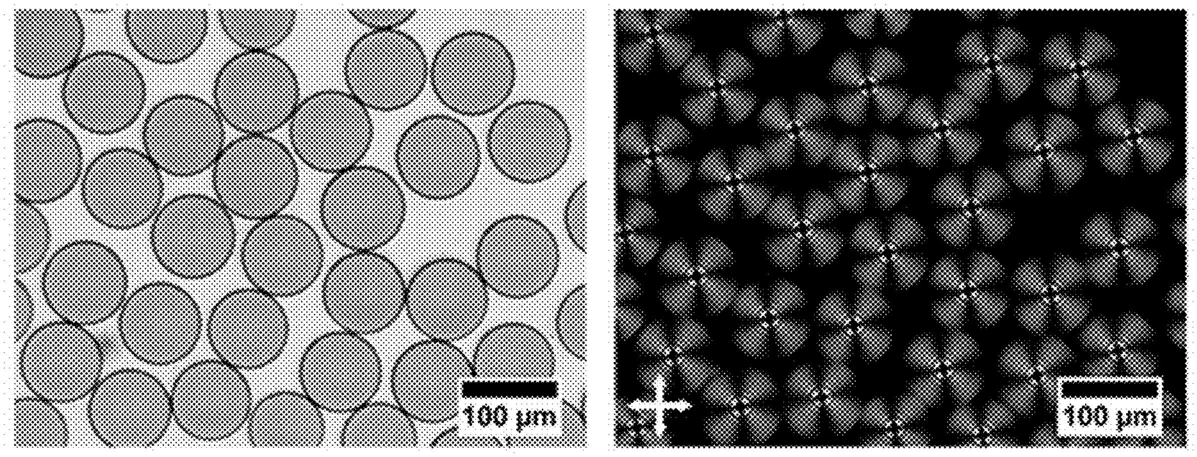
FIG. 25D shows polarized-light optical microscopy images without (left) and with (right) crossed polarizers, according to some embodiments.
Figure 25E:
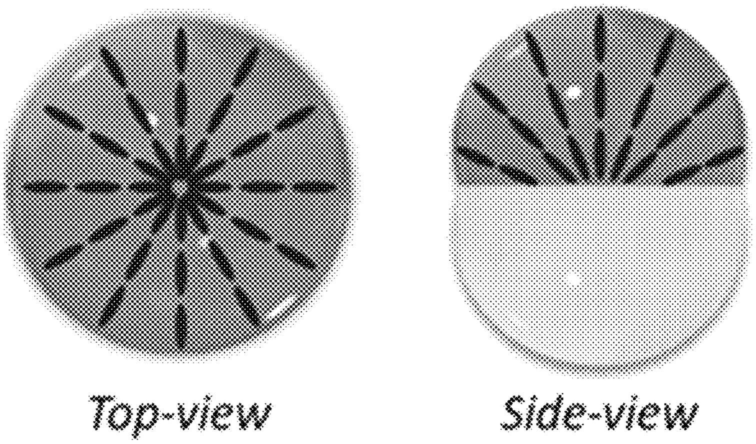
FIG. 25E is a schematic representation of radial alignment of an asymmetric (e.g. "snowman-shaped") Janus droplet, according to some embodiments.

Polarized-light optical microscopy (POM) of these colloids revealed that the optically isotropic fluorocarbon appeared dark, while birefringent LC appeared bright with an extinction point at the center of the droplets (Maltese cross texture) (FIG. 25D). These POM textures are indicative of a radial configuration in which the LC molecules anchor perpendicular to the aqueous phase (FIG. 25E). Using a confocal laser scanning microscope, further characterize of their morphology in 3D (FIG. 25D inset) was taken. Upon addition of perylene to the mixture, bright blue fluorescence was observed from the top hemisphere, indicating that this dye selectively partitions into the LC phase.

Example 8

The following example describes the stabilization of LC double emulsions via internal surfactant, according to some embodiments.

Figure 26A:
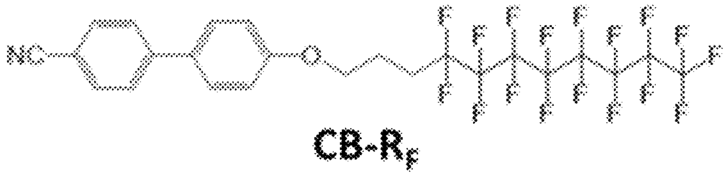
FIG. 26A shows the chemical structure of some LC/F internal surfactants, according to some embodiments.
Figure 26A:
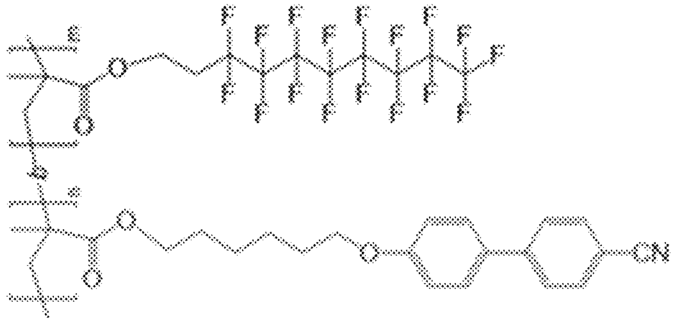

Although "snowman-shaped" Janus droplets were stable with balanced interfacial tensions, perfect spherical morphologies were not realized as a result of a significant $\gamma_{LC/F}$. Without wishing to be bound by theory, it was hypothesized that the $\gamma_{LC/F}$ can be reduced to produce perfect spheres by the addition of an appropriately designed internal surfactant. Accordingly, monomeric and polymeric surfactants were synthesized containing a LC and F components designed to organize at the internal interface (FIG. 26A).

Figure 26B:
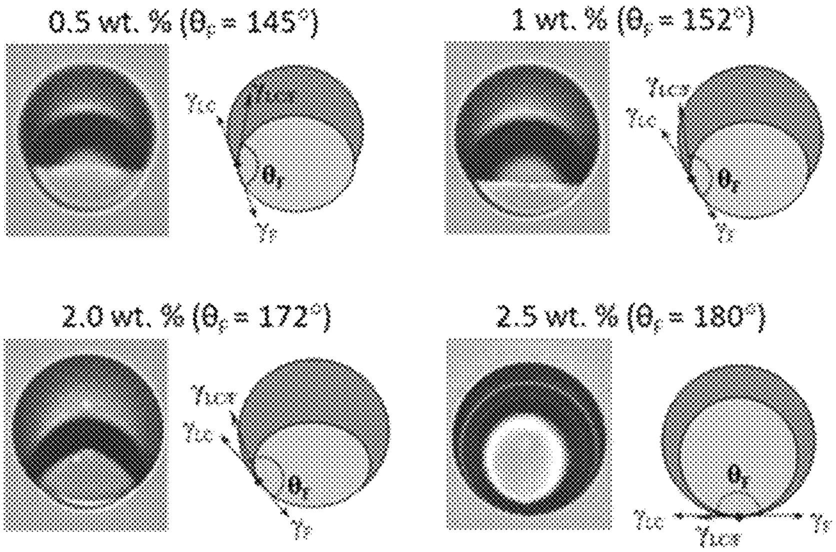
FIG. 26B shows side-view microscope images with varying CB-$R_F$ concentration and the corresponding sketch of the interfacial tensions (the bottom and top lines represent the direction of the three interfacial tensions while their lengths are arbitrary, where all droplets were pre-pared in a 0.1 wt. % aqueous solution of Tween-20, according to one set of embodiments.
Figure 26C:
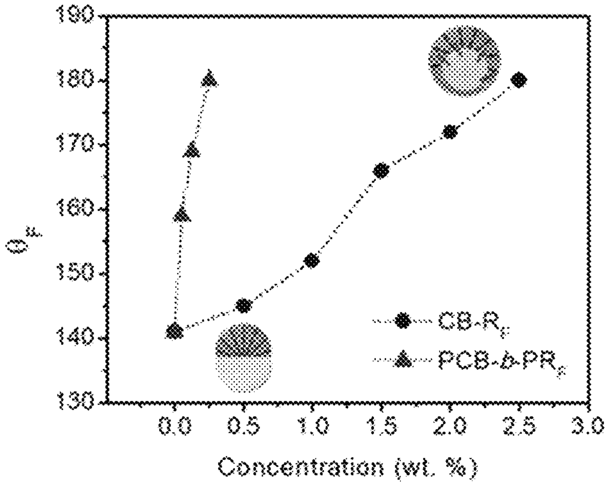
FIG. 26C is a plot of $O_F$ vs concentration of internal LC/W surfactant where the values reported for $O_F$ were the average of at least 5 independent measurements using a 0.1 wt. % aqueous solution of Tween-20 in an aqueous continuous phase, according to one set of embodiments.

All the internal surfactants were dissolved in the 5CB/HFE7200/DCM solution which was then emulsified in a 0.1 wt. % aqueous solution of Tween-20. After DCM evaporation, stable Janus droplets were obtained with CB-$R_F$ and PCB-b-$PR_F$ internal surfactants. FIG. 26B reveals that the interfacial area between the LC and F phases expands with increasing the CB-$R_F$ concentration, demonstrating a lowering of $\gamma_{LC/F}$. To better demonstrate this phenomenon quantitatively, numerical analysis was performed on the topology of the Janus droplets prepared in 0.1 wt. % Tween-20 in order to characterize how close a droplet is to a symmetrical Janus droplet. The equilibrium shape of droplets was fully determined by the contact angles between the interfaces which are used to calculate interfacial tensions. Since LC/F surfactant molecules exclusively concentrate at the internal interface, $\gamma_{LC}$ and $\gamma_F$ remain constant; changes in $\theta_F$ were controlled by $\gamma L_{C/F}$. Accordingly, $\theta_F$ was used to estimate the distortions from a perfect spherical Janus droplet and $\theta_F$ is 90° in the symmetrical (spherical) Janus state, 0° in a 5CB-in-HFE7200-in-water (LC/F/W) double emulsion, and 180° in a HFE7200-in-5CB-in-water (F/LC/W) double emulsion. An example of the analysis is shown in FIG. 26B wherein the junction point was first determined, and then angles between three tangential lines were drawn. $\theta_F$ increased with increasing concentration of CB-$R_F$ and PCB-b-PRF, as a result of their localization at the LC/F interface. At a concentration of 2.5 wt. % CB-$R_F$ or 0.25 wt. % PCB-b-PRF, emulsification in 0.1 wt. % Tween-20 generated droplets that adopt a spherical F/LC/W double emulsion configuration ($O_F$=180°), which is the expected morphology with sufficiently low $\gamma_{LC/F}$ and Tween-20.

Figure 26D:
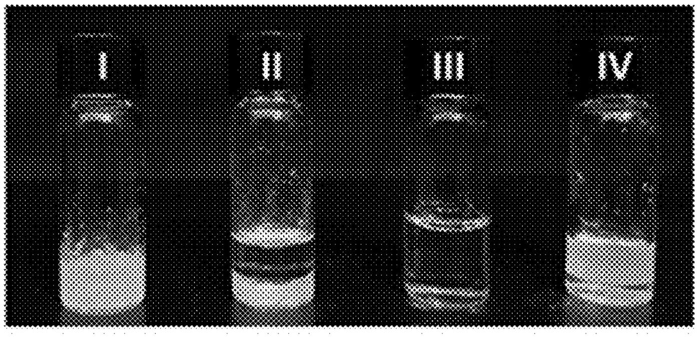
FIG. 26D shows CB-$R_F$ solubility in 5CB and HFE7200 where (I) is a mixture of CB-$R_F$ (2.5 wt. %) in 5CB, (II) is a mixture of CB-$R_F$ (2.5 wt. %) in 5CB after addition of HFE7200, (III) is a mixture of CB-$R_F$ (2.5 wt. %) in 5CB and HFE7200 using DCM (dichlormethane) as a cosolvent, and (IV) is a mixture of CB-$R_F$ (2.5 wt. %) in 5CB and HFE7200 after DCM evaporation, according to one set of embodiments.
Figure 26E:
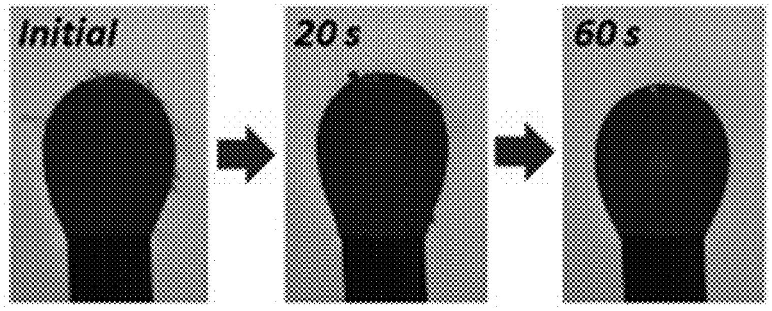
FIG. 26E contains snapshots showing the evolution of a droplet with dissolving and partitioning of surfactant, where the deformation at the interface in initial and 20 s images is due to surfactant particulates before partitioning and alignment at the LC-F interface, according to some embodiments.

The $\gamma_{LC/F}$ values can be determined at different concentrations of CB-$R_F$ and PCB-b-PRF independently by pendant drop analysis (Table 1 and FIG. 26E). To this end, LC solutions were prepared by mixing the corresponding LC/F surfactant, 5CB, and DCM. DCM was evaporated overnight, the resulting mixture was heated above the LC clearing point, and pendant drop measurements were made in HFE7200. The pendant drop measurements supported the $\theta_F$ calculations, where $\gamma_{LC/F}$ decreases from 4.0 to 3.2 mN/m with increasing concentration of PCB-b-PRF from 0.05 to 0.25 wt. %. Further, at higher concentrations of PCB-b-PRF the pendant drops become unstable overtime, which is related to a great decrease in $\gamma_{LC/F}$ below measurement capabilities.

Figure 33:
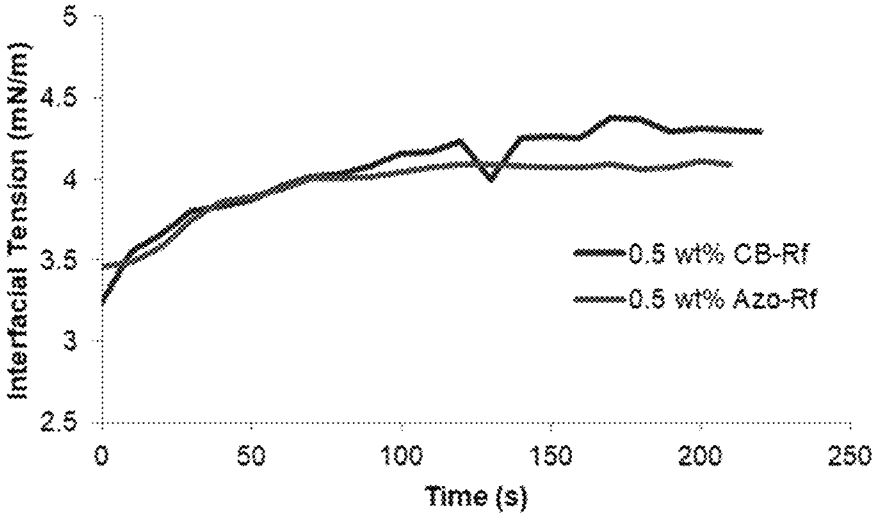
FIG. 33 is a plot of interfacial tension measurements of 5CB in HFE-7200, in the presence of 0.5 wt. % CB-$R_F$ and AZO-$R_F$ in 5CB, according to one set of embodiments.

At high wt. % of CB-$R_F$ (>1 wt %) a viscous heterogeneous mixture with 5CB was obtained (FIG. 26D, vial I), and after the addition of HFE7200, CB-$R_F$ was still not solubilized in this biphasic mixture (FIG. 26D, vial II). However, the addition of DCM generated a homogeneous solution (FIG. 26D, vial III) and after overnight evaporation of DCM a homogeneous biphasic mixture was generated (FIG. 25D, vial IV). These observations suggest that the LC/F surfactants are only partially soluble in both phases and localize at the LC/F interface after DCM evaporation. The partitioning of CB-$R_F$ is further demonstrated in pendant drop measurements, wherein deformation along the LC/F interface was observed (FIG. 26E). Initially, the CB-$R_F$ was in particulate form and the time profile in FIG. 26E showed that the particles dissolve at the interface with HFE7200 to produce an equilibrium $\gamma_{LC/F}$ (FIG. 26E). As a result of complexities in solubility of CB-$R_F$, the interfacial tension appears to display an unexpected increase until equilibrium reached (FIG. 33). With the addition of 0.5 wt. % of CB-$R_F$ a $\gamma L_{C/F}$ 4.28 mN/m was obtained. This decrease in $\gamma_{LC/F}$ is small relative to that produced by PCB-b-PRF at a 10 times lower concentration, thereby demonstrating the higher performance of the polymeric surfactant. All of the pendant droplet results were in good agreement with $\theta_F$ measured directly in the complex emulsions.

Figures 27A, 27B, 27C:
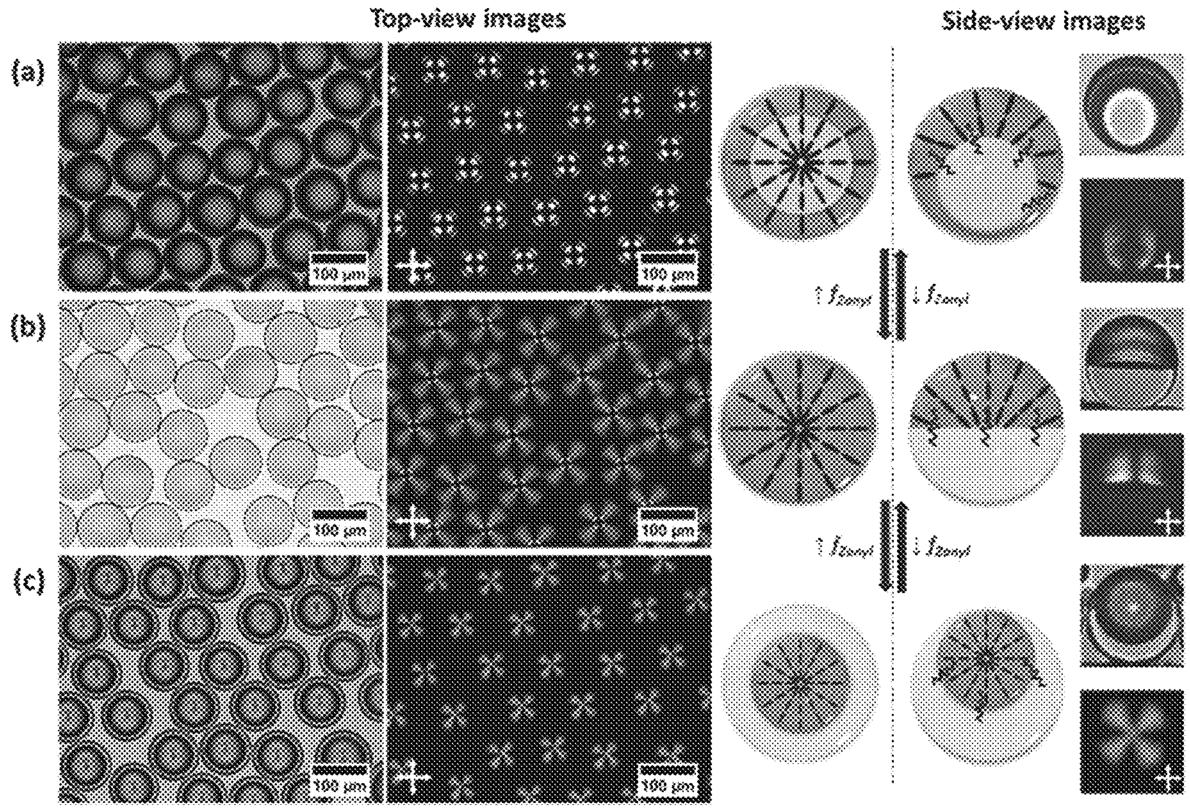
FIG. 27A-27C shows complex emulsions with a radial alignment of the LC molecules: polarized-light optical microscopy images without (left) and with (right) crossed polarizers of 5CB-HFE7200 droplets that reconfigure in response to variation in the mass ratio of hydro-carbon and fluorocarbon surfactants ($f_{Zonyl}$): (a) F/LC/W double emulsions ($f_{Zonyl}$=0-0.15), (b) spherical Janus droplets ($f_{Zonyl}$=0.20-0.35), and (c) LC/F/W double emulsions ($f_{Zonyl}$=0.4-1).

Having reduced the $\gamma_{LC}$/F, dynamic reconfiguration of the double emulsions was readily achieved in LC/F droplets through changes in hydrocarbon/fluorocarbon surfactant mass balance. Consequently, emulsification of a 1:1:2 volume ratio of 5CB/HFE7200/DCM with 2.5 wt. % CB-$R_F$ or 0.25 wt. % PCB-b-$PR_F$ in a 0.1 wt. % aqueous solution of Tween-20, generated a spherical F/LC/W double emulsion after complete evaporation of DCM (FIG. 27A). Gradual introduction of the nonionic fluorosurfactant Zonyl FS-300 (thereafter Zonyl), the droplet morphology dynamically changed passing through a spherical Janus morphology (FIG. 27B) before inverting to LC/F/W double emulsion (FIG. 27C). The droplets morphology changes were also observed by POM to elucidate the LC ordering throughout the geometry changes. The CB-$R_F$ and PCB-b-PRF internal surfactants do not impact the normal perpendicular anchoring of 5CB at the fluorous interface and both Janus and F/LC/W droplets exhibited radial configurations. In LC/F/W double emulsions the point defect at the center of spherical of the LC compartment confirms a uniform radial anchoring.

Figure 28A:
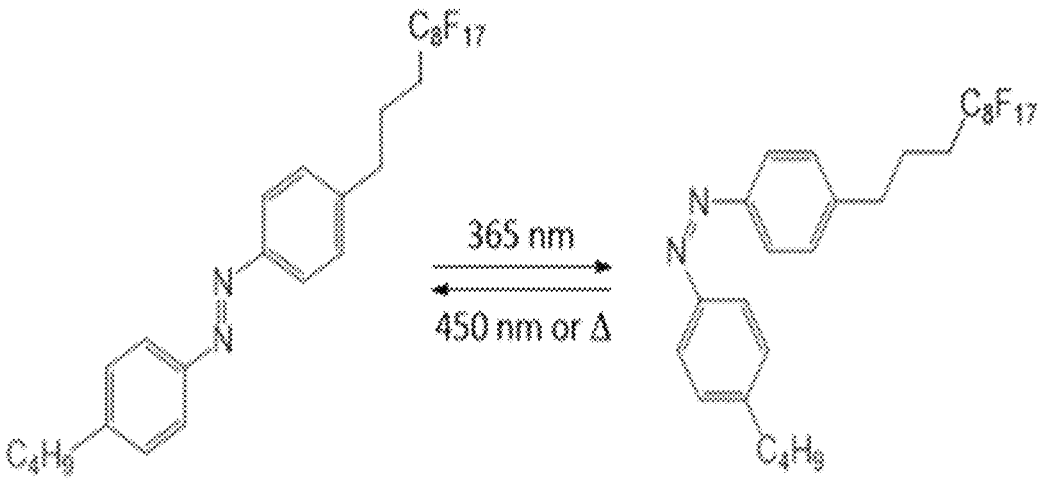
FIG. 28A shows the chemical structure of the light-responsive internal surfactant (AZO-$R_F$) which reversibly isomerizes under UV irradiation between the rod-like trans form of the surfactant and the bent-shaped cis form using light-responsive LC/F internal surfactant, according to some embodiments.
Figure 28B:
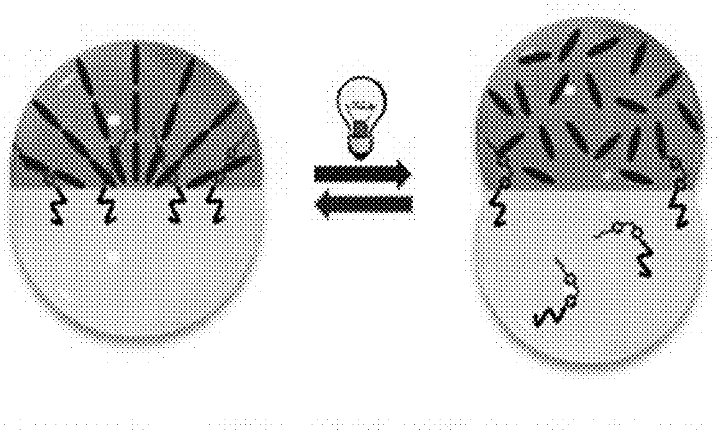
FIG. 28B is a schematic representation of Janus droplets containing AZO-$R_F$ in which UV light irradiation results in a disorder of the nematic LC phase using light-responsive LC/F internal surfactant, according to some embodiments.
Figure 28C:
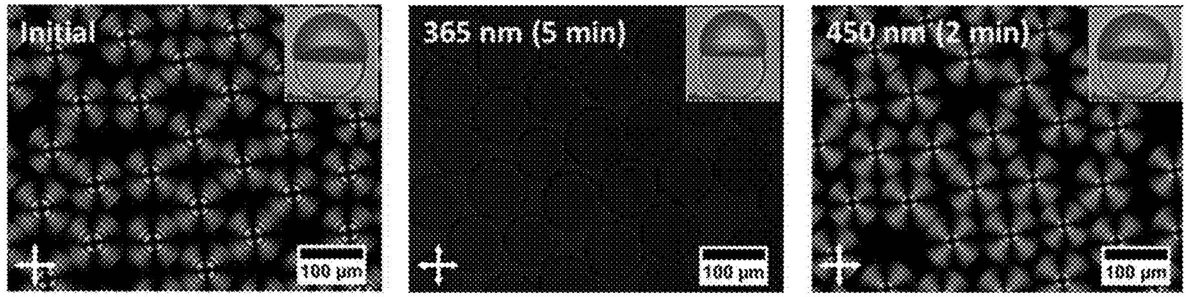
FIG. 28C shows polarized-light optical microscopy images of the photoinduced phase transition from nematic to isotropic upon irradiation at 365 nm, and subsequent phase transition from isotropic to nematic upon 450 nm irradiation with an inset showing corresponding side-view images using light-responsive LC/F internal surfactant, according to one set of embodiments.
Figure 29A:
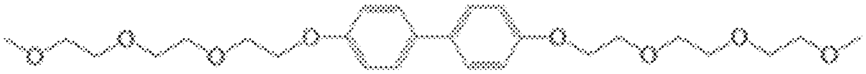
FIG. 29A shows the chemical structures of the surfactants used to induce a planar alignment, according to some embodiments.
Figure 29A:
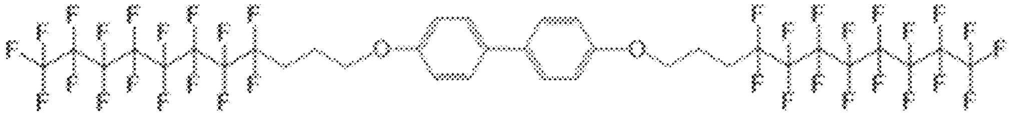
Figure 29B:
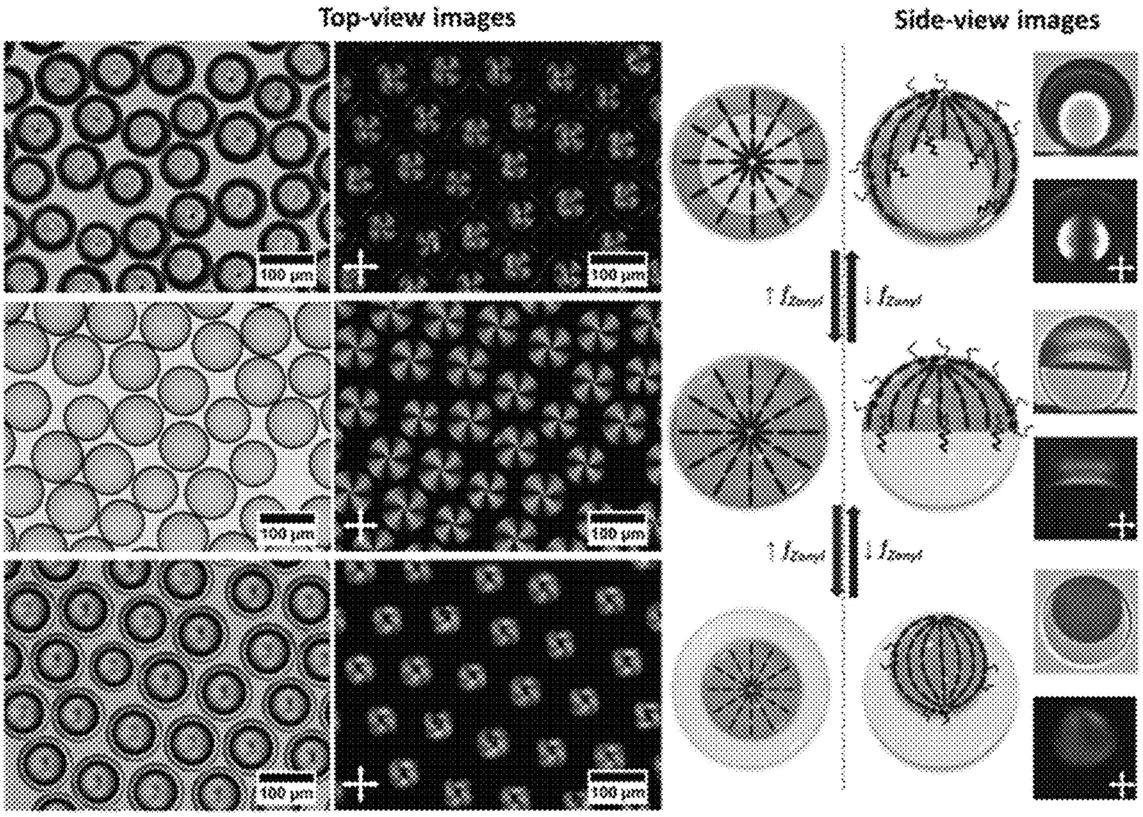
FIG. 29B shows polarized-light optical microscopy images of 5CB-HFE7200 droplets which reconfigure in response to surfactant variation: F/LC/W double emulsions in 0.001% Tween-20 (top), spherical Janus droplets in solution of 0.001 wt. % Tween-20: 0.01 wt. % Zonyl=3:7 (v:v) (middle), and LC/F/W double emulsions in 0.01 wt. % Zonyl (bottom), according to some embodiments.
Figure 29C:
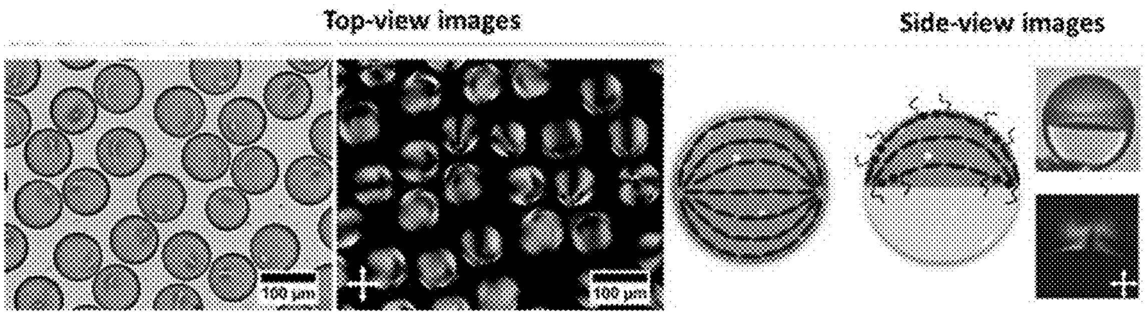
FIG. 29C depicts bipolar Janus droplets with two points defects moving along a line defined by the LC/F/W three-fold junction with a solution of 0.001 wt. % Tween-20 0.01 wt. % Zonyl=3:7 (v:v) used as the continuous phase, according to some embodiments.

Photoswitchable surfactants have been observed to control the LC order at fluid interfaces. Accordingly, a light-responsive LC/F surfactant was synthesized consisting of an azobenzene moiety functionalized with hydrocarbon and fluorocarbon chains (AZO-$R_F$ in FIG. 28A) to see if dynamic changes at the internal interface could affect the morphology or LC anchoring in complex droplets. When this internal surfactant was used instead of CB-$R_F$, we observed that the Janus droplets rapidly and reversibly change their morphology between a more-spherical to a less-spherical (snowman) Janus droplets in response to UV (λ=365 nm) and blue (λ=450 nm) light, respectively. Without wishing to be bound by any theory, this effect was the result of photoinduced isomerization between the more effective trans surfactant the less effective cis form (FIG. 28). In addition, a distortion of the LC order was observed in response to UV light. With 5 min of UV irradiation the birefringent LC texture disappeared, demonstrating a photoinduced nematic-to-isotropic phase transition. This phase transition is attributed to the trans-to-cis photoisomerization of AZO-$R_F$ as the bent-shaped cis-isomers destabilized the order within the mesophase. The same sample was then irradiated with a 450 nm light and the mesophase was recovered within seconds, confirming that the observed photoinduced phase transition was caused by photoisomerization of the azobenzene units and not by local thermal excitation or degradation.

Example 9

The following example illustrates tuning the internal ordering of LC double emulsions, according to some embodiments.

Controlling the LC ordering within complex droplets is central to their utility. Consequently, a bolaamphiphilic surfactant, CB-diTEG (FIG. 29A) was designed, which stabilized the aqueous interface and promoted an alternative planar anchoring of the LC molecules. The surfactant contained a non-polar biphenyl (mesogenic) aromatic core substituted with hydrophilic triethylene glycol groups. The CB-diTEG was added to the dispersed phase (containing LC/F internal surfactants) and initially transformed the spherical LC droplets into a monopolar configuration, wherein the mesogens now aligned parallel (planar) to the LC-W interface and remained perpendicular to the LC-F interface (FIG. 29). In addition, a single point defect was localized near the pole of the Janus and F/LC/W droplets. In the case of LC/F/W double emulsions, CB-diRF internal surfactant was used to produce planar alignment at the LC/F interface and produced a bipolar configuration in which two diametrically opposite point defects were present at the poles. Interestingly, a bipolar configuration was also obtained in Janus LC droplets by combining CB-diTEG and CB-diRF surfactants. This bipolar configuration exhibits constant LC fluctuation as a result of the fact that the two-point defects are not equatorial poles of the Janus droplets. In this case the defects appear to be localized along the LC/F/W line tension and the defects do not have a thermodynamic anchoring to a specific location.

Example 10

The following example shows LC double emulsions with complex internal structure, according to some embodiments.

The layered structures of smectics affects the defect configuration requiring more complex internal structure within a droplet than those observed for nematics, thereby introducing new possibilities. To this end, complex droplets were studying with the LC 4-cyano-4'-octylbiphenyl (8CB) which displays a smectic A phase at room temperature and undergoes a phase transition from smectic A (SmA) to nematic (N) at 33° C. (i.e. Cr 21 SmA 33 N 41 I).

Figure 30A:
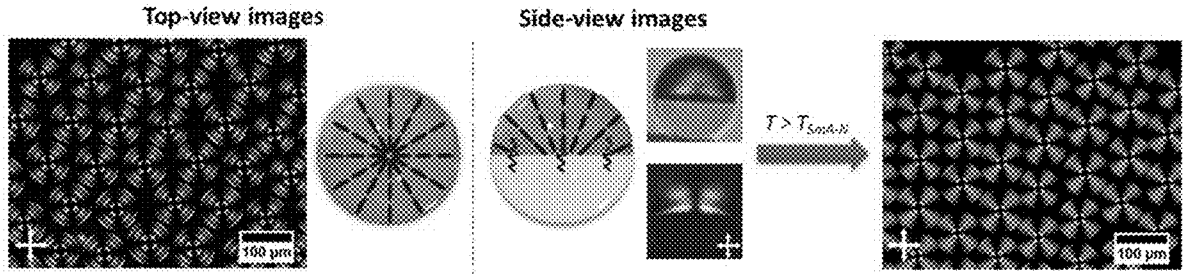
FIGS. 30A-30B show images and schematics for smectic A LC complex emulsions with polarized-light optical microscopy images of 8CB-HFE7200 Janus droplets with (a) a radial alignment, and (b) planar alignment of the mesogens, according to some embodiments.

Spherical complex droplets containing 8CB were obtained by using our evaporation-induced phase separation method and internal surfactants to lower $\gamma_{LC/F}$ and obtain spherical droplets. POM images revealed a radial configuration in the initial smectic phase, indicating a perpendicular alignment of the 8CB molecules to the aqueous interface with an extinction point at the center of the droplets (Maltese cross texture) with concentric layers originated from the center of the droplet (FIG. 30A). Upon heating the droplets above $T_{SmA-N}$ (33° C.), the Maltese cross texture was maintained but the concentric layers disappear, thereby confirming the SmA-to-N transition (FIG. 30A). Further heating above 41° C., the isotropic state was reached and LC birefringence disappeared.

Figure 30B:
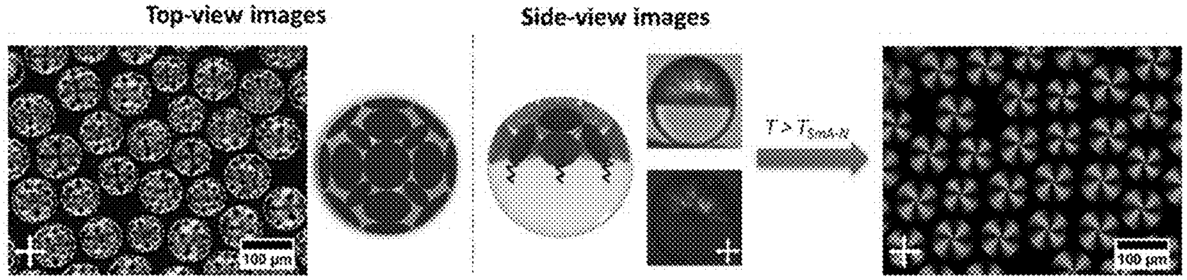
Figure 34A:
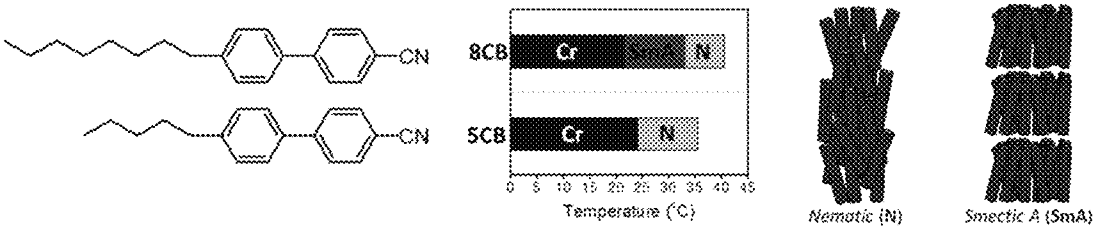
FIG. 34A shows the chemical structures and thermal properties of the liquid crystals, according to some embodiments.
Figure 34B:
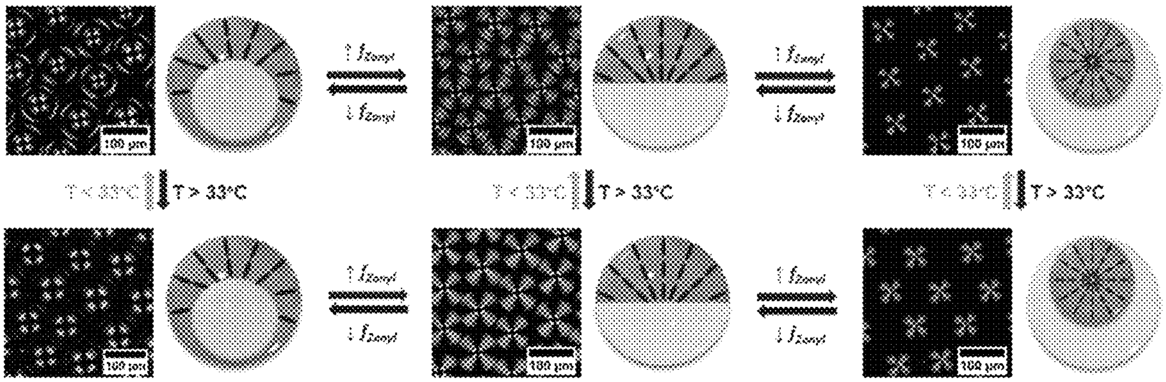
FIG. 34B show polarized-light optical microscopy images of 8CB-HFE7200 droplets with a radial alignment which reconfigure in response to temperature and to variation in the ratio of hydrocarbon and fluorocarbon surfactants, according to one set of embodiments.
Figure 34C:
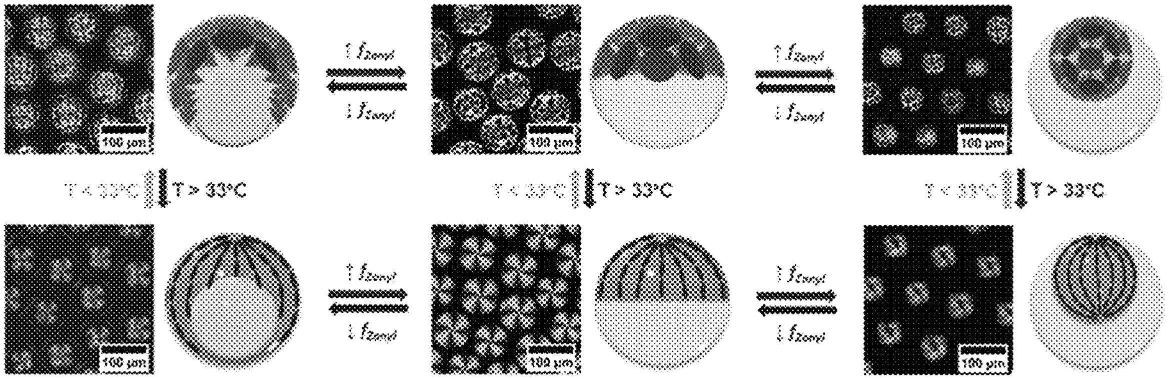
FIG. 34C shows polarized-light optical microscopy images of 8CB-HFE7200 droplets with a planar alignment which reconfigure in response to temperature and to variation in the ratio of hydrocarbon and fluorocarbon surfactants, according to one set of embodiments.

The addition of CB-diTEG produced SmA droplets with 8CB molecules anchoring parallel to the LC-W interface (planar alignment). When examined by POM, multiple focal-conic defects form a polygonal texture within the LC compartment. Without wishing to be bound by theory, this polygonal texture displayed by the SmA LC is the result of half focal-conic domains that pack to fill the half hemispherical space with bases of the cones located at the LC/W interface of the Janus droplet (FIG. 30B). With the SmA to N transition at 33° C., a transition from a polygonal texture to a monopolar configuration was observed with a single point defect located at north pole of the Janus droplets. At temperatures above 41° C., the POM texture again disappeared and the Janus droplets do not have birefringence. The sequence of POM textures of the droplets described above was reversible upon cooling and seen to occur in subsequent heating-cooling cycles. The morphology of these 8CB-HFE7200 droplets can also be dynamically switched between encapsulated (LC/F/W and F/LC/W) and Janus configurations in response to changes in the type and concentration of surrounding surfactants (FIG. 34).

Example 11

The following example describes the templated biomolecule assembly via topological defect-driven functionalization, according to some embodiments.

The detection principle for most LC sensors relies on highly sensitive orientational responses of LCs to molecular-level perturbations in aliphatic tails caused by foreign molecules adsorbed at LC interfaces. However, expanded methodology for the precision integration of recognition elements is certain to provide additional utility to LC-based sensors for the detection of biomolecules, biomarkers, or organisms. To this end, the inventors have recognized and appreciated that the topological defects generated within LC droplets described herein as powerful sites for bioconjugation because they can act as amplifiers of recognition events, causing dramatic changes in orientation of the LC director fields.

Figure 31A:
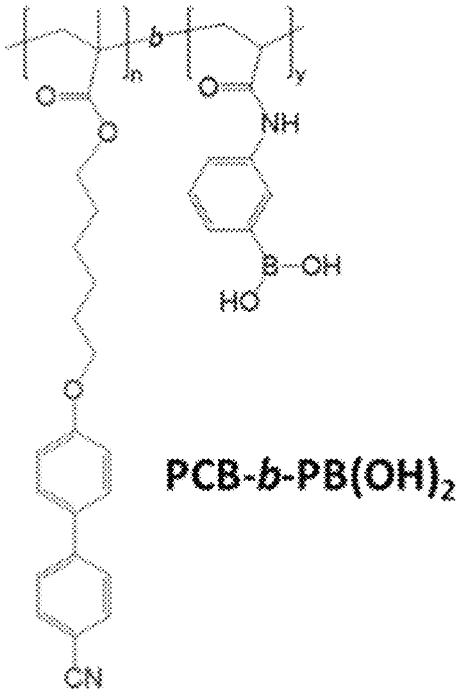
FIG. 31A depicts the chemical structure of PCB-b-PB $(OH)_2$, the boronic acid block copolymer surfactant used for the functionalization of topological defects, according to some embodiments.
Figure 31B:
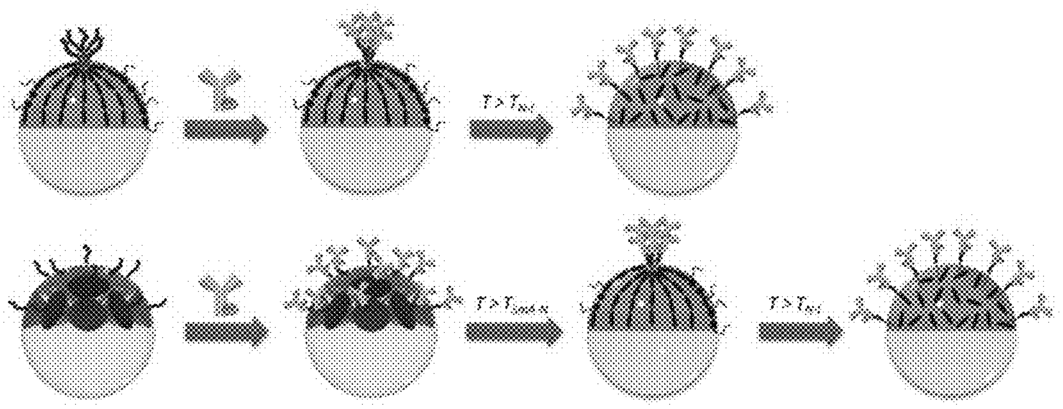
FIG. 31B is a schematic representation of the templated attachment of IgG antibodies at the point defect of nematic (top) and smectic A (down) complex emulsions using PCB-b-PB$(OH)_2$ for antibody immobilization at topological defects, according to some embodiments.
Figure 31C:
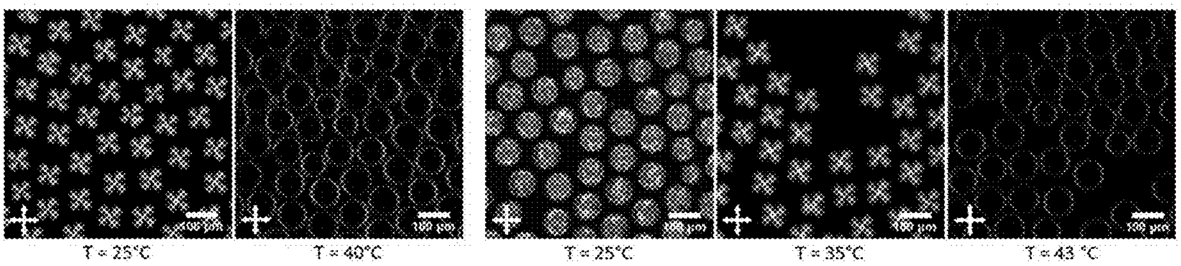
FIG. 31C shows (c) confocal microscopy images of 5CB- and (d) 8CB-containing Janus droplets functionalized with a dye(FITC)-labeled IgG antibody at different temperatures, according to one set of embodiments.

Topological defects in LCs typically assemble around particles that would otherwise disrupt the organization of the phase. Without wishing to be bound by theory, the driving force for this process is the minimization of free energy cost associated elastic strain of LCs. To determine if purposeful functionalization of these sites could occur, the LC/W surface was functionalized with boronic acid groups that could bind to mono- and polysaccharides and N-glycans present in antibodies. Specifically, a block copolymer was synthesized (PCB-b-PB$(OH)_2$ in FIG. 31A) that functioned as a cosurfactant in the emulsification process to prepare 5CB-HFE7200 spherical Janus droplets with a monopolar configuration. A low concentration of PCB-b-PB$(OH)_2$ (1 mg/mL) maintained the droplets within the Janus configuration and did not disrupt the planar surface anchoring provided by CB-diTEG. Immobilization of the antibodies at the LC/W interface was accomplished by boronate ester formation between PCB-b-PB$(OH)_2$ and the N-glycans in the Fc-region of the antibody (FIG. 31B). Successful functionalization was confirmed by the use of FITC-dye labeled IgG antibodies and imaging by a confocal microscope equipped with crossed polarizers. Combined fluorescent and polarized-light micrographs revealed that the fluorescent signal (the green spots) from surface bound IgG antibodies coincide with the location of the topological defect of the monopolar LC Janus droplets (FIG. 31C). Heating IgG-functionalized droplets into an isotropic phase produced a bright fluorescence over the entire LC/W interface (FIG. 31C). These observations confirmed that the polymer bound antibodies selectively localized at the LC defects.

PCB-b-PB$(OH)_2$ block copolymer was also used for bioconjugation of the 8CB spherical Janus droplets. However, no fluorescence was detected by confocal microscopy (FIG. 31C), which, without wishing to be bound by any theory, was probably related to the presence of multiple focal-conic topological defects at the LC/W interface that distribute point emissive signals that are quenched or below the fluorescence detection limits. Functionalization was confirmed upon heating to the nematic phase (T>33° C.), where bright fluorescent was observed at the monopolar nematic topological defect (FIG. 30C). Upon further heating to the isotropic state, fluorescence from the FITC-dye labeled IgG antibodies was observed throughout the LC/W interface, also confirming a covalent attachment of IgG antibodies (FIG. 31C).

Example 12

The following example describes the general procedure for the preparation of LC complex emulsions, according to some embodiments.

Emulsification was conducted by an evaporation-induced phase separation method. Emulsions were fabricated using either bulk emulsification or a microfluidics device, which generates polydisperse or monodisperse droplets, respectively. Both procedures allow the formation of droplets with highly uniform morphology and composition. In a typical bulk emulsification preparation, 35 μL of a solution of LC/HFEs/DCM (1:1:2 volume ratio) was emulsified into 500 μL of a 0.1 wt. % aqueous solution of Tween-20. A vortex mixer at 3000 RPM for 10 seconds was used, and then DCM was slowly evaporated at RT to induce phase separation inside the droplets. Finally, for sample homogenization purposes, droplets were heated to their isotropic states and then cooled to RT before being used for further experiments. This bulk emulsification method generated polydispersed droplets with diameters ranging from 5 to 200 μm as observed by an optical microscopy. Emulsions were also fabricated using a microfluidics device purchased from Dolomite Microfluidic, which generates emulsion droplets with well-controlled sizes. A Telos 2 Reagent Chip (100 μm) was used, and two Mitos P pressure pumps, one for the dispersed phase and one for the continuous phase, were used for controlling the flow rate. The fluids were driven by pressurizing the two individual dispersed and continuous chambers with $N_2$ providing a pulseless, stable flow to the flow focusing chip (pressures: dispersed phase: 200 mbar; continuous phase: 200 mbar). The dispersed phase was split into two crinkled adjacent flow resistors which provide additional flow stability and mixing. The average diameter of the monodispersed droplets generated from this setup were 70±10 m as observed by an optical microscopy.

For the fabrication of dyed complex emulsions, perylene (2 mM) was dissolved in the dispersed phase prior to emulsification.

For the fabrication of spherical complex emulsions, the corresponding amount of CB-$R_F$ (2.5 wt. %), PCB-b-PRF (0.25 wt. %), AZO-$R_F$ (2.5 wt. %) or CB-diRF (2 wt. %) was dissolved in the dispersed phase prior to emulsification.

The dynamic morphology change process from double emulsion H/F/W to Janus to F/H/W through changes in the hydrocarbon/fluorocarbon surfactant mass balance ($f_{Zonyl}$). Each droplet was prepared in a 0.1 wt. % pure Tween-20 solution, and extract 40 L of these pre-formed droplets to solution with different surfactant compositions. The droplets were equilibrated for 15 mins before any measurement.

Example 13

The following describes a general procedure for changing the LC configuration within the LC complex emulsions, according to some embodiments.

To generate LC complex droplets with radial alignment, the dispersed phase (LC/HFE7200/DCM in a 1:1:2 volume ratio with 2.5 wt. % CB-$R_F$ or 0.25 wt. % PCB-b-P$R_F$) was emulsified into a 0.1 wt. % aqueous solution of Tween-20. At the W/LC interface, Tween-20 surfactant was adsorbed with its apolar aliphatic chains penetrating into the LC, promoting a radial orientation of the director of the mesophase in the droplet (mesogens align perpendicular to the aqueous phase).

For the preparation of LC complex emulsions with planar alignment (mesogens align parallel to the aqueous phase), CB-diTEG was dissolved at 5 mg/mL in the dispersed phase (LC/HFE7200/DCM in a 1:1:2 volume ratio with 2.5 wt. % CB-$R_F$ or 0.25 wt. % PCB-b-P$R_F$). LC complex emulsions were fabricated by the emulsification methods described above in 0.001 wt. % pure Tween-20 as the continuous phase. In addition to having the functional surfactant (CB-diTEG) in the emulsion assay, the continuous phase surfactant (i.e. Tween-20) was also essential in the assay to ensure stability of the emulsion droplets. All experiments were performed in a stable emulsion system without observation of coalescence. In the control experiments under the same conditions without CB-diTEG in the dispersed phase, unstable droplets were obtained, coalescing within 5-10 min. For the dynamic morphology change process, 40 L of pre-formed droplets with planar alignment were deposited into 1 mL of solution with different surfactant concentrations. The droplets were equilibrated for 15 mins before any measurement.

Example 14

The following example describes antibody immobilization, in accordance with one set of embodiments.

For the preparation of $B(OH)_2$-functionalized LC emulsion droplets with planar alignment, PCB-b-P$B(OH)_2$ block copolymer (1 mg/mL) and CB-diTEG (5 mg/mL) were dissolved in the dispersed phase (LC/HFE7200/DCM in a 1:1:2 volume ratio with 2.5 wt. % CB-$R_F$ or 0.25 wt. % PCB-b-PRF). $B(OH)_2$-functionalized LC droplets were fabricated in 0.001 wt. % pure Tween-20 as the continuous phase by the emulsification methods described above.

A surfactant solution was prepared by dissolving the surfactants, Tween-20 and Zonyl, in HEPES buffer solution (10 mM HEPES buffer solution; pH=7.5) with a concentration of 0.0003% and 0.007% by weight, respectively. FITC-dye labeled IgG-antibody was attached by pre-dispersing the antibodies (35 g/mL) in 1 mL of the previously prepared surfactant solution and subsequently adding 40 L of pre-formed $B(OH)_2$-functionalized droplets with planar alignment. The emulsions were agitated for 2 h at 150 rpm before recording the confocal microscope images.

Example 15

The following example describes the synthesis of several surfactant compounds, according to one set of embodiments.

Synthesis of 4-Cyano-4'-(3-perfluoro-octyl-propyl) biphenyl (CB-$R_F$)

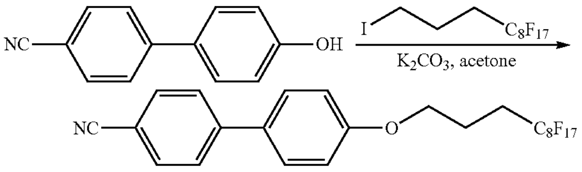

4-cyano-4'-hydroxybiphenyl (0.66 g, 3.40 mmol), 3-(perfluorooctyl)propyl iodide (2.0 g, 3.40 mmol), and potassium carbonate (0.50 g, 3.6 mmol) were stirred in acetone (25 mL). The reaction was stirred at 60° C. for 12 h. The mixture was allowed to cool down to RT and poured into water and extracted twice with ethyl acetate. The combined organic phases were washed with sodium hydroxide 10% (aq.), brine and dried over anhydrous magnesium sulfate. The solution was filtered and the solvent was removed under reduced pressure. The product was purified by flash chromatography on silica gel using DCM. The product was white powder. Yield: 82%. IR (v, $cm^{-1}$): 2222, 1603, 1497, 1203, 1145, 1028. $^{1}$H NMR ($CDCl_3$, 400 MHz, δ, ppm): 7.73-7.67 (m, 2H), 7.67-7.61 (m, 2H), 7.57-7.51 (m, 2H), 7.06-6.93 (m, 2H), 4.10 (t, J=5.9 Hz, 2H), 2.42-2.25 (m, 2H), 2.20-2.09 (m, 2H). $^{13}$C NMR ($CDCl_3$, 100 MHz, δ, ppm): 159.32, 145.26, 132.75, 132.10, 128.60, 127.30, 119.20, 115.20, 110.41, 66.61, 28.09 (t, J=22.4 Hz), 20.74. $^{19}$F NMR ($CDCl_3$, 376 MHz, δ, ppm): −80.73, −114.27, −121.61, −121.87, −122.67, −123.37, −126.06. HRMS (ESI): m/z calcd. for $C_{24}H_{15}F_{17}NO$ $[M+H]^+$, 656.0877; found, 656.0856.

Synthesis of 4-Butyl-(4'-(3-perfluoro-octyl-propyl)) azobenzene (AZO-$R_F$)

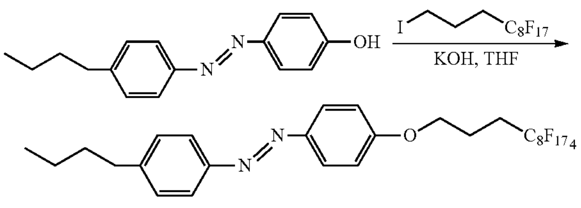

AZO-$R_F$

Perfluoro-octyl propyl iodide (1.76 g, 2.99 mmol) and potassium hydroxide (0.29 g, 5.17 mmol) were dissolved in 10 mL of THF. A solution of 4-butyl-(4'-hydroxy)azobenzene (0.49 g, 1.93 mmol) in 8 mL THF was added dropwise to the reaction mixture. The reaction mixture refluxed for 12 h. Upon cooling, 80 mL DCM was added and the organic phase was washed with brine, dried over sodium sulfate, and reduced under pressure. The resulting orange solid was purified with column chromatography on silica gel using DCM/hexanes (1:3) as eluent in a Biotage Isolera. The product was a yellow-orange powder. Yield: 82%. IR (v, $cm^{1}$): 1595, 1500, 1218, 1141, 1027. $^{1}$H NMR (acetone-$d_6$, 600 MHz, δ, ppm): 7.97-7.90 (m, 2H), 7.86-7.80 (m, 2H), 7.44-7.38 (m, 2H), 7.19-7.14 (m, 2H), 4.30 (t, J=6.1 Hz, 2H), 2.73 (t, 2H), 2.54 (m, 2H), 2.20 (m, 2H), 1.67 (m 2H), 1.41 (m, 2H), 0.96 (t, J=7.4 Hz, 3H). $^{13}$C NMR (acetone-$d_6$, 150 MHz, δ, ppm): 162.2, 151.8, 147.9, 146.9, 130.0, 125.3, 123.3, 115.8, 67.5, 36.0, 34.3, 28.3, 23.0, 21.3, 14.2. $^{19}$F NMR (acetone-$d_6$, 376 MHz, δ, ppm): −80.73, −114.28, −121.61, −121.88, −122.69, −123.37, −126.06. HRMS (ESI): m/z calcd. for $C_{27}H_{24}F_{17}N_2O$ $[M+H]^+$, 715.1612; found, 715.1608.

Synthesis of 4,4'-bis(3-perfluoro-octyl-propyl)biphenyl (CB-diRF)

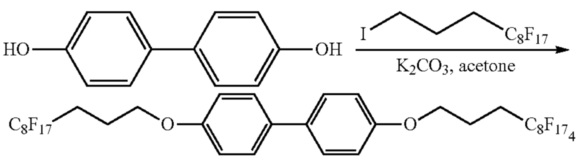

CB-di$R_F$ 4,4'-dihydroxybiphenyl (0.36 g, 1.93 mmol), 3-(perfluorooctyl)propyl iodide (2.5 g, 4.25 mmol), and potassium carbonate (0.80 g, 5.8 mmol) were stirred in acetone (25 mL). The reaction was stirred at 60° C. for 24 h. The mixture was allowed to cool down to RT and poured into water and extracted twice with ethyl acetate. The combined organic phases were washed with sodium hydroxide 10% (aq.), brine and dried over anhydrous magnesium sulfate. The solution was filtered and the solvent was removed under reduced pressure and the residue was purified by flash column chromatography on silica gel using DCM as eluent gradually increasing the polarity of the eluent to DCM/ethyl acetate (8:2). The product was a white powder. Yield: 44%. IR (v, $cm^{1}$): 1603, 1498, 1210, 1145, 1027. $^{1}$H NMR ($CDCl_3$, 400 MHz, δ, ppm): 7.53-7.39 (m, 4H), 7.00-6.90 (m, 4H), 4.09 (t, J=6.0 Hz, 4H), 2.41-2.25 (m, 4H), 2.22-2.06 (m, 4H). $^{13}$C NMR ($CD_2Cl_2$, 298K, 100 MHz, δ, ppm): 158.06, 133.74, 127.84, 115.13, 66.61, 28.19, 20.74. $^{19}$F NMR (acetone-$d_6$, 376 MHz, δ, ppm): −80.73, −114.27, −121.61, −121.88, −122.67, −123.37, −126.06. HRMS (ESI): m/z calcd. for $C_{34}H_{21}F_{34}O_2[M+H]^+$, 1107.0999; found, 1107.0991.

Synthesis of 4,4'-bis(tetra(ethylene glycol)monomethyl ether)biphenyl (CB-diTEG)

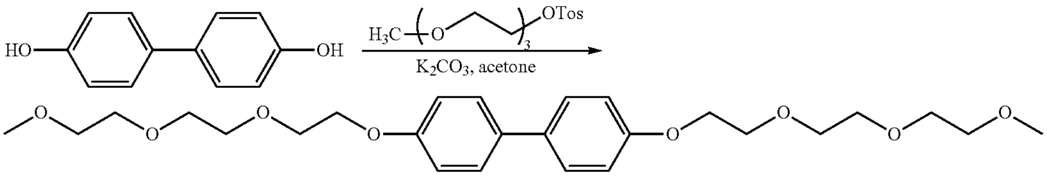

CB-diTEG 4,4'-dihydroxybiphenyl (0.47 g, 2.5 mmol), tri(ethylene glycol)monomethyl ether tosylate (2.0 g, 5.52 mmol), and potassium carbonate (1.04 g, 7.52 mmol) were stirred in acetone (50 mL). The reaction was stirred at 60° C. for 24 h. The mixture was allowed to cool down to RT and the solids filtered off. The solvent was evaporated under reduced pressure and the residue was purified by flash column chromatography on silica gel using hexane/ethyl acetate (1:1) as eluent gradually increasing the polarity of the eluent to ethyl acetate. The product was a white powder. Yield: 67%. IR (v, $cm^{1}$): 1602, 1501, 1242, 1102. $^{1}$H NMR ($CD_2Cl_2$, 298K, 400 MHz, δ, ppm): $^{1}$H NMR ($CDCl_3$, 400 MHz, δ, ppm): 7.51-7.39 (m, 4H), 7.02-6.91 (m, 4H), 4.24-4.10 (m, 4H), 3.94-3.84 (m, 4H), 3.81-3.75 (m, 4H), 3.74-3.63 (m, 8H), 3.62-3.48 (m, 4H), 3.38 (s, 6H). $^{13}$C NMR ($CD_2Cl_2$, 100 MHz, δ, ppm): 158.06, 133.74, 127.84, 127.80, 115.04, 72.09, 71.00, 70.83, 70.73, 69.93, 67.66, 59.19. HRMS (ESI): m/z calcd. for $C_{26}H_{39}O_8[M+H]^+$, 479.2645; found, 479.2650.

Example 16

The following example describes functionalized LC/W surface functionalizing molecules comprising boronic acid groups that can bind to mono- and polysaccharides and N-glycans present in antibodies, according to some embodiments.

Synthesis of PCB-b-PR$_F$ and PCB-b-PB(OH)$_2$ Diblock Copolymers

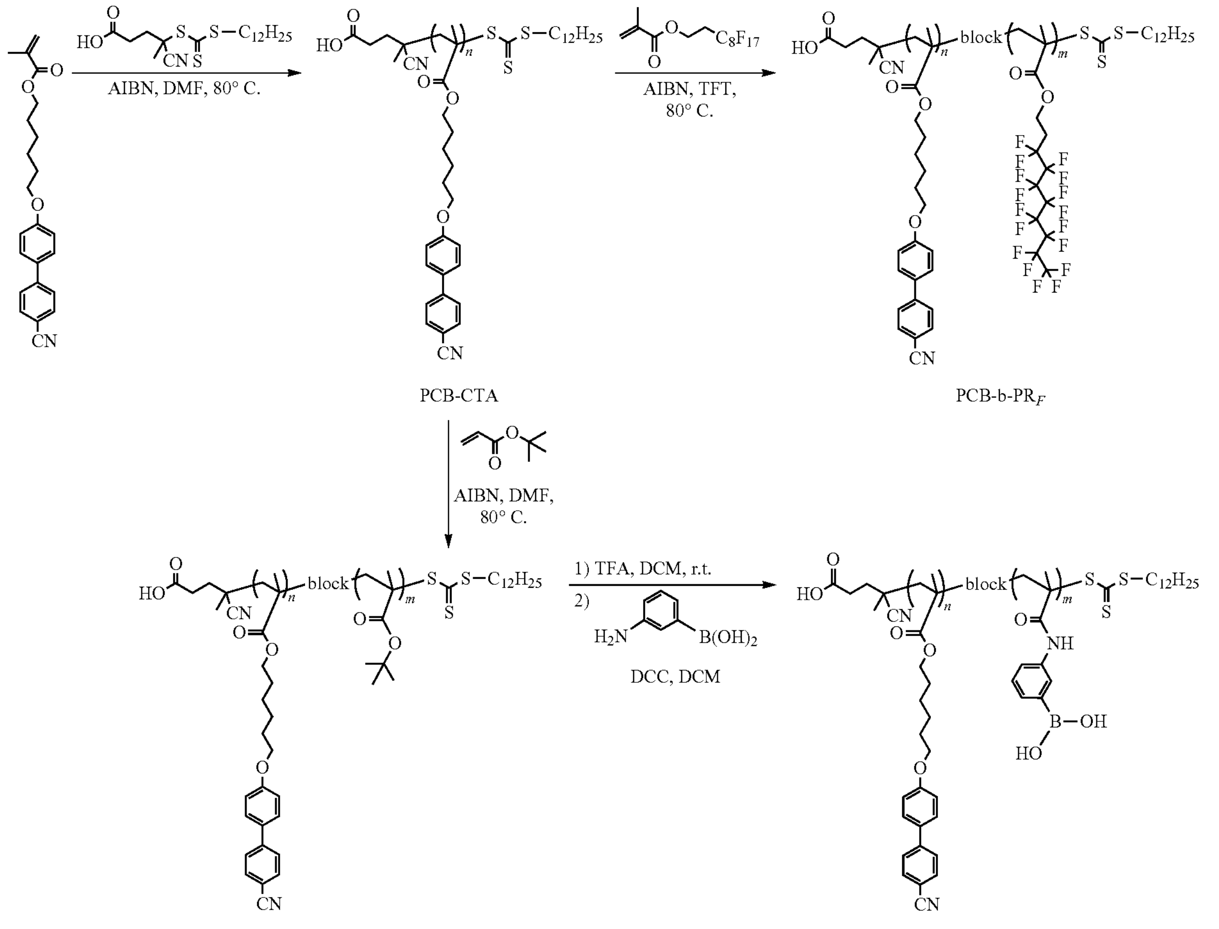

PCB-CTA

PCB-b-PR$_F$

PCB-b-PtBA

PCB-b-PB(OH)$_2$

PCB-CTA. 6-(4-Cyano-biphenyl-4'-yloxy)hexyl methacrylate (2.0 g, 1.10 mmol), 4-Cyano-4-((dodecylsulfanylthiocarbonyl)sulfanyl)pentanoic acid (14.8 mg, 0.036 mmol), AIBN (1.20 mg, 0.004 mmol) and DMF (2.5 mL) were added to a Schlenk flask closed with a rubber septum. The flask was deoxygenated by three freeze-pump-thaw cycles and flushed with argon. The reaction mixture was stirred at 60° C. After 6 h the mixture was quenched with liquid nitrogen and diluted with THF, and then it was carefully precipitated using cold methanol. The polymer was dried in a vacuum oven at 40° C. for 48 h, obtaining PCB-CTA as a yellow powder. Yield: 82%. IR (KBr) ν ($cm^1$): 2219, 1733, 1604, 1495, 1249, 1181. $^1$H NMR ($CDCl_3$, 400 MHz, δ, ppm): 7.73-7.31 (m, 6H), 7.00-6.83 (m, 2H), 4.10-3.78 (m, 4H), 2.14-0.73 (m, 13H). SEC (PS standards): $M'_2$ 9.8 kDa, Đ=1.11.

Block Copolymer PCB-b-PR$_F$. 1H,1H,2H,2H-Perfluorodecyl methacrylate (0.21 g, 0.40 mmol), PCB-CTA (0.20 g, 0.02 mmol), AIBN (0.65 mg, 0.004 mmol) and trifluorotoluene (5 mL) were added to a Schlenk flask closed with a rubber septum. The flask was deoxygenated by three freeze-pump-thaw cycles and flushed with argon. The reaction mixture was stirred at 80° C. After 24 h the mixture was quenched with liquid nitrogen, and then it was carefully precipitated using cold methanol. The polymer was dried in a vacuum oven at 40° C. for 48 h, obtaining PCB-b-PR$_F$ as a yellowish powder. Yield: 78%. IR (KBr) ν ($cm^1$): 2223, 1734, 1605, 1495, 1204, 1147. $^1$H NMR (THF-$d_8$, 400 MHz, δ, ppm): 7.76-7.29 (m, 6H), 6.99-6.71 (m, 2H), 4.34-4.03 (m, 2H), 4.01-3.73 (m, 4H), 2.61-2.26 (m, 2H), 2.14-0.73 (m, 17H). $^{19}$F NMR ($CDCl_3$, 376 MHz, δ, ppm): −81.67 (br), −114.00 (br), −120.35-−127.86. SEC (PS standards): $M_n$=17.0 kDa, Đ=1.15.

PCB-b-PtBA. Tert-butyl acrylate (50 mg, 0.39 mmol), PCB-CTA (0.20 g, 0.02 mmol), AIBN (0.65 mg, 0.004 mmol) and DMF (2 mL) were added to a Schlenk flask closed with a rubber septum. The flask was deoxygenated by three freeze-pump-thaw cycles and flushed with argon. The reaction mixture was stirred at 80° C. After 48 h the mixture was quenched with liquid nitrogen, and then it was carefully precipitated using cold methanol. The polymer was dried in a vacuum oven at 40° C. for 48 h, obtaining PCB-b-PtBA as a yellowish powder. Yield: 82%. IR (ν, $cm^1$): 2224, 1730, 1608, 1496, 1251, 1180. $^1$H NMR ($CDCl_3$, 400 MHz, δ, ppm): 7.77-7.34 (m, 6H), 7.01-6.79 (m, 2H), 4.10-3.78 (m, 4H), 2.53-1.32 (m, 19H). SEC (PS standards): $M_n$=14.3 kDa, D=1.18.

PCB-b-PB$(OH)_2$. Trifluoroacetic acid (3 mL) and PCB-b-PtBA (0.3 g) and were dissolved in anhydrous DCM (15 mL). The reaction was stirred for 24 h at room temperature. The solution was concentrated under reduced pressure and then precipitated using diethyl ether. The polymer was dried in a vacuum oven at 40° C. for 48 h. Yield: 92%. IR (ν, $cm^1$): 3000, 2225, 1732, 1606, 1496, 1250, 1179. $^1$H NMR (DMSO-$d_6$, 400 MHz, δ, ppm): 12.23 (s, 0.3H), 8.05-7.17 (m, 6H), 7.09-6.33 (m, 2H), 4.42-3.56 (m, 4H), 2.43-0.98 (m, 14H). SEC (PS standards): $M_n$=13.0 kDa, D=1.22.

Then, the resulting polymer (0.25 g, 0.02 mmol) and 3-aminophenylboronic acid (0.18 g, 1.35 mmol) were dissolved in anhydrous THF (15 mL). The reaction flask was cooled in an ice bath and flushed with argon, then N,N'-dicyclohexylcarbodiimide (0.28 g, 1.35 mmol) was added dropwise. The mixture was stirred at RT for 48 h under argon atmosphere. The white precipitate was filtered off and washed with THF. The solvent was evaporated and the crude product was carefully precipitated twice using cold methanol. The polymer was dried in a vacuum oven at 40° C. for 48 h, obtaining PCB-b-PB$(OH)_2$ as white powder. Yield: 67%. IR (ν, $cm^1$): 3280, 2222, 1732, 1604, 1495, 1352, 1248. $^1$H NMR (DMSO-$d_6$, 400 MHz, δ, ppm): 7.89-6.48 (m, 9H), 4.08-3.53 (m, 4H), 2.41-0.94 (m, 15H). SEC (PS standards): $M_n$=13.5 kDa, D=1.19.

Example 17

The following example describes the preparation of a cholesterically ordered phase using a chiral dopant.

Figure 35A:
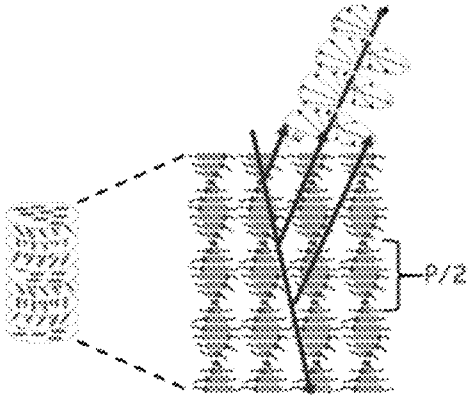
FIG. 35A-35B are schematic representations of a N* phase (left) and chemical structure of the N* components (right), according to some embodiments.
Figure 35B:
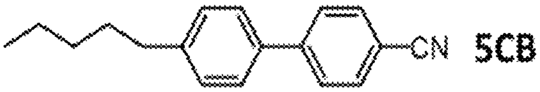
Figure 35B:
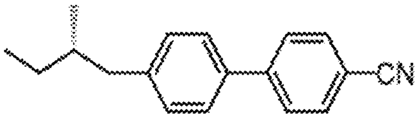

When a small amount of a chiral dopant is added to a nematic LC, helical twisting of the molecular director can be induced leading to a chiral nematic or a cholesteric (N*) LC phase (FIG. 35). The ability of a chiral dopant to induce a twist in the nematic phase is quantified by the helical twisting power (HTP). N* LCs are able to reflect circularly polarized light as a result of their helical organization. The color of the reflected light (so-called photonic band gap, PBG) depends on the helical pitch (p) in following way: $\lambda = n \cdot p \cdot \cos\theta$, where n is the average refractive index, and θ is the incidence angle of the light.

Figure 36A:
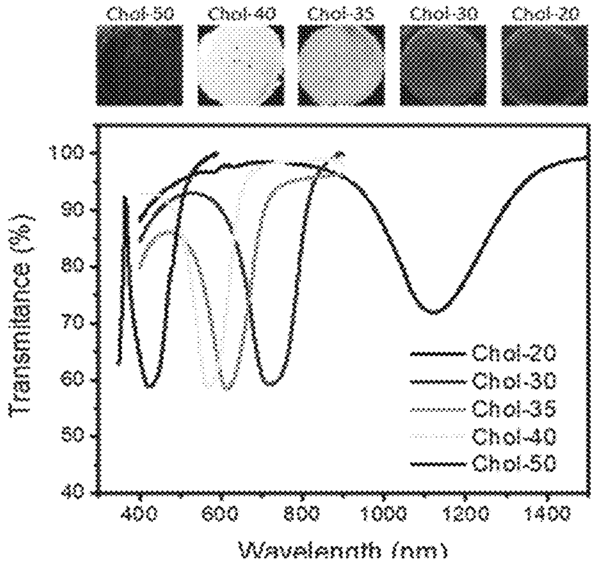
FIG. 36A shows pictures of films (top) made with N* mixtures and the corresponding UV-vis spectra (down), according to some embodiments.
Figure 37A:
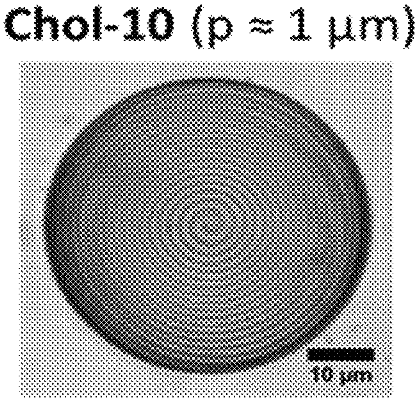
FIG. 37A-37D show optical microscopy images of complex droplets from long-pitch N* LC, according to some embodiments.
Figure 37B:
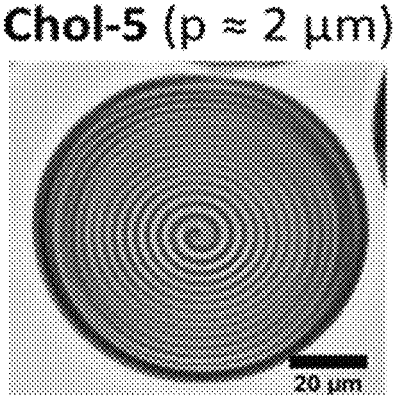
Figure 37C:
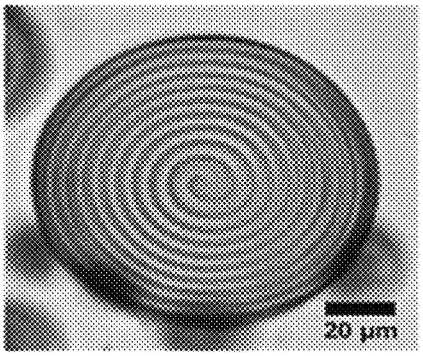
Figure 37D:
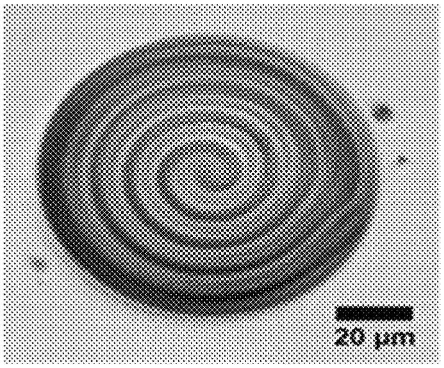

To prepare multicolor photonic complex droplets, a N* mixture was used containing 4-cyano-4'-pentylbiphenyl (5CB) and a chiral dopant. The nomenclature and composition for all the formulations are detailed in FIG. 36A. (S)-4-Cyano-4'-(2-methylbutyl)biphenyl (CB15) was selected as the chiral dopant (HTP≈7.2) because it helped to induce the N* phase in which the PBG can be tuned with CB15 concentration. Doping 5CB with low concentrations of CB15 induces a N* organization but with a PBG out of the UV-vis-NIR region. By changing CB15 concentration from 20 to 50%, the near-infrared reflection band shifts to the blue region of the visible spectrum as evidenced by the UV-vis-NIR spectra in FIG. 36B To produce dynamic multicompartment photonic complex droplets, the N* formulations described above were selected for the hydrocarbon phase and HFE-7200 for the fluorocarbon phase. An evaporation-induced phase separation method was used, as described herein. In a typical preparation, a 1:1:2 volume ratio of N*/HFE7200/DCM was emulsified into a 0.1 wt. % aqueous solution of nonionic surfactant Tween-20. After complete evaporation of DCM, "snowman" Janus droplets with two phase-separated compartments were formed. This bulk emulsification leads to polydisperse droplet sizes, highly uniform morphology and composition of the two compartments was achieved. When studied the N* droplets with a PBG out of the visible region (CB15 concentration from 1 to 10%) by optical microscopy, the alternating dark and bright concentric shells suggest a radial helical structure, which originates from the center of the half-sphere and gives rise to concentric shells of constant refractive index, such that the radial period corresponds to one-half of the cholesteric pitch (FIG. 37)

Figure 38A:
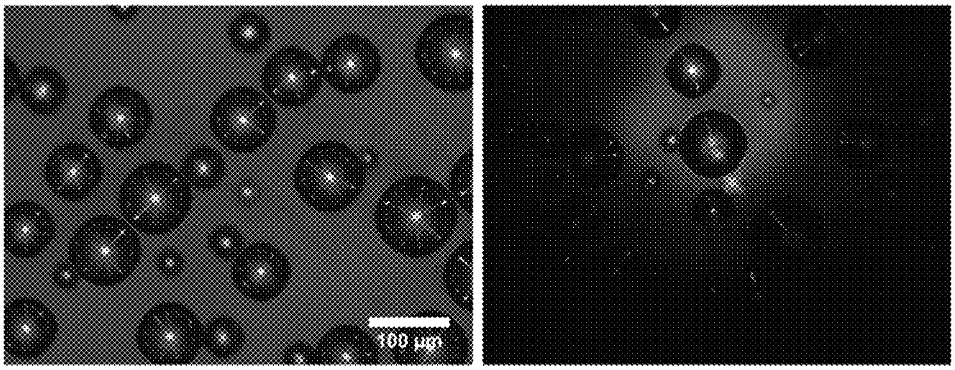
FIG. 38A shows reflectance optical microscopy images, according to one set of embodiments.
Figure 38B:
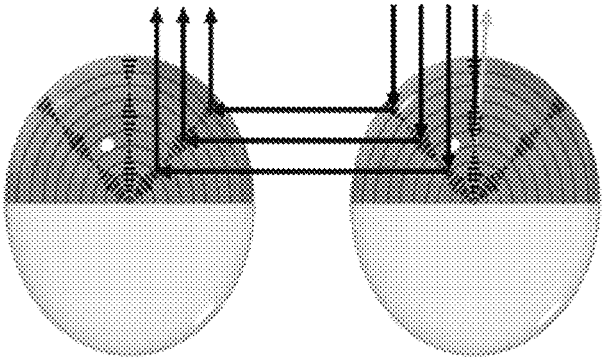
FIG. 38B is a schematic mechanism omnidirectional reflection and cross-communication between the droplets, according to one set of embodiments.

When the helicoidal periodic structure exhibits a reflection band in the visible range (Chol-20 to Chol-50%), the expected optical properties of the N* droplets are obtained, i.e., an overall isotropic structure was observed between crossed polarizers. Interestingly, if the droplets were examined by reflection microscopy, a bright central was observed in each droplet and some additional radial blue lines, as shown in FIG. 38A. Without wishing to be bound by any theory, the origin of this peripheral light pattern of blue lines was attributed to lateral photonic crosstalk between the droplets. The proposed mechanism behind the crosstalk is shown in FIG. 38B. According to Bragg's law of reflection, the center wavelength obeys the rule $\lambda = n \cdot P \cdot \cos\theta$, where θ is the angle between the helix axis and the light propagation direction. When 0=0°, red light with wavelength nP is reflected from the droplet's core as shown as shown in FIG. 38B. Without wishing to be bound by theory, light that hits the periphery (or inside the droplet shown by the dotted ray) makes a non-zero incident angle with the helical axes because of the curvature, which causes an angle-dependent blue-shift from λ=nP. A N* LC of defined pitch can selectively reflect light of different wavelengths depending on the angle of incidence of the light with respect to the helix axis. When θ=45°, light is reflected from the left droplet to the right droplet as depicted in FIG. 38B. If, for example Chol-30 droplets (nP=620 nm), the reflected ray of this crosstalk is λ=438 nm for θ=45°. Droplets with shorter pitch therefore have blue-shifted crosstalk rays, getting bluer until it eventually goes out of the visible spectrum, which is observed for the blue (Chol-50) droplets.

To corroborate the above approach, the illuminated area in the reflectance microscope was closed (FIG. 38A). The illuminated droplets showed the central reflection spot and the reflection-based interactions between neighboring droplets. However, non-illuminated droplets did not show the central reflection spot and only showed the radial reflections coming from the neighboring illuminated droplets. It was also observed that the intensity of photonic cross-interaction becomes weaker or stronger depending on the distance between two nearby droplets, and nearly disappears or is not noticeable when the distance is larger.

Example 18

This example describes the inclusion of $Fe_3O_4$ magnetic nanoparticles in double emulsions.

Particle stabilized emulsions, generally referred to as Pickering emulsions can be of interest for their high stability and biocompatibility when compared to traditional small molecule surfactant-stabilized emulsions. Particular attention has been paid to the fabrication of stimuli-responsive Pickering emulsions, which can be stabilized and destabilized with known triggers. Applied magnetic fields represent an attractive stimulus, as a result of ease of use and non-invasiveness considerations. Magnetic Pickering emulsions employing bare or functionalized magnetic particles (e.g., (e.g., $Fe_3O_4$ nanoparticles), have shown utility in oil/water separation, drug delivery/payload release, and as templating materials. Recent studies on the magnetic properties and specific control of magnetic Pickering emulsions have largely focused on the translational movement toward a magnet or the destabilization through dynamically switching magnetic fields. It has been demonstrated the drastic changes in magnetic properties may occur when confining magnetic nanoparticles (MNPs) to a single emulsion's interface through interfacial electrostatic interactions. It has also been previously shown that control of the magnetic properties of single Pickering emulsions could be achieved through changes in interfacial MNP coverage. Dispersed ferromagnetic nanoparticles, such as $Fe_3O_4$, can exhibit superparamagnetic behavior in solution and lack the sufficiently large magnetic domains to prevent orientational relaxation of the aligned magnet moments after removal of an external magnetic field. However, the interfacial confinement of MNPs can create extended magnetic domains and improved dipole-dipole interactions between MNPs to create a ferromagnetic shell at the emulsion interface that retains magnetization after removal of external magnetic field. Studies of ferromagnetic layers in single emulsions may elucidate opportunities for the control of emulsions by magnetic fields.

Figure 39A:
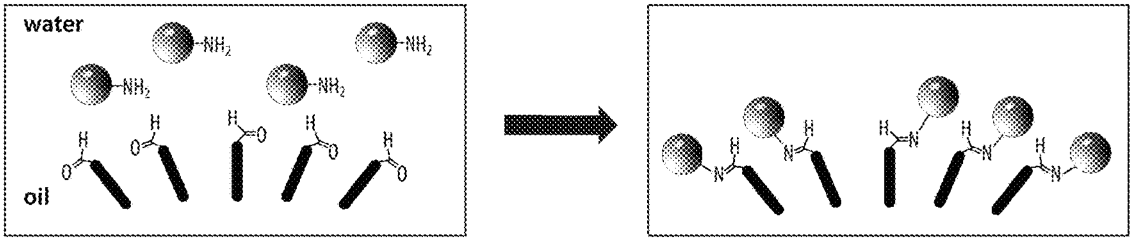
FIG. 39A is a schematic diagram of interfacial imine formation between amine-functionalized magnetic nanoparticles (MNP-$NH_2$) and oil-soluble aldehydes along the oil/water interface, according to some embodiments.
Figure 39B:
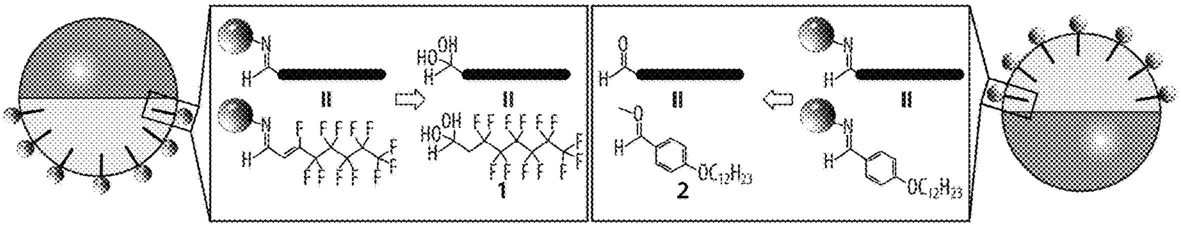
FIG. 39B is a schematic illustration of dynamic double emulsions decorated with magnetic nanoparticles and the retrosynthetic representation of the reaction of the MNP-$NH_2$ with the oil soluble aldehyde or aldehyde hydrate, according to some embodiments.

It was envisioned that further enhancements in controlled emulsion movement and orientation can be achieved by targeted placement and surface confinement of MNPs at double emulsion interfaces. Central to realizing new properties is the selective interfacial reactions needed to localize MNPs at only one of the specific interfaces of these more complex systems. In this Example, interfacial imine chemistry was used to selectively covalently attach amine-functionalized MNPs to one of the interfaces of double emulsions (FIG. 39A). In this Example, water dispersible amine-functionalized $Fe_3O_4$ magnetic nanoparticles ($MNP-NH_2$) reacted with surface active aldehydes, which can be present in hydrate form, to interfacially confine the MNPs (FIG. 39B). Hydrate 1 and Aldehyde 2 are selectively soluble in fluorocarbon (FC) and hydrocarbon (HC) oils, respectively, leading to specific, directed attachment of $MNP-NH_2$ at either the FC or HC interface with water (W). This selective interfacial imine formation enables controlled manipulation of the orientation and directional movements of HC/FC double emulsions and induces ferromagnetic behavior. Double emulsions containing liquid crystals (LCs) provide for additional precision in MNP assembly. Surfactant-driven control of the internal director fields and defects within LC double emulsions are demonstrated and these features can be used to localize MNPs at particular points that can, in turn, strongly couple the LC organization to external magnetic fields.

Magnetic $Fe_3O_4$ nanoparticles (MNP) were synthesized through the hydrolysis of $FeCl_3$ and $FeSO_4$, resulting in polydisperse nanoparticles. Amine functionalization was achieved by attachment of 2-aminoethylphosphonic acid to the MNP surface. The resulting nanoparticles are dispersible in water, with some observed aggregation of the nanoparticles, ranging from ~50-180 nm in size. Magnetic measurements of MNP and $MNP-NH_2$ solutions demonstrated minimal loss of magnetic saturation with functionalization. Magnetic properties of nanoparticles strongly depend on their size and shape, as well as their magnetic character. Sufficiently small $Fe_3O_4$ nanoparticles (<30 nm) have both single domain structure and a flip in magnetization can occur due to thermal effects (e.g., superparamagnetic effect) and thus the polydisperse 10.6±2.6 nm-sized $MNP-NH_2$ are superparamagnetic in solution; however, it was also observed a small magnetic hysteresis suggesting the particles or aggregates partially assemble under applied field. Studies on the MNP size effects on magnetic properties of emulsions were prohibitive as a result of aggregation of MNP in water during and following functionalization, regardless of starting poly or monodispersity. For this reason, bulk synthesized, polydisperse MNPs were used in this Example.

Figure 40A:
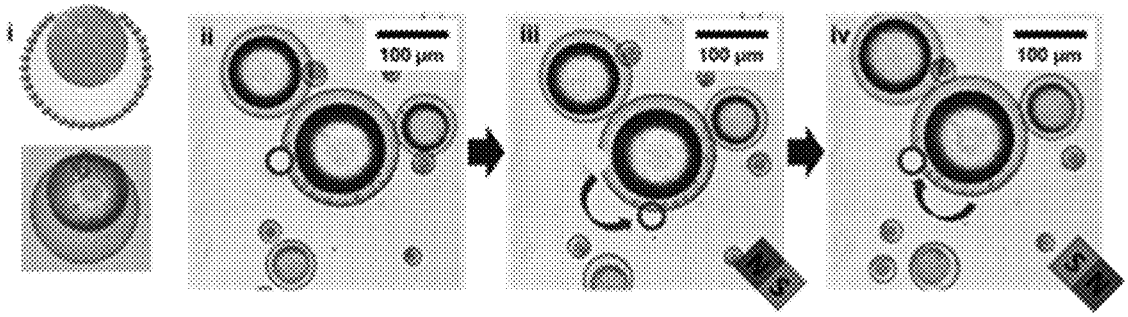
FIG. 40A shows the magnetic response of MNP-$NH_2$ confined to the FC/W interface in HC/FC double emulsions with HC/FC/W, according to some embodiments.

The confinement of $MNP-NH_2$ to the interface of double emulsions comprising diethylbenzene and 2-trifluoromethyl-3-ethoxyperfluorohexane (HFE-7500) enriched with hydrate 1 was studied. Polydisperse emulsions were fabricated by phase separation bulk emulsification with in situ imine formation with the expectation that $MNP-NH_2$ would attach to the FC/W interface during emulsification leading to HC-in-FC-in-water double emulsions (HC/FC/W). Emulsification attempts in the absence of co-surfactants resulted in selective $MNP-NH_2$ attachment to the FC/W interface; however, incomplete phase separation upon cooling was observed, potentially as a result of particles being internalized and thereby inhibiting clean phase separation. This effect is analogous to Pickering particles preventing coalescence in emulsions. To counteract this phenomenon, co-surfactants were introduced in the aqueous phase during emulsification. Low concentrations (0.01 wt %) of FC-surfactant Zonyl FS-300 (Zonyl) helped to promote full phase separation but did not inhibit in situ imine formation allowing for successful $MNP-NH_2$ attachment (FIG. 40A). The anticipated HC/FC/W emulsions were obtained with uniform coverage of $MNP-NH_2$ at the FC/W interface. The droplet morphology is not fully encapsulated, with some HC/W interfacial area present, however, no $MNP-NH_2$ particles were attached to the HC/W interface. Additionally, emulsions were stable to coalescence for greater than 3 months. In control experiments, immediate coalescence of the droplets or no nanoparticle attachment were observed in the absence of Hydrate 1, confirming imine formation is necessary for stabilization of the emulsion and selective interfacial functionalization. These control studies also demonstrate that minimal unreacted $MNP-NH_2$ is present at the interface, signifying that any observed magnetic response is as a result of interfacial confinement due to imine formation.

To elucidate if the interface confined $MNP-NH_2$ in HC/FC/W double emulsions have ferromagnetic behavior, their responses to an external magnetic field was observed. Upon exposure to a magnet, instant rotational motions in space were observed to maximize the magnetic alignment of the functionalized surface with the applied field (FIG. 40A, ii to iii). Upon inversion of the magnetic field (N-S pole flip), the double emulsions rotated back in the opposite direction (FIG. 40A-iii to iv). In addition to the rotation observed, smaller droplets also partially tilt towards and away from the magnet with changes in magnetic field. Further, the emulsions rotated in space with movement of the magnet (N-pole) around the sample. The rotational movements induced by the attraction to and repulsion away from the magnetic field are consistent with ferromagnetic behavior, and emulsions are exhibiting N-S pole orientation that remains even after the removal of magnetic field. If the droplets had a static ferromagnetic ordering, 180° rotation with the N-S pole flip is expected. However, the extent of rotation varied across the sample and 180° rotation was not always observed. The emulsions samples are polydisperse, therefore, exact droplet size impact on response was not obtained, but in general smaller droplets displayed a greater response/rotation to magnetic field. The results suggest that interfacial confinement increased the magnetic domains size and promoted the cooperative alignment of magnetic moments leading to the observed rotational movements; however, over the experimental timeframe relaxation of the MNP organization/magnetic dipoles can result in some randomization of magnetic moments and prevented full 180° rotation in all droplets. Without washing to be bound by any theory, it was reasoned a fully "locked-in" state of the MNPs at the interface of HC/FC/W emulsions was not achieved, resulting in some freedom of movement. It is also noted that other factors, including increased viscous resistance in larger droplets, could prevent full rotation.

Next, the behavior of Janus emulsions with interfacially confined MNP-$NH_2$ was explored. To achieve Janus emulsions with magnetic functionality at the FC/W interface, HC-surfactant Tween-20 was added after the previously described in situ emulsification of magnetic HC/FC/W double emulsions. Significantly high concentrations of Tween-20 (0.5-1 wt %) were necessary to induce this morphology change. This is attributed to the jammed state of the confined MNP-$NH_2$ particles, which prevented quick morphology changes characteristic of surfactant stabilized double emulsions. Without wishing to be bound by any theory, the resistance to reconfiguration can be attributed to the Pickering emulsion and may also be enhanced by magnetic ordering of the MNPs at the FC/W interface. The jammed state further resulted in "snowman" morphologies, wherein the area of FC/W interface is enhanced in the Janus state, which is a consequence of strong interactions of the MNPs with both the fluorocarbon and water (FIG. 40B, i).

Figure 40B:
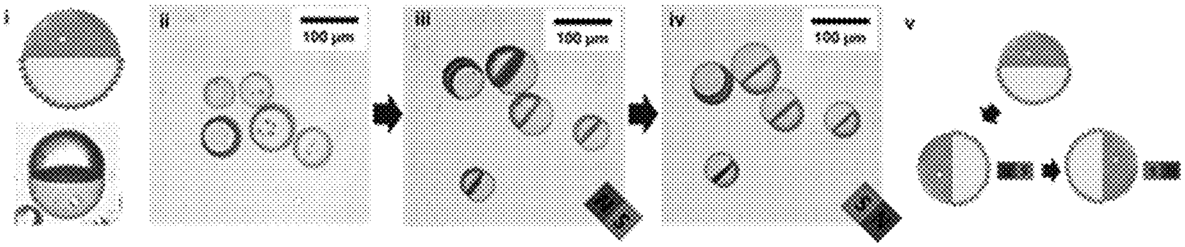
FIG. 40B shows the magnetic response of MNP-$NH_2$ confined to the FC/W interface in HC/FC double emulsions with Janus morphology: i) side-view schematic and image, ii) top-view optical images before exposure to magnetic field, iii) response to magnetic field, iv) response to inversion of magnetic field, v) schematic representation of Janus emulsion orientation change, according to some embodiments

The MNP-$NH_2$ Janus emulsions responded to a magnetic field, overcoming the preferred gravity aligned orientation by flipping onto their side (FIG. 40B, ii to iii). Upon inversion of the magnetic field, the emulsions flipped 180° exhibiting repulsion away from the magnetic field (FIG. 40B, iii to iv). Again, the emulsions are demonstrating N-S pole orientation owing to the ferromagnetic MNP layer resulting in attraction toward and repulsion away from the magnetic field. The observed 180° inversions signal to an increase in dipole-dipole interactions and cooperatively as a result of a more locked in state of the MNPs at the interface and a reduction in competing relaxation, which allowed for retention of dipole alignment over the measurement timeframe. In addition to an increase in jamming, the transition from HC/FC/W morphology to a Janus state increases the asymmetry of MNP-$NH_2$ surface coverage on the emulsions. The intrinsic polar nature of asymmetric, Janus structures enhances ferromagnetic properties in materials. Consequently, structural control of double emulsion morphology provides control over magnetic behavior. Ferromagnetic behavior is further demonstrated by the horizontal rotation of the Janus droplets as a magnet (N-pole) is moved around the samples.

Figure 41:
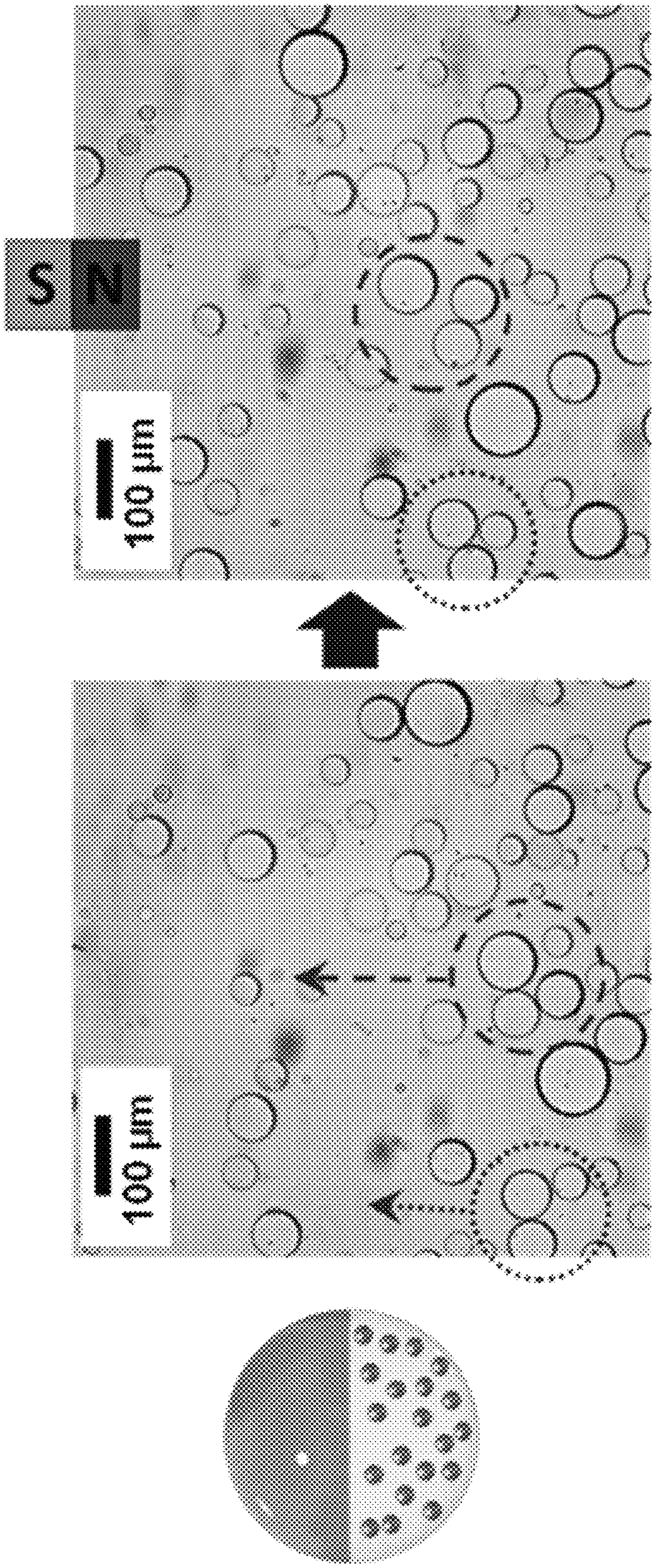
FIG. 41 shows Janus emulsions with MNP-RF dispersed in the FC in an unconfined state exhibited translation movement towards the magnet, but did not demonstrate the change in orientation shown with interfacially confined magnetic nanoparticles, according to one set of embodiments.

To confirm the interfacial confinement is necessary for observed responses to magnetic fields, FC-dispersible magnetic nanoparticles (MNP-RF) were synthesized. Janus emulsions with MNP-RF dispersed within the FC phase (1 mg/mL) exhibited translational movement towards the magnet without changes in droplet orientation (FIG. 41). Inversion of magnetic field did not change the behavior of the emulsion movement or orientation. In total, all of the observations confirm that the interfacial confinement of MNPs imparts ferromagnetic behavior to our double and Janus emulsions.

Figure 42A:
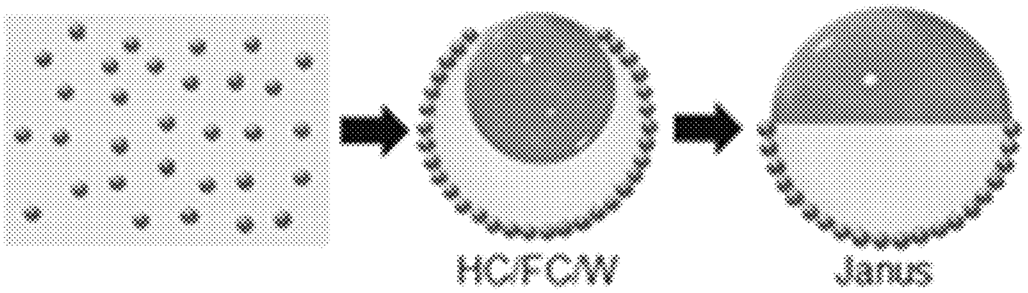
FIG. 42A is a schematic of magnetization of free MNP-$NH_2$, confined MNP-$NH_2$ in HC/FC/W and Janus double emulsions, according to some embodiments.
Figure 42B:
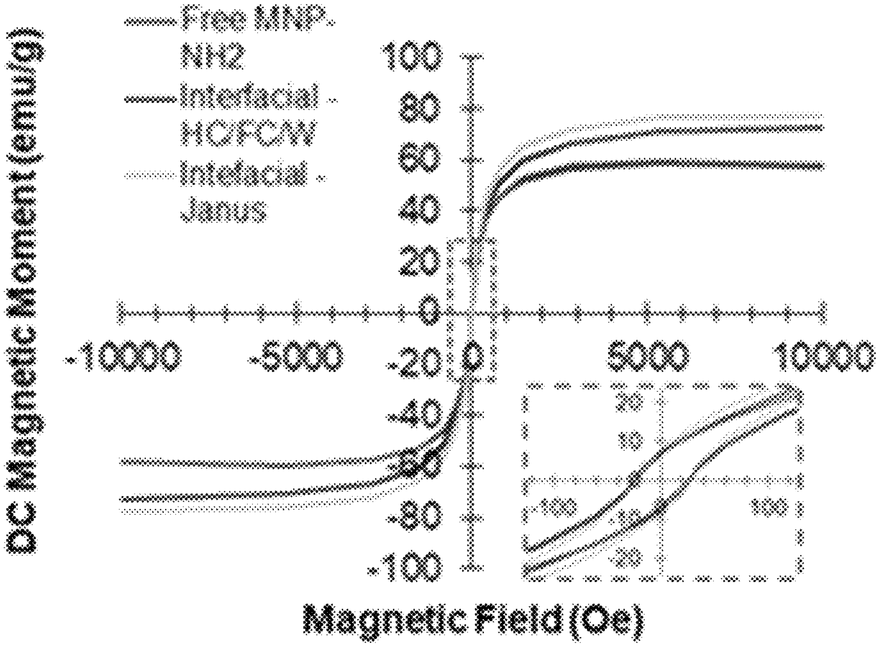
FIG. 42B shows a magnetization curve of free MNP-$NH_2$, confined MNP-$NH_2$ in HC/FC/W and Janus double emulsions with the inset showing magnetic hysteresis, according to some embodiments.

To further study the confined state of the nanoparticles at the interface, the magnetization curve (magnetic field versus magnetic moment) of MNP-$NH_2$'s dispersed in water in comparison to when these double emulsions are attached to the interfaces of double emulsions (FIG. 42A) was determined. Measurements of the magnetic properties of the emulsions were performed in a continuous phase without unreacted MNP-$NH_2$, ensuring the magnetic results were from confined MNP-$NH_2$ only. Confinement at the interface of HC/FC/W emulsions provides an increase in the magnetic saturation from 58.06 to 72.60 emu/g (FIG. 42B). An additional increase in magnetic saturation to 77.25 emu/g was observed with jamming of the MNP-$NH_2$'s caused by the morphology change to the Janus state. These results confirm an increase in ferromagnetic character resulting from improved magnetic dipole alignment capability with confinement and densified packing of MNP-$NH_2$'s at the emulsion interface and increased asymmetry.

Generally, ferromagnetic materials exhibit hysteresis in the magnetization curve as a result of the retention of magnetization. The emulsions prepared in this Example do not exhibit measurable enhancements in coercivity (FIG. 42B, inset). Without wishing to be bound by any theory, it is likely that a fully jammed interface needed to observe a similar increased coercivity is not achieved in this case. The polydispersity of the individual MNP-$NH_2$ particles and the aggregate sizes formed in water could lead to random assembly of the particles at the interface and less than ideal packing capabilities. Therefore, unlike in the assembly of monodisperse $Fe_3O_4$, a close-pack monolayer is not readily achieved. Without wishing to be bound by any theory, this imperfect coverage could weaken the interaction between MNPs along the interface, resulting in lower coercivity. However, in these systems, the weak ferromagnetic coupling manifests in an increase in magnetic saturation and significant macroscopic ferromagnetic control of the emulsions. Simple changes in symmetry are sufficient to induce dramatic increases in macroscopic ferromagnetic responses to magnetic field. Consequently, the emulsions are capable of amplifying small changes in coupling, resulting in a highly sensitive system.

Example 19

The following example describes the inclusion of $Fe_3O_4$ magnetic nanoparticles in double emulsions that include a liquid crystal as the hydrocarbon phase of the Janus droplet.

Following successful generation of ferromagnetic behavior in HC/FC double emulsions, the same strategy to double emulsions containing liquid crystals (LCs) was used to generate programmable MNPs packing at interfaces, leading to distinct magnetic response. LCs have been used to organize (e.g., align) solutes and point defects in the director fields can be used to consolidate particles. The latter highlights how topological defects present within a LC emulsion can precisely position polymers, biomolecules, or micrometer-size particles. As a result, LC templating provides a powerful approach for precisely controlling the interfacial organization/positioning of MNPs. Previous magnetic LC emulsions consisted of single emulsions in which MNPs are dispersed within nematic phases and the results were similar to what is observed with particles dispersed in one of the phases of an isotropic liquid. Specifically, this functionalization enables translational movements towards a magnet. Alternatively, MNPs dispersed in cholesteric single emulsions showed programmable assembly in the internal disclinations of the cholesteric phase. Herein, the use of Janus emulsions comprising two immiscible phases, nematic LC (4-cyano-4'-pentylbiphenyl, 5CB) and FC oil (ethyl perfluorobutyl ether, HFE-7200), to organize MNPs. These Janus droplets were prepared and stabilized by an evaporation-induced phase separation method that includes internal LC/FC surfactants. Aldehyde 2, which is exclusively soluble in 5CB, was added to the system to immobilize $MNP-NH_2$ at the LC/W interface via interfacial imine formation.

Figure 43A:
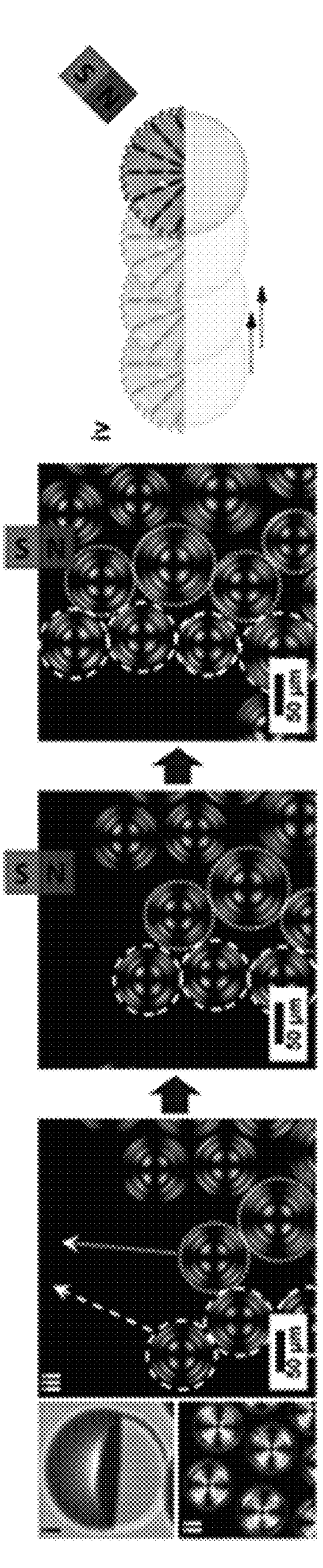
FIG. 43A-43B shows the magnetic response of MNP-$NH_2$-functionalized LC double emulsions with radial and monopolar organizations, respectively: i) Side-view microscopy images, ii) confocal microscopy images, iii) polarized light optical microscopy images, iv) schematic representations, according to one set of embodiments.

Janus droplets with different internal LC director organizations were used to study the different $MNP-NH_2$ arrangements. A radial configuration was first explored, in which 5CB molecules exhibit perpendicular (homeotropic) anchoring at the aqueous interface with no single point defect (singularity) formation at the LC/FC interface (FIG. 43A). Polarized-light optical microscopy (POM) of these droplets showed the expected Maltese cross textures. The presence of Aldehyde 2 did not affect the LC organization within the Janus droplets. In contrast to $MNP-NH_2$ coverage to the HC/FC droplets, which can be observed by side-view optical microscopy, the attachment of $MNP-NH_2$ to the LC/W interface could not be detected optically. The necessity for the Tween-20 co-surfactant and the lower propensity of Aldehyde 2 to assemble at the interface relative to Hydrate 1, both likely contribute to the lower $MNP-NH_2$ coverage. The spatial organization of $MNP-NH_2$ at the LC/W interface is imaged by fluorescent labeling by reacting the $MNP-NH_2$ with n-succinimidyl ester rhodamine. Successful functionalization was confirmed by using a confocal microscope equipped with crossed polarizers. Merged fluorescent and polarized light micrographs reveal bright fluorescence over the entire LC/W interface (the red fluorescent rings), confirming a $MNP-NH_2$ shell at the LC/W interface (FIG. 43A, ii). In the control experiments under the same conditions without the $MNP-NH_2$ attachment step, no fluorescent ring was observed by confocal microscopy, confirming the attachment of immobilized MNPs.

In the absence of an applied magnetic field, the $MNP-NH_2$ functionalized LC/FC Janus droplets randomly disperse in water. Applied magnetic fields magnetize the droplets and they undergo translational motion toward the magnet (FIG. 43A, iii). During movement inter-emulsion attraction between the magnetic dipoles results in the formation of short-range linear chains. As individual droplets and droplet chains get closer in space to the magnet, the size of the chains gradually increased. However, no noticeable change in the POM texture of the Janus radial droplets was observed in response to magnetic fields indicating that the field doesn't change the organization of the LC director field. When the magnetic field was removed, droplets stopped moving, chains lost their integrity, and droplets redisperse in water over the course of 4-5 hours. LC/FC Janus emulsions did not exhibit the same ferromagnetic response (e.g., rotation) as was observed in HC/FC Janus emulsions. Lower overall coverage, and therefore a less jammed state, resulted in a diminished response. Magnetization curves of LC emulsions could not be reliably measured because the lower overall coverage of $MNP-NH_2$ resulted in weaker magnetic response and the mass of attached $MNP-NH_2$ was difficult to accurately obtain.

Figure 43B:
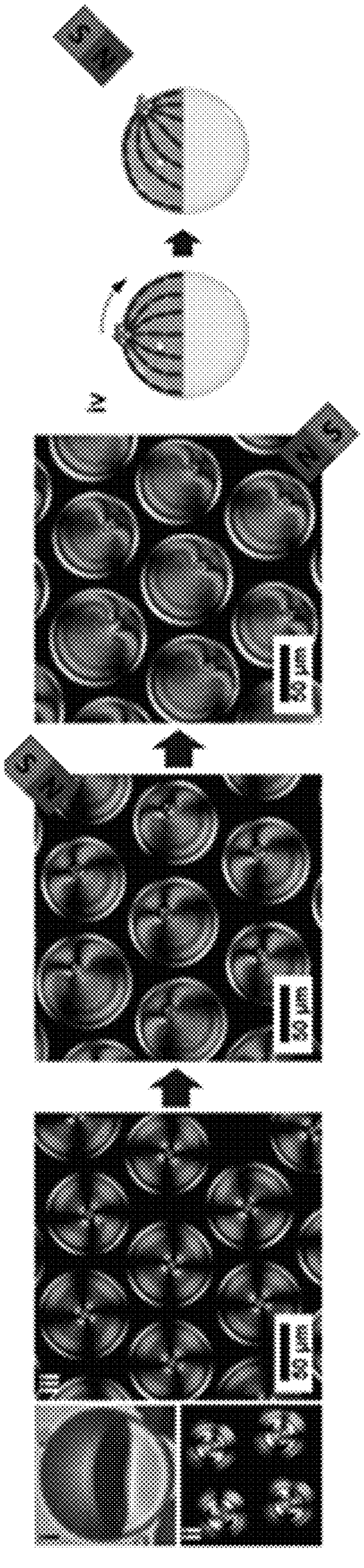

To guide the understanding of the influence of the LC organization on the interfacial assembly of $MNP-NH_2$, Janus droplets with a monopolar configuration were investigated. In this case the singularity resides at the LC/W interface and minimization of the elastic energy places it at the pole of the droplet. These droplets were obtained by using a method based on mesogenic surfactants that promotes an alternative parallel (planar) LC anchoring at the LC/W inter-face. Janus monopolar droplets concentrate the $MNP-NH_2$ assembly at the topological defect at droplet's pole. Aldehyde 2, which is not liquid crystalline, concentrates around the defect core to minimize the free energy and subsequently reacts with $MNP-NH_2$ at this location. POM images confirm that these Janus droplets exhibit a director profile that radiates from a point defect located at the pole, thereby confirming that the monopolar configuration was not altered after imine linking of the $MNP-NH_2$ (FIG. 43B). Combined fluorescent and polarized light micrographs reveal that the fluorescent signal from rhodamine tagged interface-bound $MNP-NH_2$ coincide with the location of the topological defect of the monopolar LC Janus droplets (FIG. 43B, ii). Moreover, heating these droplets into an isotropic phase (TN-I=35° C.) produces a bright fluorescence over the entire LC/W interface. All these observations confirm that $MNP-NH_2$ selectively localize at the LC topological defects. In the control experiments under the same conditions without $MNP-NH_2$ attachment step, no fluorescence was observed by confocal microscopy.

Under the action of a magnetic field, the $MNP-NH_2$ labeled topological defect moves from the north pole to the side of the droplet adjacent to the magnet (FIG. 43B. Control experiments without crossed polarizers were carried out to ensure that we were not simply tilting the Janus droplets on their sides, which would generate the same POM texture. These control experiments confirmed that under a magnetic field the $MNP-NH_2$ labeled topological defect moves towards the magnet without an orientation change or physical translation of the Janus droplet. After removing the magnetic field, the topological defect relaxes to the initial state and location. After heating monopolar droplets into an isotropic phase and delocalization of MNPs, the Janus emulsions presented the same magnetic response (translational motion) as for Janus emulsions with radial organization.

Figure 44A:
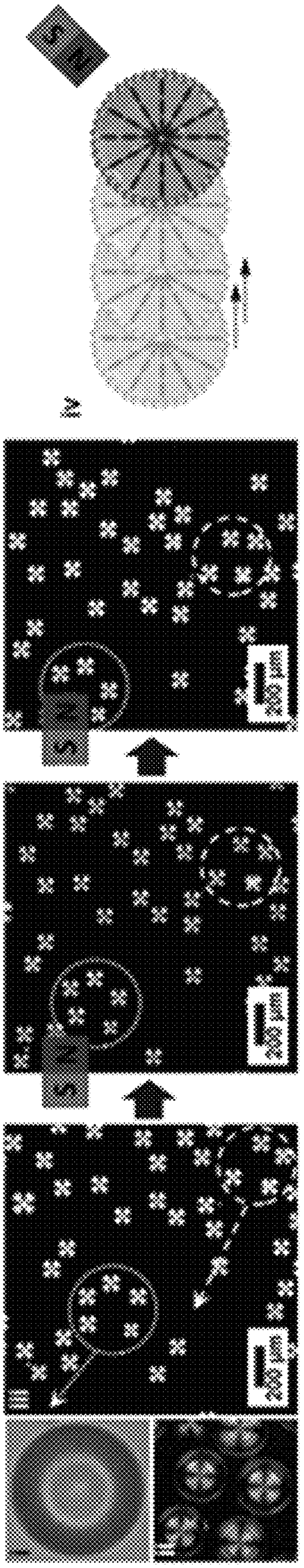
FIG. 44A-44B show the magnetic response of MNP-$NH_2$ functionalized LC single droplets with (FIG. 44A) radial and (FIG. 44B) bipolar organizations: i) Side-view microscopy images, ii) confocal microscopy images, iii) polarized light optical microscopy images wherein the point singularity containing the MNP-$NH_2$ is highlighted by a blue arrow, iv) schematic representations, according to some embodiments.
Figure 44B:
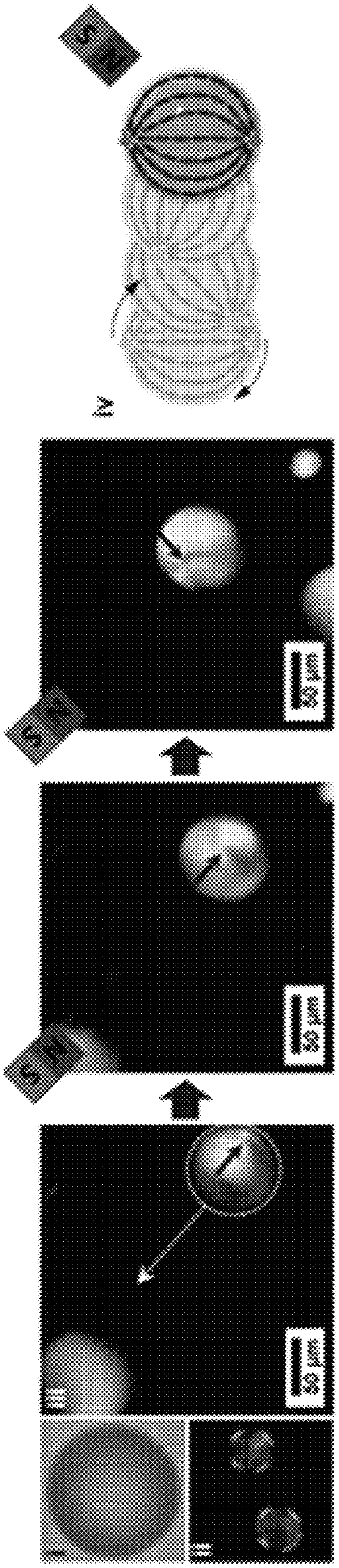

Methods to create $MNP-NH_2$ functionalized single-phase LC emulsions were also employed. By using mesogenic surfactants that control the LC anchoring at interfaces, LC droplets were prepared where mesogens are oriented perpendicular or parallel to the LC/W inter-face, leading to radial or bipolar configurations, respectively (FIG. 44). When $MNP-NH_2$ were attached via imine formation to LC single emulsions with a radial configuration, a magnetic shell was created on the sur-face of the droplets, allowing translational motions by external magnetic field in a controlled manner (FIG. 44A). In single emulsions with a bipolar configuration, two topological defects are located at the poles and precise assembly of $MNP-NH_2$ at the defects was achieved. Bipolar LC MNP emulsions effectively roll toward the magnet, thereby displaying a controllable, but relatively unique, translational motion in response to an applied external magnetic field (FIG. 44).

In conclusion, new manipulations of HC/FC and LC/FC double and Janus emulsions was demonstrated through selective attachment of magnetic nanoparticles. Interfacial imine formation between selectively soluble aldehydes or aldehyde hydrates and water dispersible $MNP-NH_2$ allowed for the strong attachment of $MNP-NH_2$ to the interfaces. Significant $MNP-NH_2$ coverage along the FC/W interface in HC/FC double emulsions resulted in macroscopic ferromagnetic behavior. Both encapsulated core-shell and Janus emulsions exhibited orientational attraction toward and repulsion away from an applied magnetic field owing to the induced magnetic N-S pole direction. Such responses resulted in the rotational movement and changes in orientation in space. The increase in ferromagnetic response was further revealed in magnetization curves, wherein an increase in magnetism with the confinement of $MNP-NH_2$ was observed. However, no increase in coercivity was observed, indicating that small changes in the weak ferromagnetic coupling could induce large changes in macroscopic behavior. Structural symmetry-dependent ferromagnetic response was also demonstrated. In addition, the results described above demonstrate that LC internal ordering is an efficient template to control the organization of $MNP-NH_2$ at the LC/W interface. It is noted that the LC-templated functionalization with $MNP-NH_2$ has features that make it distinct from the functionalization of emulsions comprising isotropic fluids. Although less ferromagnetic behavior was observed, the LC ordering and the selective concentration of MNPs at topological defects results in new ways to manipulate droplets through rolling and change the internal LC director field without changing the orientation or position of the droplet. The ease of attaching MNPs to droplets by interfacial imine forming reactions presents opportunities to create other active emulsion systems.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. An article, comprising:

an aqueous phase;

a mesogenic surfactant;

a droplet, wherein the droplet comprises a hydrocarbon phase, second phase immiscible with the hydrocarbon phase such that an interface is formed between the hydrocarbon phase and the second phase, wherein the article comprises a second interface formed between the hydrocarbon phase and the aqueous phase, wherein the hydrocarbon phase comprises a liquid crystal, and wherein the mesogenic surfactant anchors the liquid crystal to the second interface thereby directing orientation of the molecules of the liquid crystal within the droplet.

2. The article of claim 1, wherein the second phase comprises a fluorocarbon phase, and wherein the hydrocarbon phase and the second phase have a relative interfacial tension of at least 3 mN/m.

3. The article of claim 1, wherein the liquid crystal is smetically ordered.

4. The article of claim 1, wherein the liquid crystal is cholesterically ordered.

5. The article of claim 1, wherein the second phase is a fluorocarbon phase comprising a hydrofluoroether.

6. The article of claim 1, wherein the droplet comprises a Janus droplet.

7. The article of claim 1, wherein the droplet comprises a plurality of Janus droplets.

8. The article of claim 1, wherein the hydrocarbon phase and the second phase form a Janus droplet.

9. The article of claim 1, wherein the hydrocarbon phase and the second phase form an asymmetric Janus droplet.

10. The article of claim 1, wherein the mesogenic surfactant is a nonionic surfactant.

11. The article of claim 1, further comprising an emulsifying agent.

12. The article of claim 1, wherein the second phase comprises a fluorocarbon phase, and wherein the aqueous phase, the hydrocarbon phase, and/or the second phase have a relative interfacial tension of at least 4 mN/m and at most 8 mN/m.

13. The article of claim 1, wherein the liquid crystal comprises at least one point defect.

14. The article of claim 1, wherein the droplet further comprises a plurality of functional groups dispersed uniformly over a surface at a first temperature such that the plurality of functional groups localizes into one of more clusters by a phase transition of the liquid crystal within the droplet.

15. The article of claim 1, wherein molecules of the liquid crystal align perpendicularly to the aqueous phase.

16. The article of claim 1, wherein molecules of the liquid crystal align parallel to the aqueous phase.

17. An article, comprising:

an aqueous phase;

a nonionic surfactant;

a droplet, wherein the droplet comprises a hydrocarbon phase, second phase immiscible with the hydrocarbon phase such that an interface is formed between the hydrocarbon phase and the second phase, wherein the article comprises a second interface formed between the hydrocarbon phase and the aqueous phase, wherein the hydrocarbon phase comprises a liquid crystal, and wherein the nonionic surfactant anchors the liquid crystal to the second interface thereby directing orientation of the molecules of the liquid crystal within the droplet, and wherein the nonionic surfactant comprises Formula (I):

(I)

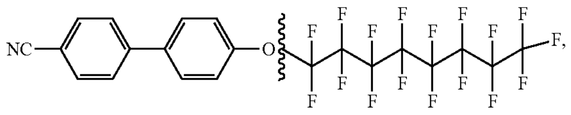

wherein designates connection from an intervening chemical species.

18. A method for preparing the article of claim 17, comprising:

providing an aqueous phase, a hydrocarbon phase, and a fluorocarbon phase, wherein the hydrocarbon phase comprises a liquid crystal; providing a non-ionic surfactant, wherein the nonionic surfactant comprises Formula (I):

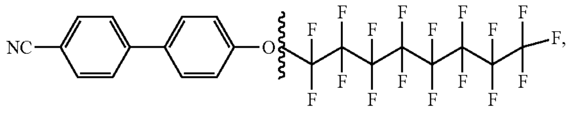

wherein, designates connection from an intervening chemical species; emulsifying the aqueous phase, the hydrocarbon phase, the fluorocarbon phase with an emulsifying agent; and evaporating the emulsifying agent to prepare a colloid.

19. The method of claim 18, comprising applying a stimulus to change the position of the hydrocarbon phase and the fluorocarbon phase.

20. The article of claim 19, wherein the stimulus is light.

* * * * *